(12) United States Patent
Liu et al.

(10) Patent No.: US 8,648,117 B2
(45) Date of Patent: Feb. 11, 2014

(54) METHODS AND COMPOSITIONS FOR TREATING CANCER METASTASIS

(71) Applicant: Golden Biotechnology Corporation, New Taipei (TW)

(72) Inventors: Sheng-Yung Liu, New Taipei (TW); Wu-Che Wen, New Taipei (TW)

(73) Assignee: Golden Biotechnology Corporation, Jersey City, NJ (US)

( * ) Notice: Subject to any disclaimer, the term of this patent is extended or adjusted under 35 U.S.C. 154(b) by 0 days.

(21) Appl. No.: 13/775,079

(22) Filed: Feb. 22, 2013

(65) Prior Publication Data

US 2013/0225691 A1    Aug. 29, 2013

Related U.S. Application Data

(60) Provisional application No. 61/602,489, filed on Feb. 23, 2012.

(51) Int. Cl.
*A61K 35/00* (2006.01)
*A61K 31/12* (2006.01)

(52) U.S. Cl.
USPC .......................... 514/675; 514/676

(58) Field of Classification Search
USPC ................................ 514/675, 676
See application file for complete search history.

(56) References Cited

U.S. PATENT DOCUMENTS

| | | | |
|---|---|---|---|
| 6,649,654 B1 * | 11/2003 | Karin et al. | 514/530 |
| 7,342,137 B1 | 3/2008 | Liu et al. | |
| 2006/0281778 A1 * | 12/2006 | Tagat et al. | 514/292 |
| 2008/0119565 A1 | 5/2008 | Liu et al. | |
| 2013/0142882 A1 * | 6/2013 | Liu et al. | 424/600 |

FOREIGN PATENT DOCUMENTS

| | | |
|---|---|---|
| CN | 102000047 | 4/2011 |
| DE | 10 2010 026 684 A1 | 1/2011 |
| EP | 1942093 A1 | 7/2008 |
| EP | 2 233 463 A1 | 9/2010 |
| EP | 2 329 816 A1 | 6/2011 |
| GB | 2453808 A | 4/2009 |
| WO | WO 2008/089674 A1 | 7/2008 |

OTHER PUBLICATIONS

New Zealand application 607489 office action dated Feb. 27, 2013.
SG App No. 201301342-0 Search Report dated Jul. 16, 2013.
Yang et al. New constituents with iNOS inhibitory activity from mycelium of *Antrodia camphorata*. Planta Med. 2009; 75: 512-516.

* cited by examiner

*Primary Examiner* — Raymond Henley, III
(74) *Attorney, Agent, or Firm* — Wilson, Sonsini, Goodrich & Rosati

(57) ABSTRACT

The present invention provides methods and compositions for treating cancer metastasis by cyclohexenone compounds.

20 Claims, 34 Drawing Sheets

METHODS AND COMPOSITIONS FOR TREATING CANCER METASTASIS

CROSS REFERENCE

This application claims the benefit of U.S. provisional application Ser. No. 61/602,489, filed Feb. 23, 2012, which is incorporated by reference in its entirety.

BACKGROUND OF THE INVENTION

Cancer metastasis is the primary cause of post-operation or post-therapy recurrence in cancer patients. For example, bone metastases, or metastatic bone disease, a class of cancer metastases that results from primary tumor invasion to bone among cancer metastasis, is one of the most common ones of metastasis of various types of human cancers (e.g., breast, lung, prostate and thyroid cancers). The occurrence of bone metastases causes serious morbidity due to intractable pain, high susceptibility to fracture, nerve compression and hypercalcemia. Cancer metastasis remains substantially refractory to therapy despite intensive efforts to develop treatments.

SUMMARY OF THE INVENTION

In one aspect provides herein for treating a disease or condition associated with bone metastasis in a subject comprising administering to the subject in need thereof a therapeutically effective amount of a cyclohexenone compound having the structure:

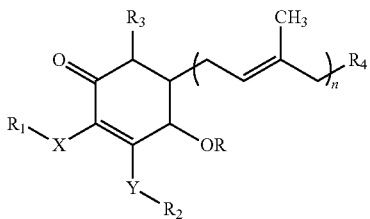

wherein each of X and Y independently is oxygen, $NR_5$ or sulfur;

R is a hydrogen or $C(=O)C_1\text{-}C_8\text{alkyl}$;

each of $R_1$, $R_2$ and $R_3$ independently is a hydrogen, methyl or $(CH_2)_m\text{—}CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1\text{-}C_8\text{alkyl}$, $C_2\text{-}C_8\text{alkenyl}$, $C_2\text{-}C_8\text{alkynyl}$, aryl, glucosyl, wherein the 5 or 6-membered lactone, $C_1\text{-}C_8\text{alkyl}$, $C_2\text{-}C_8\text{alkenyl}$, $C_2\text{-}C_8\text{alkynyl}$, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl;

each of $R_5$ and $R_6$ is independently a hydrogen or $C_1\text{-}C_8$ alkyl;

$R_7$ is a $C_1\text{-}C_8\text{alkyl}$, $OR_5$ or $NR_5R_6$;

m=1-12; and n=1-12; or a pharmaceutically acceptable salt, metabolite, solvate or prodrug thereof.

In another aspect provides herein methods for inhibiting hypercalcemia of malignancy in a subject, comprising administering to the subject in need thereof a therapeutically effective amount of a cyclohexenone compound having the structure:

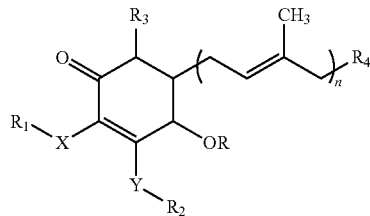

wherein each of X and Y independently is oxygen, $NR_5$ or sulfur;

R is a hydrogen or $C(=O)C_1\text{-}C_8\text{alkyl}$;

each of $R_1$, $R_2$ and $R_3$ independently is a hydrogen, methyl or $(CH_2)_m\text{—}CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1\text{-}C_8\text{alkyl}$, $C_2\text{-}C_8\text{alkenyl}$, $C_2\text{-}C_8\text{alkynyl}$, aryl, glucosyl, wherein the 5 or 6-membered lactone, $C_1\text{-}C_8\text{alkyl}$, $C_2\text{-}C_8\text{alkenyl}$, $C_2\text{-}C_8\text{alkynyl}$, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl;

each of $R_5$ and $R_6$ is independently a hydrogen or $C_1\text{-}C_8$ alkyl;

$R_7$ is a $C_1\text{-}C_8\text{alkyl}$, $OR_5$ or $NR_5R_6$;

m=1-12; and n=1-12; or a pharmaceutically acceptable salt, metabolite, solvate or prodrug thereof.

In another aspect provides herein methods for inhibiting bone resorption in a subject comprising administering to the subject in need thereof a therapeutically effective amount of a cyclohexenone compound having the structure:

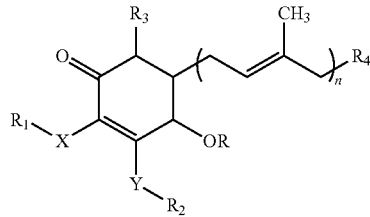

wherein each of X and Y independently is oxygen, $NR_5$ or sulfur;

R is a hydrogen or $C(=O)C_1\text{-}C_8\text{alkyl}$;

each of $R_1$, $R_2$ and $R_3$ independently is a hydrogen, methyl or $(CH_2)_m\text{—}CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1\text{-}C_8\text{alkyl}$, $C_2\text{-}C_8\text{alkenyl}$, $C_2\text{-}C_8\text{alkynyl}$, aryl, glucosyl, wherein the 5 or 6-membered lactone, $C_1\text{-}C_8\text{alkyl}$, $C_2\text{-}C_8\text{alkenyl}$, $C_2\text{-}C_8\text{alkynyl}$, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl;

each of $R_5$ and $R_6$ is independently a hydrogen or $C_1\text{-}C_8$ alkyl;

$R_7$ is a $C_1\text{-}C_8\text{alkyl}$, $OR_5$ or $NR_5R_6$;

m=1-12; and n=1-12; or a pharmaceutically acceptable salt, metabolite, solvate or prodrug thereof.

In another aspect provides herein methods of treating osteolytic lesions in a subject, comprising administering to the subject in need thereof a therapeutically effective amount of a cyclohexenone compound having the structure:

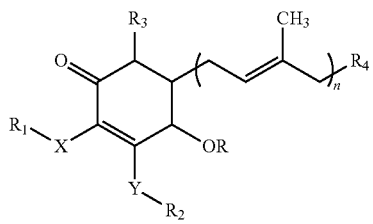

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$ alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1a: Relative change (%) in body weight during the study (mean±SD). Body weight at sacrifice, maximum bodyweight and weight loss from maximum body weight were statistically analyzed and the results are shown in FIGS. 1b, 2 and 2b (not shown), respectively. The rise in mean body weight of control group at day 25 is due to euthanasia of moribund animals at day 24. FIG. 1b: Body weight at sacrifice (relative change from day 0, mean±SD). Statistical analysis was performed using One way ANOVA with logarithmic transformation followed by Dunnett's-test for comparison against the control group. One asterisk (*) indicates a statistically significant difference with a p-value<0.05. Animals in group 5 had higher body weight at sacrifice.

FIG. 3a: Total osteolytic lesion area ($mm^2$) at sacrifice (mean±SD). The results are shown as the sum of areas of bone lesions in right and left tibia and femur/animal. Statistical analysis was performed using Kruskal Wallis test followed by Mann-Whitney test for comparison against the control group. One asterisk (*) indicates a statistical significance with p-value<0.05, two asterisks () a statistical significance with p-value<0.01 and three asterisks (*) a statistical significance with p-value<0.001. Osteolysis was inhibited in groups 2, 4 and 5. FIG. 3b: Mean osteolytic lesion area ($mm^2$) at sacrifice (mean±SD). The results are shown as the mean areas of individual bone lesions in right and left tibia and femur/animal. Statistical analysis was performed using Kruskal Wallis test followed by Mann-Whitney test for comparison against the control group. One asterisk (*) indicates a statistical significance with p-value<0.05, two asterisks () a statistical significance with p-value<0.01 and three asterisks (*) a statistical significance with p-value<0.001. NS=Non-significant. Osteolytic lesions were smaller in groups 2, 4 and 5. FIG. 3c: Number of osteolytic lesions at sacrifice (mean±SD). The results are shown as the count of individual bone lesions in right and left tibia and femur/animal. Statistical analysis was performed using Kruskal Wallis test followed by Mann-Whitney test for comparison against the control group. One asterisk (*) indicates a statistical significance with p-value<0.05, two asterisks () a statistical significance with p-value<0.01 and three asterisks (*) a statistical significance with p-value<0.001. NS=Non-significant. There were less osteolytic lesions in groups 2 and 5, but more in group 3.

FIG. 6a: Relative change from day −4 to day 17 in serum TRACP 5b activity (mean±SD). Statistical analysis was performed using One way ANOVA with logarithmic transformation followed by Dunnett's-test for comparison against the control group. Three asterisks (*) indicate a statistical significance with p-value<0.001. TRACP 5b activity was decreased in group 2. FIG. 6b: Relative change from day −4 to day 24 in serum TRACP 5b activity (mean±SD). Statistical analysis was performed using One way ANOVA with logarithmic transformation followed by Dunnett's-test for comparison against the control group. Three asterisks (*) indicate a statistical significance with p-value<0.001. TRACP 5b activity was decreased in group 2.

FIG. 8a: Relative change from day −4 to day 17 in serum PINP values (mean±SD). Statistical analysis was performed using One way ANOVA with logarithmic transformation followed by Dunnett's-test for comparison against the control group. One asterisk (*) indicates a statistical significance with p-value<0.05. PINP activity was decreased in group 2. FIG. 8b: Relative change from day −4 to day 24 in serum PINP values (mean±SD). Statistical analysis was performed using One way ANOVA with logarithmic transformation followed by Dunnett's t-test for comparison against the control group.

FIG. 14a: Relative change (%) in body weight during the study (mean±SD). Body weight at sacrifice, maximum bodyweight and weight loss from maximum body weight were statistically analyzed and the results are shown in FIGS. 14b, 15a and 15b, respectively. FIG. 14b: Body weight at sacrifice (relative change from day 0, mean±SD). Statistical analysis was performed using One way ANOVA with logarithmic transformation followed by Dunnett's test for comparison against the control group. Statistically significant differences were not observed.

FIG. 15a: Maximum body weight obtained during the study (relative change from day 0, mean±SD). Statistical analysis was performed using One way ANOVA with logarithmic transformation followed by Dunnett's test for comparison against the control group. Two asterisks () indicate a statistically significant difference with a p-value<0.01. Group 4 obtained more weight during the study. FIG. 15b: Weight loss from maximum body weight (relative change from maximum body weight, mean±SD). Statistical analysis was performed using Kruskal Wallis test followed by Mann-Whitney test for comparison against the control group. Two asterisks () indicate a statistically significant difference with a p-value<0.01. Groups 4 and 5 lost more weight.

FIG. 16a: Total osteolytic lesion area ($mm^2$) at day 28 (mean±SD). The results are shown as the sum of areas of bone lesions in right and left tibia and femur/animal. Statistical analysis was performed using Kruskal Wallis test followed by Mann-Whitney test for comparison against the control group. One asterisk (*) indicates a statistical significance with p-value<0.05 and three asterisks (***) statistical significance with p-value<0.001. Total osteolytic lesion area was decreased in groups 2 and 4. FIG. 16b: Total osteolytic lesion area ($mm^2$) at sacrifice (mean±SD). The results are shown as the sum of areas of bone lesions in right and left tibia and femur/animal. Statistical analysis was performed using Kruskal Wallis test followed by Mann-Whitney test for comparison against the control group. One asterisk (*) indicates a statistical significance with p-value<0.05, two asterisks () a statistical significance with p-value<0.01 and three asterisks (*) a statistical significance with p-value<0.001. Total osteolytic lesion area was decreased in groups 2 and 4.

FIG. 17a: Mean osteolytic lesion area ($mm^2$) at day 28 (mean±SD). The results are shown as the mean areas of individual bone lesions in right and left tibia and femur/animal. Statistical analysis was performed using Kruskal Wallis test followed by Mann-Whitney test for comparison against the control group. One asterisk (*) indicates a statistical significance with p-value<0.05 and three asterisks (***) a statistical significance with p-value<0.001. Osteolytic lesions were smaller in groups 2 and 5 at day 28. FIG. 17b: Mean osteolytic lesion area ($mm^2$) at sacrifice (mean±SD). The results are shown as the mean areas of individual bone lesions in right and left tibia and femur/animal. Statistical analysis was performed using Kruskal Wallis test followed by Mann-Whitney test for comparison against the control group. One asterisk (*) indicates a statistical significance with p-value<0.05 and three asterisks (***) a statistical significance with p-value<0.001. Osteolytic lesions were smaller in groups 2 and 4 at sacrifice.

FIG. 18a: Number of osteolytic lesions at day 28 (mean±SD). The results are shown as the count of individual bone lesions in right and left tibia and femur/animal. Statistical analysis was performed using Kruskal Wallis test followed by Mann-Whitney test for comparison against the control group. One asterisk (*) indicates a statistical significance with p-value<0.05. There were more osteolytic lesions in group 2 because individual lesions were prevented from fusing with each other. FIG. 18b: Number of osteolytic lesions at sacrifice (mean±SD). The results are shown as the count of individual bone lesions in right and left tibia and femur/animal. Statistical analysis was performed using Kruskal Wallis test followed by Mann-Whitney test for comparison against the control group. Two asterisks (**) indicate a statistical significance with p-value<0.01. There were more osteolytic lesions in group 2 because individual lesions were prevented from fusing with each other.

FIG. 22a: Intraosseous tumor area (relative to the intraosseous area). Statistical analysis was performed using Kruskal-Wallis test followed by Mann-Whitney U-test for pairwise comparison against the control group. Two asterisks (**) indicate a statistically significant difference with a p-value<0.01 and one asterisk (*) with a p-value<0.05. Intraosseous tumor area was decreased in groups 2 and 4. FIG. 22b: Total tumor area. Statistical analysis was performed using Kruskal-Wallis test followed by Mann-Whitney U-test for pairwise comparison against the control group. Two asterisks (**) indicate a statistically significant difference with a p-value<0.001. Total tumor area was decreased in group 2.

DETAILED DESCRIPTION OF THE INVENTION

Figure 1A:
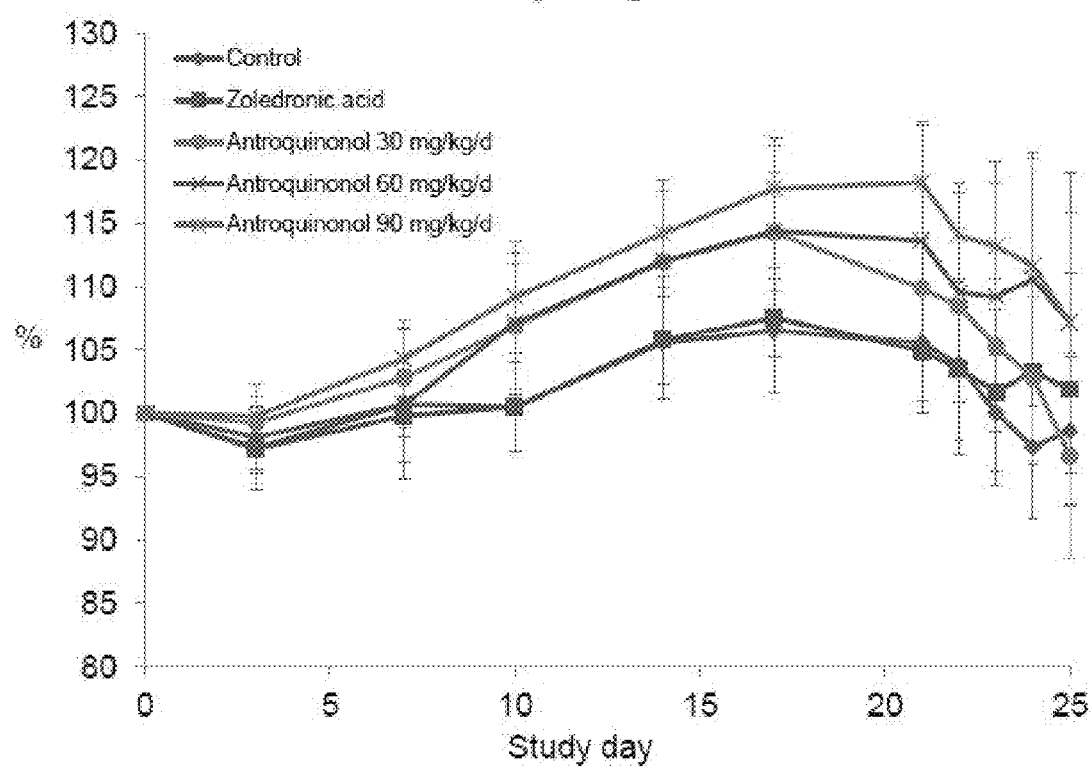
FIGS. 1a and 1b show relative change (%) in body weight during the study (mean±SD) (1a) and at sacrifice (1b) of Groups 1-5.

Common treatments for cancer metastasis include palliative care, surgery, chemotherapy, and radiation therapy. However, cancer metastasis remains substantially refractory to therapy despite intensive efforts to develop treatments. Many synthetic anticancer agents used in chemotherapy cause discomfort or toxicity issues. The invention cyclohexenone compounds, in some embodiments, are obtained from extracts of natural products and provide reduced complications and/or side effects. In some embodiments, provided herein are methods for the treatment of a disease or condition associated with bone metastasis by administering a cyclohexenone compound provided herein to a subject (e.g. a human). The cyclohexenone compounds provide therapeutic benefit to a subject being treated a disease or condition associated with bone metastasis (see Examples 1-4).

Bone metastases, or metastatic bone disease, is a class of cancer metastases that results from primary tumor invasion to bone. Bone-originating cancers like osteosarcoma, chondrosarcoma, and Ewing's sarcoma are rare. And, unlike hematological malignancies that originate in the blood and form non-solid tumors, bone metastases generally arise from epithelial tumors and form a solid mass inside the bone. Bone metastases cause severe pain, characterized by a dull, constant ache with periodic spikes of incident pain. The occurrence of bone metastases causes serious morbidity due to intractable pain, high susceptibility to fracture, nerve compression and hypercalcemia.

Hypercalcaemia or hypercalcemia is an elevated calcium level in the blood. It can be an asymptomatic laboratory finding, but because an elevated calcium level is often indicative of other diseases, a workup should be undertaken if it persists. It can be due to excessive skeletal calcium release, increased intestinal calcium absorption, or decreased renal calcium excretion.

Bone is one of the most common locations for metastasis. While any type of cancer is capable of forming metastatic tumors within bone, the microenvironment of the marrow tends to favor particular types of cancer, including prostate, breast, and lung cancers. Particularly in prostate cancer, bone metastases tend to be the only site of metastasis.

In some embodiments, there are provided methods treating a disease or condition associated with bone metastasis in a subject comprising administering to the subject in need thereof a therapeutically effective amount of a cyclohexenone compound having the structure:

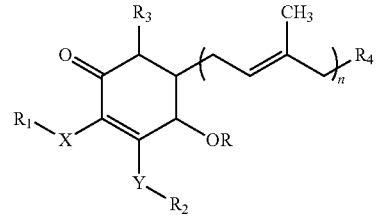

wherein each of X and Y independently is oxygen, $NR_5$ or sulfur;

R is a hydrogen or $C(=O)C_1\text{-}C_8\text{alkyl}$;

each of $R_1$, $R_2$ and $R_3$ independently is a hydrogen, methyl or $(CH_2)_m\text{—}CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1\text{-}C_8\text{alkyl}$, $C_2\text{-}C_8\text{alkenyl}$, $C_2\text{-}C_8\text{alkynyl}$, aryl, glucosyl, wherein the 5 or 6-membered lactone, $C_1\text{-}C_8\text{alkyl}$, $C_2\text{-}C_8\text{alkenyl}$, $C_2\text{-}C_8\text{alkynyl}$, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl;

each of $R_5$ and $R_6$ is independently a hydrogen or $C_1\text{-}C_8$ alkyl;

$R_7$ is a $C_1\text{-}C_8\text{alkyl}$, $OR_5$ or $NR_5R_6$;

m=1-12; and n=1-12; or a pharmaceutically acceptable salt, metabolite, solvate or prodrug thereof. In some embodiments, the subject has breast cancer or prostate cancer. In some embodiments, the subject is human. See Examples 1-4.

In some embodiments, the cyclohexenone compound having the structure

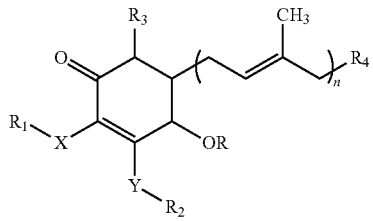

is prepared synthetically or semi-synthetically from any suitable starting material. In other embodiments, the cyclohexenone compound is prepared by fermentation, or the like. For example, Compound 1 (also known as Antroquinonol™ or "Antroq") or Compound 3, in some instances, is prepared from 4-hydroxy-2,3-dimethoxy-6-methylcyclohexa-2,5-dienone. The non-limited exemplary compounds are illustrated below.

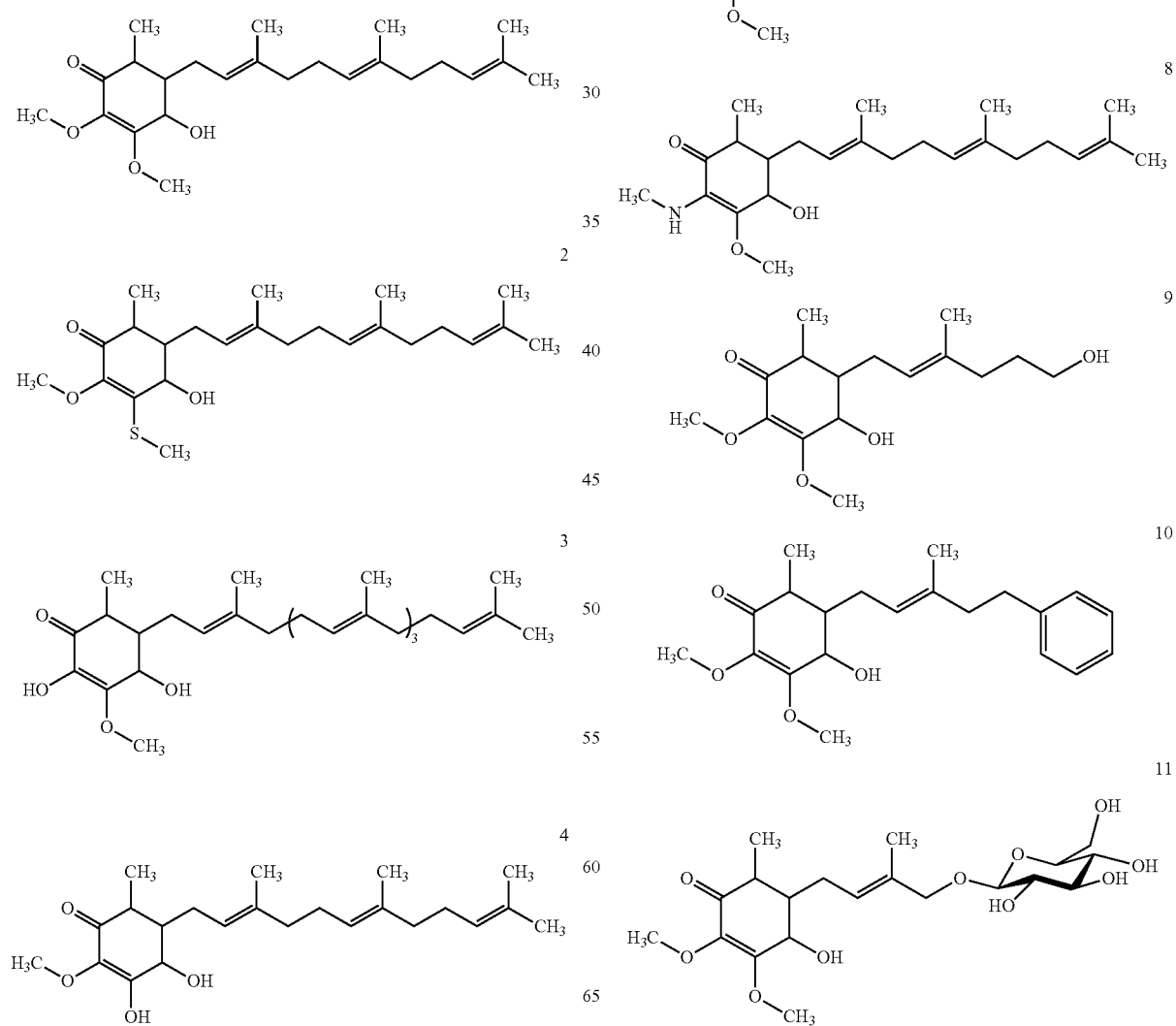

-continued

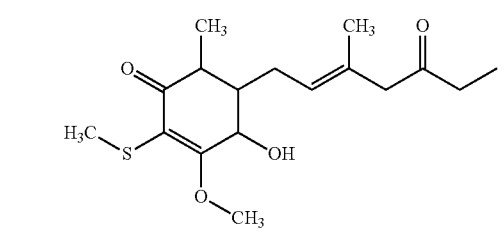
12

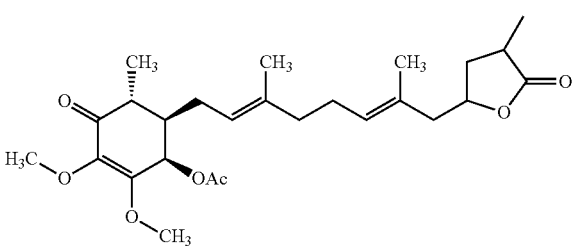
13

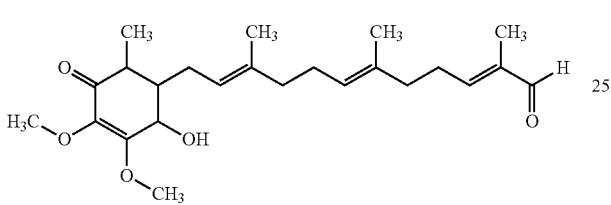
14

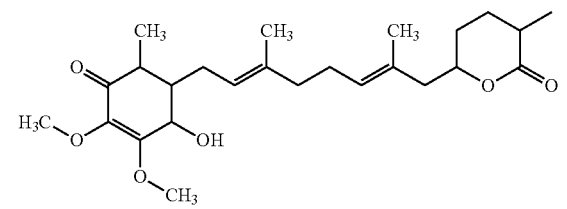
15

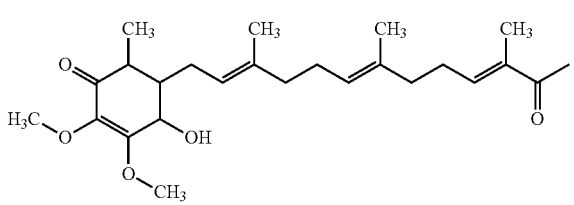
16

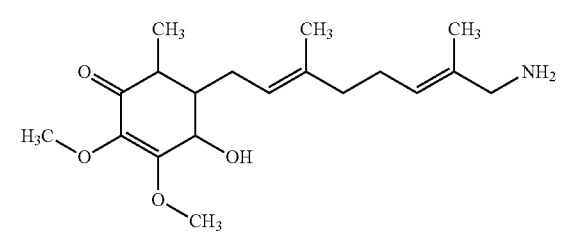
17

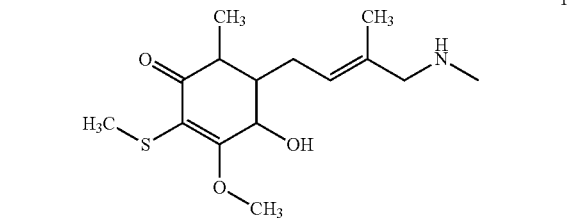
18

-continued

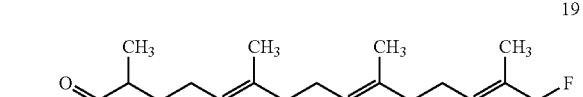
19

20

In other embodiments, the cyclohexenone compound having the structure

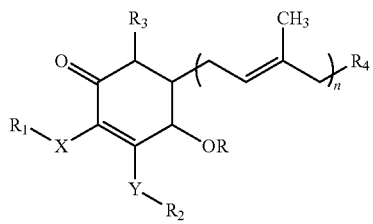

is isolated from the organic solvent extracts of *Antrodia camphorata*. In some embodiments, the organic solvent is selected from alcohols (e.g., methanol, ethanol, propanol, or the like), esters (e.g., methyl acetate, ethyl acetate, or the like), alkanes (e.g., pentane, hexane, heptane, or the like), halogenated alkanes (e.g., chloromethane, chloroethane, chloroform, methylene chloride, and the like), and the like. For example, exemplary Compounds 1-7 are isolated from organic solvent extracts. In certain embodiments, the organic solvent is alcohol. In certain embodiments, the alcohol is ethanol. In some embodiments, the cyclohexenone compound is isolated from the aqueous extracts of *Antrodia camphorata*.

In some embodiments, R is a hydrogen, $C(=O)C_3H_8$, $C(=O)C_2H_5$, or $C(=O)CH_3$. In some embodiments, $R_1$ is a hydrogen or methyl. In certain embodiments, $R_2$ is a hydrogen, methyl, ethyl, propyl, butyl, pentyl or hexyl. In some embodiments, $R_3$ is a hydrogen, methyl, ethyl, propyl, butyl, pentyl or hexyl. In some embodiments, $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$. In some embodiments, $R_4$ is $C_2H_5C(CH_3)_2OH$, $C_2H_5C(CH_3)_2OCH_3$, $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, $C_1$-$C_8$ alkyl, $C_2$-$C_8$ alkenyl, $C_2$-$C_8$ alkynyl, aryl, and glucosyl, wherein the 5 or 6-membered lactone, $C_1$-$C_8$ alkyl, $C_2$-$C_8$ alkenyl, $C_2$-$C_8$ alkynyl, aryl, and glucosyl are optionally substituted with one or more substituents selected from $NR_5R_6$, $OR_5$, $OC(=O)R_7$, C(=O)OR$_5$, C(=O)R$_5$, C(=O)NR$_5$R$_6$, C$_1$-C$_8$ alkyl, C$_2$-C$_8$ alkenyl, C$_2$-C$_8$ alkynyl, C$_3$-C$_8$ cycloalkyl, and C$_1$-C$_8$ haloalkyl. In certain embodiments, R$_4$ is CH$_2$CH=C(CH$_3$)$_2$. In certain embodiments, the compound is

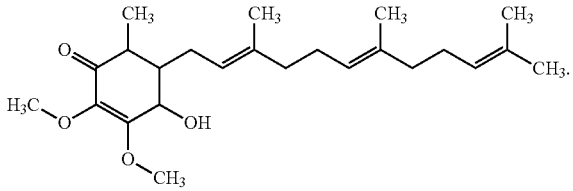 [SMILES: COC1=C(OC)C(O)C(C/C=C(\C)CC/C=C(\C)CCC=C(C)C)C(C)C1=O]

In some embodiments, there are provided methods for inhibiting hypercalcemia of malignancy in a subject comprising administering to the subject in need thereof a therapeutically effective amount of a cyclohexenone compound having the structure:

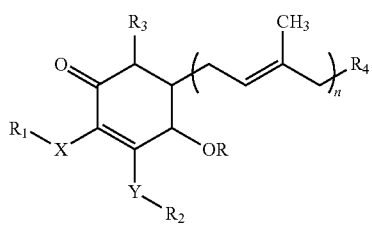

wherein each of X and Y independently is oxygen, NR$_5$ or sulfur;

R is a hydrogen or C(=O)C$_1$-C$_8$alkyl;

each of R$_1$, R$_2$ and R$_3$ independently is a hydrogen, methyl or (CH$_2$)$_m$—CH$_3$;

R$_4$ is NR$_5$R$_6$, OR$_5$, OC(=O)R$_7$, C(=O)OR$_5$, C(=O)R$_5$, C(=O)NR$_5$R$_6$, halogen, 5 or 6-membered lactone, C$_1$-C$_8$alkyl, C$_2$-C$_8$alkenyl, C$_2$-C$_8$alkynyl, aryl, glucosyl, wherein the 5 or 6-membered lactone, C$_1$-C$_8$alkyl, C$_2$-C$_8$alkenyl, C$_2$-C$_8$alkynyl, aryl, and glucosyl are optionally substituted with one or more substituents selected from NR$_5$R$_6$, OR$_5$, OC(=O)R$_7$, C(=O)OR$_5$, C(=O)R$_5$, C(=O)NR$_5$R$_6$, C$_1$-C$_8$ alkyl, C$_2$-C$_8$ alkenyl, C$_2$-C$_8$ alkynyl, C$_3$-C$_8$ cycloalkyl, and C$_1$-C$_8$ haloalkyl;

each of R$_5$ and R$_6$ is independently a hydrogen or C$_1$-C$_8$alkyl;

R$_7$ is a C$_1$-C$_8$alkyl, OR$_5$ or NR$_5$R$_6$;

m=1-12; and n=1-12; or a pharmaceutically acceptable salt, metabolite, solvate or prodrug thereof. In some embodiments, the subject has breast cancer or prostate cancer. In some embodiments, the subject is human. See Examples 1-4.

In some embodiments provide methods for inhibiting bone resorption in a subject comprising administering to the subject in need thereof a therapeutically effective amount of a cyclohexenone compound having the structure:

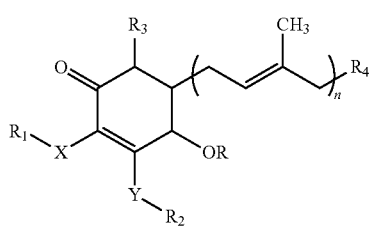

wherein each of X and Y independently is oxygen, NR$_5$ or sulfur;

R is a hydrogen or C(=O)C$_1$-C$_8$alkyl;

each of R$_1$, R$_2$ and R$_3$ independently is a hydrogen, methyl or (CH$_2$)$_m$—CH$_3$;

R$_4$ is NR$_5$R$_6$, OR$_5$, OC(=O)R$_7$, C(=O)OR$_5$, C(=O)R$_5$, C(=O)NR$_5$R$_6$, halogen, 5 or 6-membered lactone, C$_1$-C$_8$alkyl, C$_2$-C$_8$alkenyl, C$_2$-C$_8$alkynyl, aryl, glucosyl, wherein the 5 or 6-membered lactone, C$_1$-C$_8$alkyl, C$_2$-C$_8$alkenyl, C$_2$-C$_8$alkynyl, aryl, and glucosyl are optionally substituted with one or more substituents selected from NR$_5$R$_6$, OR$_5$, OC(=O)R$_7$, C(=O)OR$_5$, C(=O)R$_5$, C(=O)NR$_5$R$_6$, C$_1$-C$_8$ alkyl, C$_2$-C$_8$ alkenyl, C$_2$-C$_8$ alkynyl, C$_3$-C$_8$ cycloalkyl, and C$_1$-C$_8$ haloalkyl;

each of R$_5$ and R$_6$ is independently a hydrogen or C$_1$-C$_8$ alkyl;

R$_7$ is a C$_1$-C$_8$alkyl, OR$_5$ or NR$_5$R$_6$;

m=1-12; and n=1-12; or a pharmaceutically acceptable salt, metabolite, solvate or prodrug thereof. In some embodiments, the subject has breast cancer or prostate cancer. In some embodiments, the subject is human. See Examples 1-4.

In some embodiments provide methods of treating osteolytic lesions in a subject comprising administering to the subject in need thereof a therapeutically effective amount of a cyclohexenone compound having the structure:

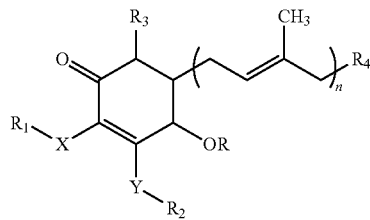

wherein each of X and Y independently is oxygen, NR$_5$ or sulfur;

R is a hydrogen or C(=O)C$_1$-C$_8$alkyl;

each of R$_1$, R$_2$ and R$_3$ independently is a hydrogen, methyl or (CH$_2$)$_m$—CH$_3$;

R$_4$ is NR$_5$R$_6$, OR$_5$, OC(=O)R$_7$, C(=O)OR$_5$, C(=O)R$_5$, C(=O)NR$_5$R$_6$, halogen, 5 or 6-membered lactone, C$_1$-C$_8$alkyl, C$_2$-C$_8$alkenyl, C$_2$-C$_8$alkynyl, aryl, glucosyl, wherein the 5 or 6-membered lactone, C$_1$-C$_8$alkyl, C$_2$-C$_8$alkenyl, C$_2$-C$_8$alkynyl, aryl, and glucosyl are optionally substituted with one or more substituents selected from NR$_5$R$_6$, OR$_5$, OC(=O)R$_7$, C(=O)OR$_5$, C(=O)R$_5$, C(=O)NR$_5$R$_6$, C$_1$-C$_8$ alkyl, C$_2$-C$_8$ alkenyl, C$_2$-C$_8$ alkynyl, C$_3$-C$_8$ cycloalkyl, and C$_1$-C$_8$ haloalkyl;

each of R$_5$ and R$_6$ is independently a hydrogen or C$_1$-C$_8$ alkyl;

R$_7$ is a C$_1$-C$_8$alkyl, OR$_5$ or NR$_5$R$_6$;

m=1-12; and n=1-12; or a pharmaceutically acceptable salt, metabolite, solvate or prodrug thereof. In some embodiments, the subject has breast cancer or prostate cancer. In some embodiments, the subject is human. See Examples 1-4.

Osteolytic lesions also called osteoclastic lesions or lytic lesions for short, are characteristic areas of damage caused by myeloma. When myeloma invades bone tissue, it causes weak areas to form. In addition, the myeloma cells release chemicals that also lead to bone breakdown. The result is lesions with a specific "punched-out" appearance that may occur in any bone in the body, but are most often noted in the spine, skull, pelvis and ribs.

Certain Pharmaceutical and Medical Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group may be a saturated alkyl group (which means that it does not contain any carbon-carbon double bonds or carbon-carbon triple bonds) or the alkyl group may be an unsaturated alkyl group (which means that it contains at least one carbon-carbon double bonds or carbon-carbon triple bond). The alkyl moiety, whether saturated or unsaturated, may be branched, or straight chain.

The "alkyl" group may have 1 to 12 carbon atoms (whenever it appears herein, a numerical range such as "1 to 12 refers to each integer in the given range; e.g., "1 to 12 carbon atoms" means that the alkyl group may consist of 1 carbon atom, 2 carbon atoms, 3 carbon atoms, etc., up to and including 12 carbon atoms, although the present definition also covers the occurrence of the term "alkyl" where no numerical range is designated). The alkyl group of the compounds described herein may be designated as "$C_1$-$C_8$alkyl" or similar designations. By way of example only, "$C_1$-$C_8$alkyl" indicates that there are one, two, three, four, five, six, seven or eight carbon atoms in the alkyl chain. In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, cyclopropylmethyl, cyclobutylmethyl, cyclopentylmethyl, cyclohexylmethyl, and the like. In one aspect, an alkyl is a $C_1$-$C_8$ alkyl.

The term "alkylene" refers to a divalent alkyl radical. Any of the above mentioned monovalent alkyl groups may be an alkylene by abstraction of a second hydrogen atom from the alkyl. In one aspect, an alkylene is a $C_1$-$C_{12}$alkylene. In another aspect, an alkylene is a $C_1$-$C_8$alkylene. Typical alkylene groups include, but are not limited to, —$CH_2$—, —CH($CH_3$)—, —C($CH_3$)$_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

As used herein, the term "aryl" refers to an aromatic ring wherein each of the atoms forming the ring is a carbon atom. Aryl rings are formed by five, six, seven, eight, nine, or more than nine carbon atoms. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group can be a monoradical or a diradical (i.e., an arylene group). In one aspect, an arylene is a $C_6$-$C_{10}$ arylene. Exemplary arylenes include, but are not limited to, phenyl-1,2-ene, phenyl-1,3-ene, and phenyl-1,4-ene.

The term "aromatic" refers to a planar ring having a delocalized π-electron system containing 4n+2π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "halo" or, alternatively, "halogen" or "halide" means fluoro, chloro, bromo or iodo.

The term "lactone" refers to a cyclic ester which can be seen as the condensation product of an alcohol group —OH and a carboxylic acid group —COOH in the same molecule. It is characterized by a closed ring consisting of two or more carbon atoms and a single oxygen atom, with a ketone group =O in one of the carbons adjacent to the other oxygen.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (=O) moieties, such as pyrrolidin-2-one.

The term "alkenyl" as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (i.e., an alkenylene group). In some embodiments, alkenyl groups are optionally substituted. Illustrative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-cecenyl.

The term "alkynyl" as used herein, means a straight, branched chain, or cyclic (in which case, it would also be known as a "cycloalkenyl") hydrocarbon containing from 2-10 carbons and containing at least one carbon-carbon triple bond formed by the removal of four hydrogens. In some embodiments, depending on the structure, an alkynyl group is a monoradical or a diradical (i.e., an alkynylene group). In some embodiments, alkynyl groups are optionally substituted. Illustrative examples of alkynyl include, but are not limited to, ethynyl, propynyl, butynyl, pentynyl, hexynyl, heptynyl, and the like.

The term "alkoxy" as used herein, means an alkyl group, as defined herein, appended to the parent molecular moiety through an oxygen atom. Illustrative examples of alkoxy include, but are not limited to, methoxy, ethoxy, propoxy, 2-propoxy, butoxy, tert-butoxy, pentyloxy, and hexyloxy.

The term "cycloalkyl" as used herein, means a monocyclic or polycyclic radical that contains only carbon and hydrogen, and includes those that are saturated, partially unsaturated, or fully unsaturated. Cycloalkyl groups include groups having from 3 to 10 ring atoms. Representative examples of cyclic include but are not limited to, the following moieties:

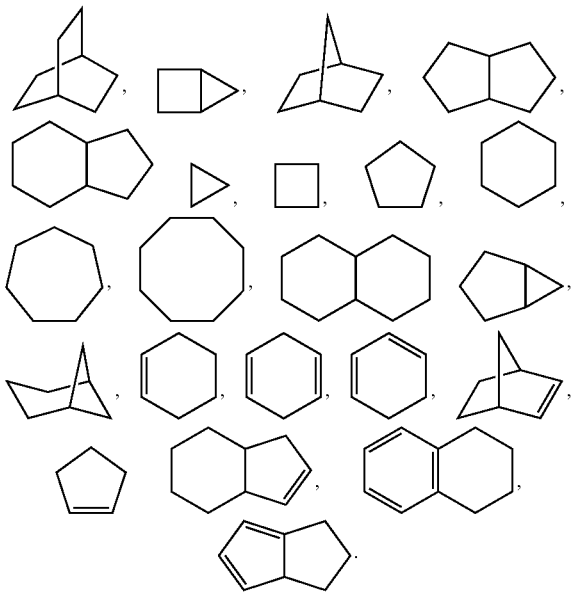

In some embodiments, depending on the structure, a cycloalkyl group is a monoradical or a diradical (e.g., a cycloalkylene group).

The terms "haloalkyl," "haloalkenyl," "haloalkynyl" and "haloalkoxy" as used herein, include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

The term "glucosyl" as used herein, include D- or L-form glucosyl groups, in which the glucosyl group is attached via any hydroxyl group on the glucose ring.

The term "acceptable" with respect to a formulation, composition or ingredient, as used herein, means having no persistent detrimental effect on the general health of the subject being treated.

*Antrodia* is a genus of fungi in the family Meripilaceae. *Antrodia* species have fruiting bodies that typically lie flat or spread out on the growing surface, with the hymenium exposed to the outside; the edges may be turned so as to form narrow brackets. Most species are found in temperate and boreal forests, and cause brown rot. Some of the species in this genus are have medicinal properties, and have been used in Taiwan as a Traditional medicine.

The term "carrier," as used herein, refers to relatively non-toxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound (i.e., a cyclohexenone compound described herein) and a co-agent, are both administered to a patient simultaneously in the form of a single entity or dosage. The term "non-fixed combination" means that the active ingredients, e.g. a compound (i.e., a cyclohexenone compound described herein) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound (i.e., a cyclohexenone compound described herein) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In some embodiments, the cyclohexenone compound, or a pharmaceutically acceptable salt, metabolite, solvate or prodrug thereof, is administered parenterally or intravenously. In other embodiments, the cyclohexenone compound, or a pharmaceutically acceptable salt, metabolite, solvate or prodrug thereof, is administered by injection. In some embodiments, the cyclohexenone compound, or a pharmaceutically acceptable salt, metabolite, solvate or prodrug thereof, is administered orally.

Pharmaceutical Composition/Formulation

In some embodiments provide compounds having the structure:

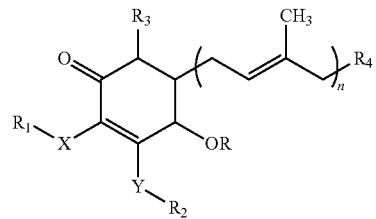

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, R is a hydrogen, $C(=O)C_3H_8$, $C(=O)C_2H_5$, or $C(=O)CH_3$. In some embodiments, each of $R_1$, $R_2$ and $R_3$ independently is a hydrogen, methyl, ethyl, propyl, butyl, pentyl hexyl, heptyl, or octyl. In certain embodiments, $R_1$ is a hydrogen or methyl. In certain embodiments, $R_2$ is a hydrogen, methyl, ethyl, propyl, butyl, pentyl or hexyl. In certain embodiments, $R_3$ is a hydrogen, methyl, ethyl, propyl, butyl, pentyl or hexyl. In some embodiments, $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)$ $CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$. In certain embodiments, $R_4$ is $C_2H_5C(CH_3)_2OH$, $C_2H_5C(CH_3)_2OCH_3$, $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, aryl, $C_1$-$C_8$ alkyl, or glucosyl, wherein 5 or 6-membered lactone, aryl, $C_1$-$C_8$ alkyl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl. In certain embodiments, $R_4$ is $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, aryl, or glucosyl, wherein the 5 or 6-membered lactone, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

In certain embodiments, the compound is selected from group consisting of

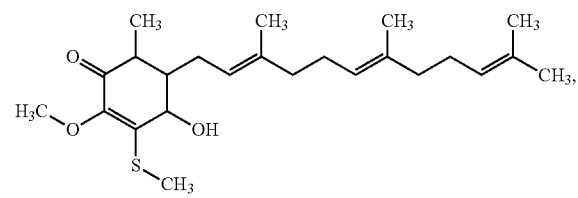
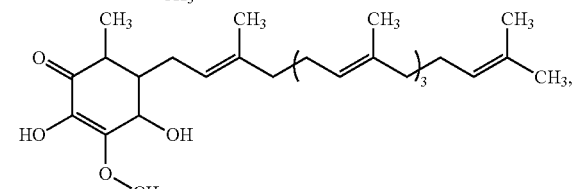
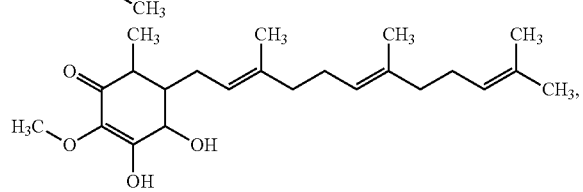
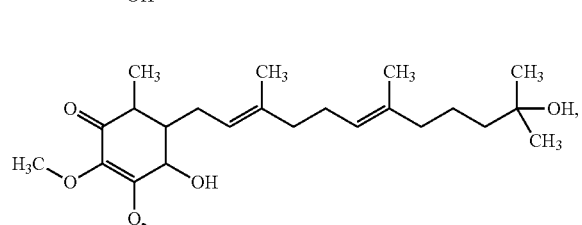
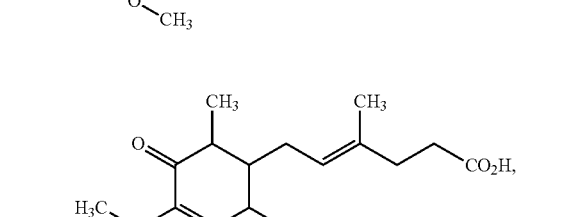
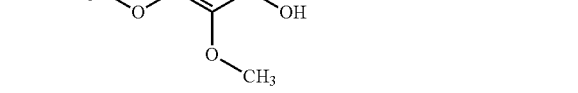
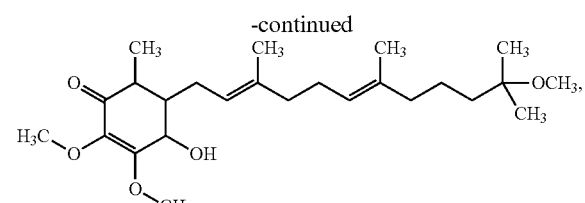
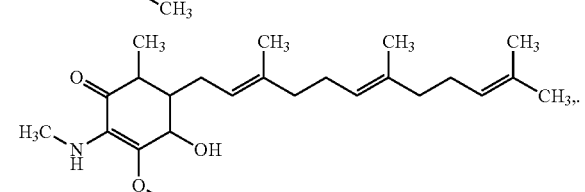
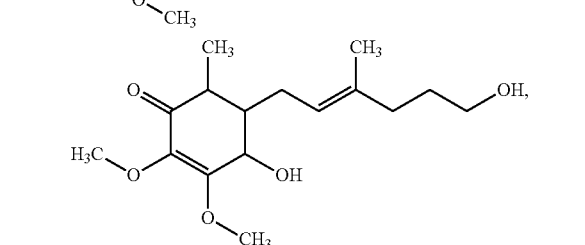
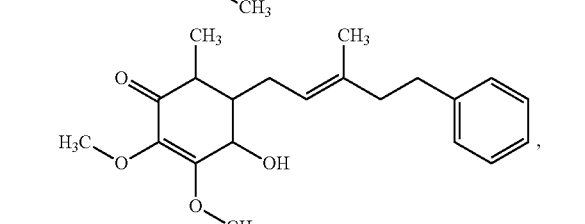
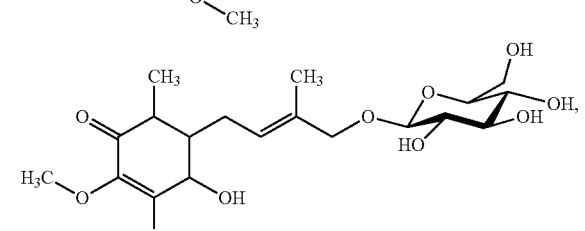
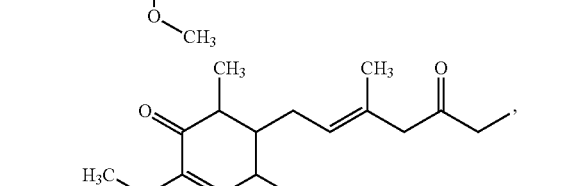
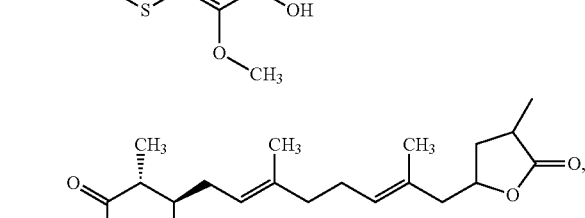
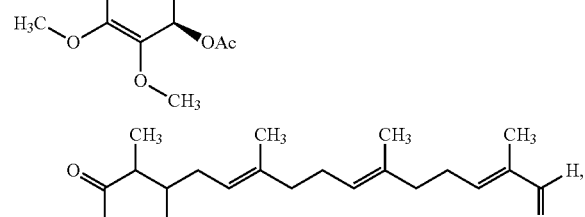

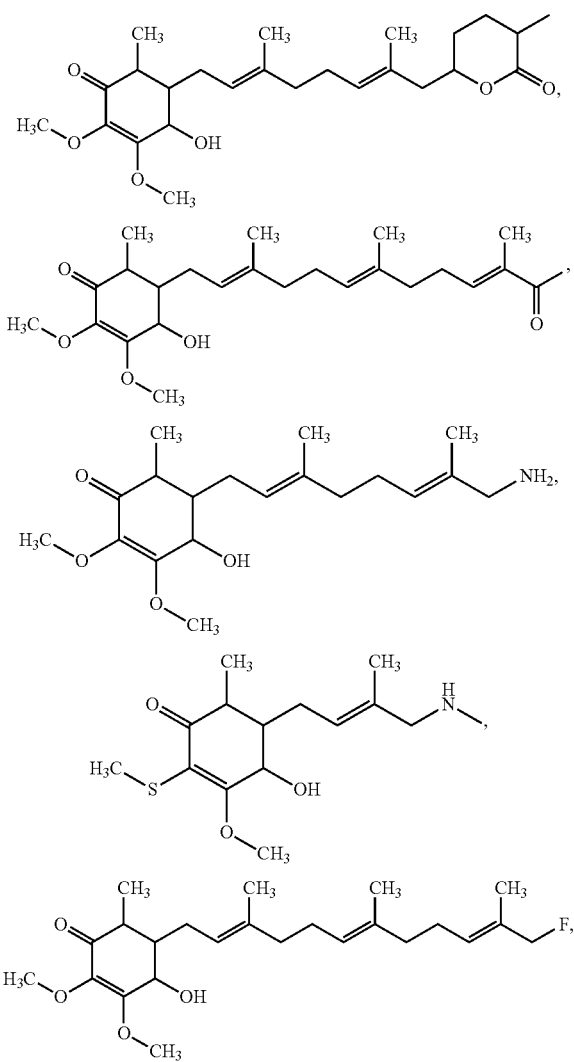
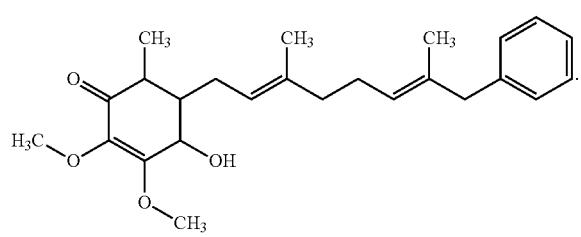
In certain embodiments, the compound is selected from group consisting of
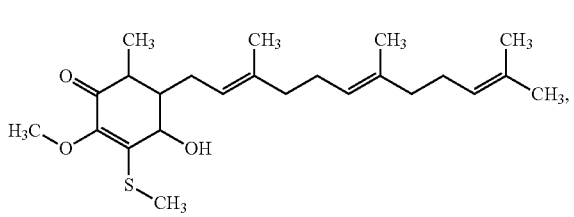
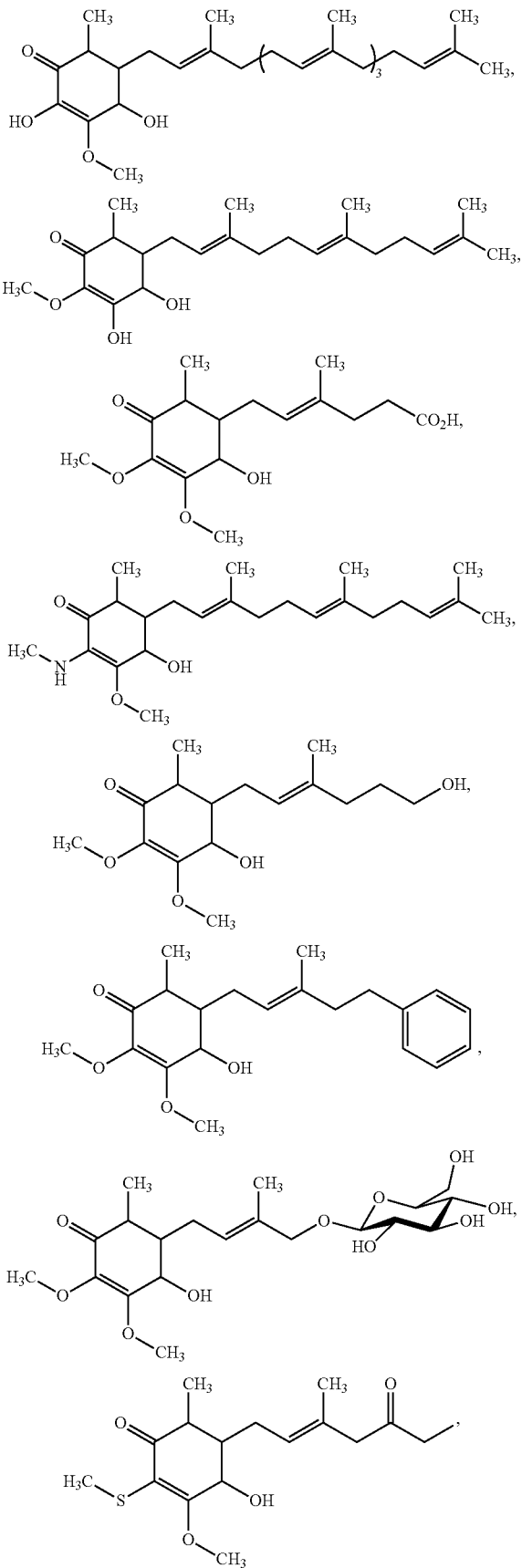

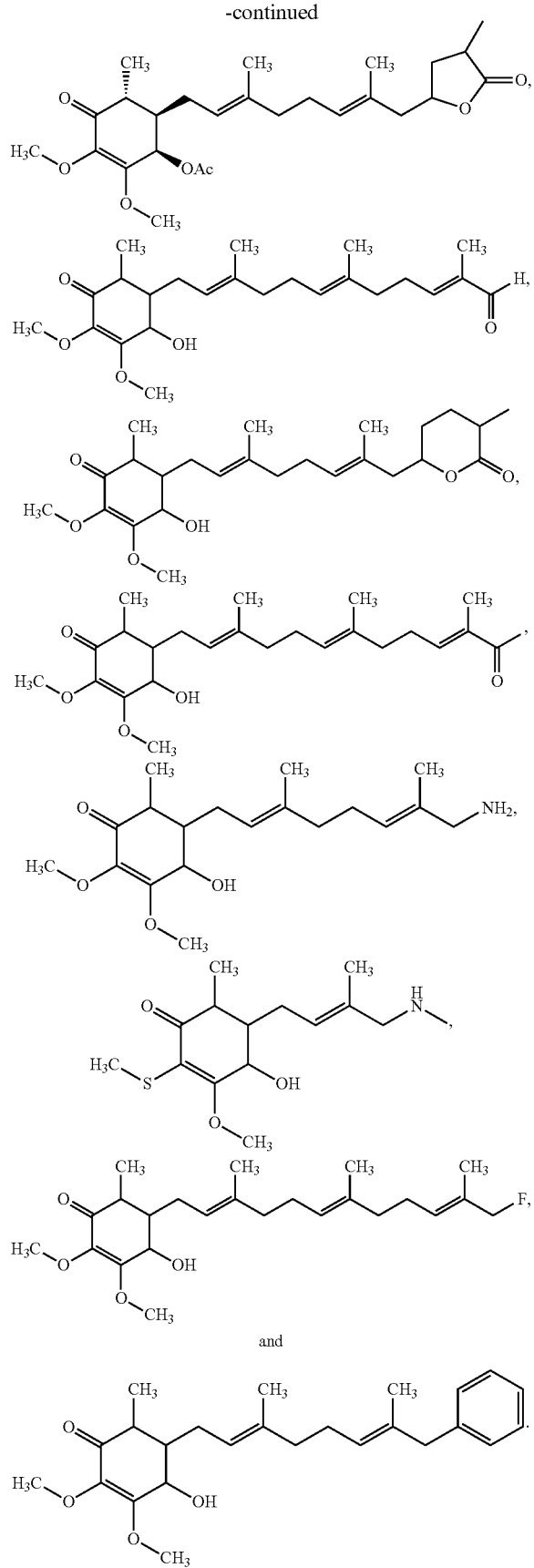

and

In some embodiments provide pharmaceutical compositions comprising a therapeutically effective amount of a cyclohexenone compound having the structure:

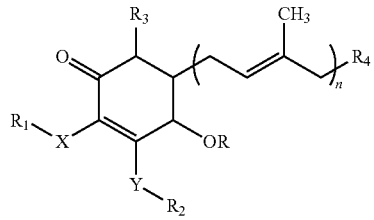

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$ alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof, and a pharmaceutically acceptable excipient.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

Provided herein are pharmaceutical compositions comprising a compound (i.e., a cyclohexenone compound described herein) and a pharmaceutically acceptable diluent(s), excipient(s), or carrier(s). In certain embodiments, the compounds described are administered as pharmaceutical compositions in which a compound (i.e., a cyclohexenone compound described herein) is mixed with other active ingredients, as in combination therapy. Encompassed herein are all combinations of actives set forth in the combination therapies section below and throughout this disclosure. In specific embodiments, the pharmaceutical compositions include one or more compounds (i.e., a cyclohexenone compound described herein).

A pharmaceutical composition, as used herein, refers to a mixture of a compound (i.e., a cyclohexenone compound described herein) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds (i.e., a cyclohexenone compound described herein) are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, a compound (i.e., a cyclohexenone compound described herein) is formulated in an aqueous solution. In specific embodiments, the aqueous solution is selected from, by way of example only, a physiologically compatible buffer, such as Hank's solution, Ringer's solution, or physiological saline buffer. In other embodiments, a compound (i.e., a cyclohexenone compound described herein) is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including a compound (i.e., a cyclohexenone compound described herein), are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions of a compound (i.e., a cyclohexenone compound described herein) are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In one aspect, compounds (i.e., cyclohexenone compounds described herein) are prepared as solutions for parenteral injection as described herein or known in the art and administered with an automatic injector. Automatic injectors, such as those disclosed in U.S. Pat. Nos. 4,031,893, 5,358,489; 5,540,664; 5,665,071, 5,695,472 and WO/2005/087297 (each of which are incorporated herein by reference for such disclosure) are known. In general, all automatic injectors contain a volume of solution that includes a compound (i.e., a cyclohexenone compound described herein) to be injected. In general, automatic injectors include a reservoir for holding the solution, which is in fluid communication with a needle for delivering the drug, as well as a mechanism for automatically deploying the needle, inserting the needle into the patient and delivering the dose into the patient. Exemplary injectors provide about 0.3 mL, 0.6 mL, 1.0 mL or other suitable volume of solution at about a concentration of 0.5 mg to 50 mg of a compound (i.e., a cyclohexenone compound described herein) per 1 mL of solution. Each injector is capable of delivering only one dose of the compound.

In still other embodiments, the compounds (i.e., cyclohexenone compounds described herein) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds (i.e., cyclohexenone compounds described herein) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound (i.e., a cyclohexenone compound described herein) is accomplished by means of iontophoretic patches and the like. In certain embodiments, transdermal patches provide controlled delivery of a compound (i.e., a cyclohexenone compound described herein). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound (i.e., a cyclohexenone compound described herein); (2) a penetration enhancer; and (3) an aqueous adjuvant. In addition, transdermal formulations can include additional components such as, but not limited to, gelling agents, creams and ointment bases, and the like. In some embodiments, the transdermal formulations further include a woven or non-woven backing material to enhance absorption and prevent the removal of the transdermal formulation from the skin. In other embodiments, the transdermal formulations described herein maintain a saturated or supersaturated state to promote diffusion into the skin.

In other embodiments, the compounds (i.e., cyclohexenone compounds described herein) are formulated for administration by inhalation. Various forms suitable for administration by inhalation include, but are not limited to, aerosols, mists or powders. Pharmaceutical compositions of a compound (i.e., a cyclohexenone compound described herein) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatins for use in an inhaler or insufflator are formulated containing a powder mix of the compound and a suitable powder base such as lactose or starch.

Intranasal formulations are known in the art and are described in, for example, U.S. Pat. Nos. 4,476,116, 5,116,817 and 6,391,452, each of which is specifically incorporated herein by reference. Formulations, which include a compound (i.e., a cyclohexenone compound described herein), which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are found in sources such as REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein, may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

In still other embodiments, the compounds (i.e., cyclohexenone compounds described herein) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients is optionally used as suitable and as understood in the art. Pharmaceutical compositions comprising a compound (i.e., a cyclohexenone compound described herein) may be manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound (i.e., cyclohexenone compounds described herein) described herein as an active ingredient. The active ingredient is in free-acid or free-base form, or in a pharmaceutically acceptable salt form. In addition, the methods and pharmaceutical compositions described herein include the use crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least compound (i.e., cyclohexenone compounds described herein) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, pharmaceutical aqueous suspensions include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally include solubilizing agents to aid in the solubility of a compound (i.e., cyclohexenone compounds described herein). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions may include one or more antioxidants to enhance chemical stability where required. Suitable antioxidants include, by way of example only, ascorbic acid and sodium metabisulfite.

In certain embodiments, pharmaceutical aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few hours up to over 24 hours. Depending on the chemical nature and the biological stability of the therapeutic reagent, additional strategies for protein stabilization may be employed.

In certain embodiments, the formulations described herein include one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Combination Treatments

In general, the compositions described herein and, in embodiments where combinational therapy is employed, other agents do not have to be administered in the same pharmaceutical composition, and in some embodiments, because of different physical and chemical characteristics, are administered by different routes. In some embodiments, the initial administration is made according to established protocols, and then, based upon the observed effects, the dosage, modes of administration and times of administration is modified by the skilled clinician.

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein.

Combinations of compounds (i.e., the cyclohexenone compound described herein) with other anti-cancer agents are intended to be covered. In some embodiments, examples of anti-cancer agents include, but are not limited to, the following: cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, other topoisomerase inhibitors (e.g., irinotecan, topotecan, camptothecin, etc.) or any derivative related agent of the foregoing.

The combinations of the cyclohexenone compounds and other anti-cancer agents described herein encompass additional therapies and treatment regimens with other agents in some embodiments. Such additional therapies and treatment regimens can include another anti-cancer therapy in some embodiments. Alternatively, in other embodiments, additional therapies and treatment regimens include other agents used to treat adjunct conditions associated with the cancer or a side effect from such agent in the combination therapy. In further embodiments, adjuvants or enhancers are administered with a combination therapy described herein.

Additional anti-cancer therapies include chemotherapy, radiotherapy, immunotherapy, gene therapy, surgery or other therapies that are capable of negatively affecting cancer in a patient, such as for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

In some embodiments provide compositions for treating a disease or condition associated with bone metastasis comprising a therapeutically effective amount of a cyclohexenone compound having the structure:

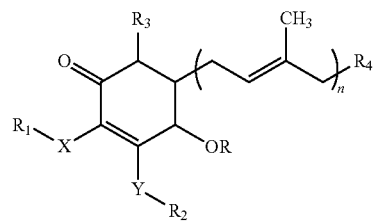

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
each of $R_5$ and $R_6$ is independently a hydrogen or $C_1$-$C_8$ alkyl;
$R_7$ is a $C_1$-$C_8$alkyl, $OR_5$ or $NR_5R_6$;
m=1-12; and n=1-12; or a pharmaceutically acceptable salt, metabolite, solvate or prodrug thereof, and one or more anti-cancer agents.

EXAMPLES

Example 1

Preparation of the Exemplary Cyclohexenone Compounds

One hundred grams of mycelia, fruiting bodies or mixture of both from *Antrodia camphorata* were placed into a flask. A proper amount of water and alcohol (70-100% alcohol solution) was added into the flask and were stirred at 20-25° C. for at least 1 hour. The solution was filtered through a filter and 0.45 μm membrane and the filtrate was collected as the extract.

The filtrate of *Antrodia camphorata* was subjected to High Performance Liquid chromatography (HPLC) analysis. The separation was performed on a RP18 column, the mobile phase consisted of methanol (A) and 0.3% acetic acid (B), with the gradient conditions of 0-10 min in 95%-20% B, 10-20 min in 20%-10% B, 20-35 min in 10%-10% B, 35-40 min in 10%-95% B, at the flow rate of 1 ml/min. The column effluent was monitored with a UV-visible detector.

The fractions collected at 21.2 to 21.4 min were collected and concentrated to yield compound 5, a product of pale yellow liquid. Compound 5 was analyzed to be 4-hydroxy-5-(11-hydroxy-3,7,11-trimethyldodeca-2,6-dienyl)-2,3-dimethoxy-6-methylcyclohex-2-enone with molecular weight of 408 (Molecular formula: $C_{24}H_{40}O_5$). $^1$H-NMR (CDCl$_3$) δ (ppm)=1.21, 1.36, 1.67, 1.71, 1.75, 1.94, 2.03, 2.07, 2.22, 2.25, 3.68, 4.05, 5.71 and 5.56. $^{13}$C-NMR (CDCl$_3$) δ (ppm): 12.31, 16.1, 16.12, 17.67, 25.67, 26.44, 26.74, 27.00, 30.10, 40.27, 43.34, 59.22, 60.59, 71.8, 120.97, 123.84, 124.30, 131.32, 134.61, 135.92, 138.05, 160.45, and 197.11.

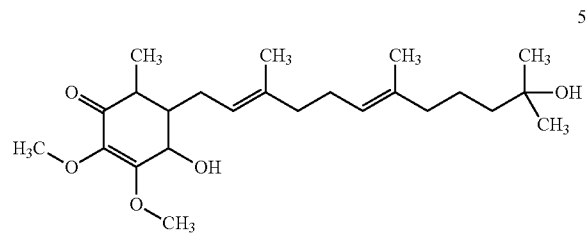 [SMILES: COC1=C(OC)C(O)C(C/C=C(\C)CC/C=C(\C)CCCC(C)(C)O)C(C)C1=O]

Compound 5: 4-hydroxy-5-(11-hydroxy-3,7,11-trimethyldodeca-2,6-dienyl)-2,3-dimethoxy-6-methylcyclohex-2-enone The fractions collected at 23.7 to 24.0 min were collected and concentrated to yield compound 7, a product of pale yellow liquid. Compound 7 was analyzed to be 4-hydroxy-2,3-dimethoxy-5-(11-methoxy-3,7,11-trimethyldodeca-2,6-dienyl)-6-methylcyclohex-2-enone with molecular weight of 422 ($C_{25}H_{42}O_5$). $^1$H-NMR (CDCl$_3$) δ (ppm)=1.21, 1.36, 1.71, 1.75, 1.94, 2.03, 2.07, 2.22, 2.25, 3.24, 3.68, 4.05, 5.12, 5.50, and 5.61. $^{13}$C-NMR (CDCl$_3$) δ (ppm): 12.31, 16.1, 16.12, 17.67, 24.44, 26.44, 26.74, 27.00, 37.81, 39.81, 40.27, 43.34, 49.00, 59.22, 60.59, 120.97, 123.84, 124.30, 135.92, 138.05, 160.45 and 197.12.

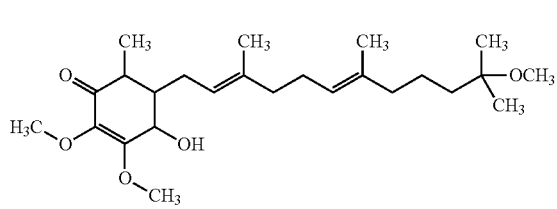

Compound 7: 4-hydroxy-2,3-dimethoxy-5-(11-methoxy-3,7,11-trimethyldodeca-2,6-dienyl)-6-methylcyclohex-2-enone The fractions collected at 25 to 30 min were collected and concentrated to yield 4-hydroxy-2,3-dimethoxy-6-methyl-5-(3,7,11-trimethyldodeca-2,6,10-trienyl)cyclohex-2-enone (compound 1), a product of pale yellow brown liquid. The analysis of compound 1 showed the molecular formula of $C_{24}H_{38}O_4$, molecular weight of 390 with melting point of 48 to 52° C. NMR spectra showed that $^1$H-NMR (CDCl$_3$) δ (ppm)=1.51, 1.67, 1.71, 1.75, 1.94, 2.03, 2.07, 2.22, 2.25, 3.68, 4.05, 5.07, and 5.14; $^{13}$C-NMR (CDCl$_3$) δ (ppm)=12.31, 16.1, 16.12, 17.67, 25.67, 26.44, 26.74, 27.00, 39.71, 39.81, 40.27, 43.34, 59.22, 60.59, 120.97, 123.84, 124.30, 131.32, 135.35, 135.92, 138.05, 160.45, and 197.12.

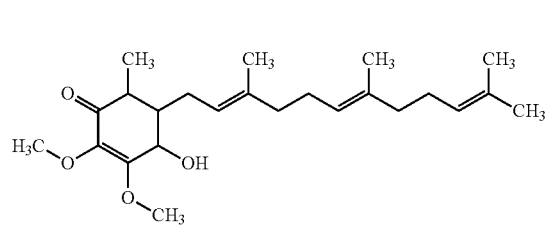

Compound 1: 4-hydroxy-2,3-dimethoxy-6-methyl-5-(3,7,11-trimethyldodeca-2,6,10-trienyl)cyclohex-2-enone Compound 6, a metabolite of compound 1, was obtained from urine samples of rats fed with Compound 1 in the animal study. Compound 6 was determined to be 4-hydroxy-2,3-dimethoxy-6-methyl-5-(3-methyl-2-hexenoic acid)cyclohex-2-enone with molecular weight of 312 ($C_{16}H_{24}O_6$). Compound 4 which was determined as 3,4-dihydroxy-2-methoxy-6-methyl-5-(3,7,11-trimethyldodeca-2,6,10-trienyl)cyclohex-2-enone (molecular weight of 376, $C_{23}H_{36}O_4$), was obtained when compound 1 was under the condition of above 40° C. for 6 hours.

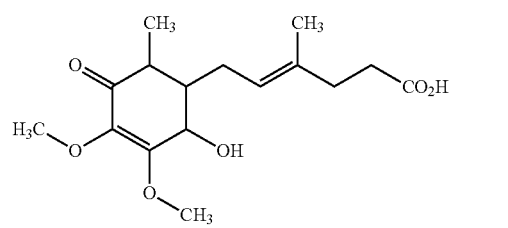

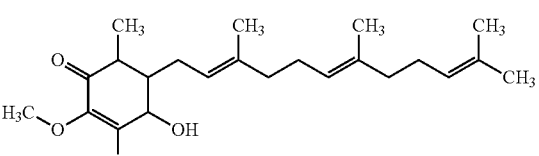

Alternatively, the exemplary compounds may be prepared from 4-hydroxy-2,3-dimethoxy-6-methylcyclohexa-2,5-dienone, or the like. Similarly, other cyclohexenone compounds having the structure

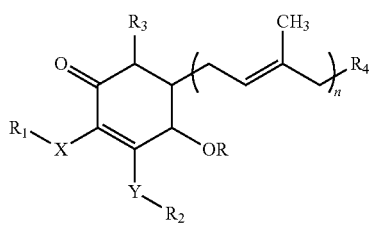

are isolated from *Antrodia camphorata* or prepared synthetically or semi-synthetically from the suitable starting materials. An ordinary skilled in the art would readily utilize appropriate conditions for such synthesis.

Example 2

The Effects of Compound 1 in a Breast Cancer Bone Metastasis Model

Patients with breast cancer typically develop metastases to bone. Almost all breast cancer patients with end-stage disease have bone metastases. Bone metastases caused by breast cancer are osteolytic, causing severe bone loss that leads to highly increased risk of fractures. Although the primary tumor could be successfully removed, the disease may have already spread to bone. In this case, the disease can develop further visceral and bone metastases. Currently, there is no efficient cure for prevention or treatment of bone metastases.

The objective of this study was to test the efficacy of three different doses of the exemplary compound 1 (Antroquinonol) from Example 1 on breast cancer bone metastases in female athymic nude mice in a 25-day study in preventive setting. The following 5 experimental groups were included in the study:
1. Control group receiving vehicle (po twice a day)
2. Reference group receiving zoledronic acid (sc at days 1 and 14)+vehicle (po twice a day)
3. Test group receiving 15 mg/kg of test compound (po twice a day)
4. Test group receiving 30 mg/kg of test compound (po twice a day)
5. Test group receiving 45 mg/kg of test compound (po twice a day)

The vehicle was corn oil. All groups included 15 mice that are 5 weeks of age at the beginning of the study. Based on the body weights the animals were randomized to five groups. On day 0, the animals were given intracardiac inoculation of human breast cancer cells. Body weights were determined twice a week. At sacrifice, the osteolytic lesions and whole body tumor burden were quantified by x-ray and fluorescence imaging, respectively. The test compound and vehicle were administered by oral gavage twice a day. Blood samples for analysing TRACP 5b were collected at days 0, 17 and 24. The animals were sacrificed at day 25, or earlier if they became moribund. Tissue samples were collected for histology and embedded in paraffin from left and right tibia and femur for possible future histomorphometric analyses. Gross necropsy was performed to all animals at the end of the study, and all macroscopic signs were recorded.

Materials and Equipment
Test Compound

Test compound 1 (99%, 1005 mg/ml) was obtained in liquid form. Three 50× stock solutions were prepared in corn oil (75 mg/ml, 150 mg/ml and 225 mg/ml) and stored them in dark at +4° C. The dosing solutions of 1.5, 3.0 and 4.5 mg/ml were prepared from the stock solutions by diluting the stock solutions in corn oil 1:50. The dosing solutions were prepared once a week and stored in dark at +4° C. The dosing volume was 10 ml/kg. The test compound was administered by oral gavage twice a day with dosing intervals of 10+14 hours. The dosings were performed at the same time every day.

Reference Compound

Zoledronic acid was used as a reference compound. 100 μl of Zometa® (Novartis Pharma GmbH, Nürnberg, Germany) 4 mg/5 ml infusion concentrate was diluted in 3.9 ml of sterile saline (0.9% NaCl) to obtain the administration concentration of 0.02 mg/ml. This solution was prepared once during the study and stored at +4° C. The dosing volume was 5 ml/kg, resulting in the dose of 0.1 mg/kg. The reference compound was administered SC twice in the study: at days 1 and 14.

Vehicle

The vehicle was corn oil (Sigma-Aldrich).

Primary Materials, Animals and Primary Equipment

Female athymic nude mice (Hsd: Athymic nude-nu) were obtained from Harlan Laboratories B.V. (Horst, The Netherlands). MDA-MB-231SA-GFP6 human breast cancer cells were received originally from Prof. Theresa Guise (Indiana University, Indianapolis, Ind., USA) and transfected with pTurboGFP-N vector (Evrogen JSC, Moscow, Russia).

Description of the Test System Used

This experiment utilized an animal model that closely resembles the characteristics of breast cancer metastatic disease or condition in humans. This model can be effectively used for testing the effects of cancer drug candidates on the metastasis of breast cancer cells to bone. In this model, human breast cancer cells are inoculated into the left cardiac ventricle of 5 weeks old female athymic nude mice. This mouse strain is immunodeficient, allowing rapid spreading of the human cancer cells. Within two weeks after the inoculation, the animals develop osteolytic bone metastases that can be visualized by X-ray radiography. In addition, soft tissue metastases are observed in approximately 40% of the animals, especially in adrenal glands. At 3 weeks, the bone metastases are clearly visible in X-ray radiographs and the animals have developed cachexia and lost weight substantially. The animals are sacrificed typically at 3-4 weeks after inoculation, and their hindlegs are collected for further histomorphometric analysis.

The bone metastasis animal model provided herein can be conveniently used to test drug candidates that have been shown in preliminary studies to affect one or more of the following: 1) growth of cancer cells; 2) invasion of cancer cells; 3) migration of cancer cells; 4) angiogenesis; 5) function or differentiation of osteoclasts. The model can also be used for finding new indications to existing drugs, allowing the pharmaceutical companies a way of finding new indications to patented drugs that have already proved efficient in some other indications.

Procedures
Animal Handling and Cell Culture

Female Athymic nude mice (Hsd: Athymic nude-nu, obtained from Harlan, The Netherlands) were used for this study. The age of the animals was 5 weeks, and their body weights were approximately 16-22 g at the beginning of the study. The mice were specific pathogen free (SPF) and isolator-reared animals. Correct age and good clinical health were qualifications for the study. The quarantine and acclimatization period for the mice was one week. Allocation to groups was performed by randomization procedure based on body weight. The animals were marked with ear marks. The mice were housed in Scantainer®, 5 mice per cage. For intracardiac inoculations and imaging, the mice were anesthetized with ip injections of Xylazin (4-5 mg/ml) and Ketamine (75-92 mg/ml). Analgesia (buprenorphine 3 mg/kg po in drinking water) was used for the last 5 days of the study.

MDA-MB-231SA-GFP6 human breast cancer cells ($10^5$ cells in 0.1 ml of PBS) were inoculated into the left cardiac ventricle of the mice at day 0, leading to development of bone metastases typical to the disease.

Animal Monitoring

The animals were weighed twice a week and doses were adjusted accordingly. For the last 5 days of the study, the animals were weighed and observed daily to monitor the progression of disease. Appearance of any clinical signs was recorded on follow-up forms. Analgesic was given to all animals for the last 5 days of the experiment.

10 animals were found dead or had to be euthanized due to breathing difficulties (see Table 1). At necropsy, punctured esophagus and oil in thoracic cavity was found. One animal was euthanized due to paraplegia before day 22 (see Table 1) 15 animals had to be euthanized between days 22 and 24 of the experiment (see Table 1). They were weighed and radiographed, and bone samples were prepared.

Two animals were removed from the final analysis due to excessive growth of cancer cells in lungs and thoracic cavity, indicating an unsuccessful inoculation of cancer cells (see Table 1).

One animal in control group was removed because it had no observable bone lesions (cut-off limit 0.5 mm$^2$). Proportionally, one animal from groups 2 and 4 with no observable bone lesions was removed from analysis (see Table 1). There were no animals under the cut-off limit in groups 3 and 5.

mals were imaged in prone and supine positions and the GFP fluorescent area (an average of the two pictures) was determined from the images with MetaMorph image analysis software.

Sacrifice, Autopsy and Sample Collection

At the end of the study (at days 22-25), the animals were weighed and sacrificed with cervical dislocation under anesthesia. Necropsy was carried out in all animals. Macroscopic findings were recorded on the follow-up forms. Ex vivo tissue samples from hind limbs (left and right tibiae and femur) were collected for possible histomorphometric analysis in future. The bone samples were fixed in 10% neutral-buffered formalin for 2-3 days, then decalcified in 10% EDTA for two weeks, and finally processed with conventional paraffin technique for histological analyses.

Statistical Analysis

Statistical analysis was performed with SPSS (version 15.0). The mean and standard deviation of each parameter were determined. One animal in control group with no observable bone lesions (cut-off limit 0.5 mm$^2$) was removed from the analysis. Proportionally, one animal from groups 2 and 4 with no observable bone lesions was removed from analysis. There were no animals under the cut-off limit in groups 3 and 5. All statistical analyses were performed as two-sided tests. Normal distribution of residuals and homogeneity of variance were checked before further analyses. In case of violating these assumptions, either log transformation or other appropriate transformation (e.g. square root, reciprocal) was applied. If the assumptions were fulfilled as such or after transformation, one-way ANOVA was used to study if

TABLE 1

The results of animal monitoring - Final N (final number of sample) with breast cancer cells.

| Group | Animal numbers | Treatment | Final N | Dead animals removed from study (id) | Time of death (study day) | Notes |
|---|---|---|---|---|---|---|
| 1 | 1-15 | Control | 15 | 9 | 25 | No observable bone lesions. |
| 2 | 1-15 | Zoledronic acid | 9 | 1 | 25 | No observable bone lesions. |
| | | | | 5 | 15 | Esophageal pundture. |
| | | | | 8 | 25 | Lung metastasis. |
| | | | | 9 | 25 | Lung metastasis. |
| | | | | 11 | 15 | Esophageal pundture. |
| | | | | 12 | 19 | Esophageal pundture. |
| 3 | 1-15 | Compound 1 30 mg/kg/d | 14 | 6 | 19 | Esophageal pundture. |
| 4 | 1-15 | Compound 1 60 mg/kg/d | 12 | 3 | 25 | No observable bone lesions. |
| | | | | 9 | 21 | Paraplegic, euthanized before d 22. |
| | | | | 11 | 9 | Esophageal pundture. |
| 5 | 1-15 | Compound 1 90 mg/kg/d | 10 | 2 | 13 | Esophageal pundture. |
| | | | | 3 | 14 | Esophageal pundture. |
| | | | | 5 | 13 | Esophageal pundture. |
| | | | | 8 | 13 | Esophageal pundture. |
| | | | | 13 | 15 | Esophageal pundture. |

Blood Sampling and Bone Marker Analyses

Blood samples for analyzing tartrate-resistant acid phosphatase isoform 5b (TRACP 5b) were collected from saphenous vein before the inoculation of cancer cells and at days 14 and 24. The serum samples were collected to 100 µl serum gel tubes, prepared within one hour from sampling, divided to two aliquots and stored at −70° C. Serum TRACP 5b was analyzed using MouseTRAP™ kit (IDS Ltd, Boldon, UK).

Fluorescent Imaging and X-Ray Radiography

Metastases were monitored by imaging the fluorescence emitted by the MDA-MB-231SA-GFP6 cells using the LT 9 GFP-imaging system LT-MACIMSYSPLUSC (Lightools Research, Encinitas, USA). The used excitation wavelength was 470/40 nm and emission wavelength 515 nm. The anithe values obtained between groups are statistically different (with p<0.05). If differences were found, Dunnett's t-test was used for comparison against the control group. If the assumptions were not fulfilled even after the transformations described above, rank-transformation was applied and the non-parametric Kruskal-Wallis followed by Mann-Whitney U-test was used. Fisher's Exact test was used for frequency data.

Deviations from the Original Study Protocol

The following deviations from the original protocol were performed during the study:

Deviation 1: At the intracardial inoculation the animals were anesthetized with Xylazin (4-5 mg/ml) and Ketamine (75-92 mg/ml) ip instead of isoflurane due to malfunction of the isoflurane vaporizer. This change does not affect the results of this study.

Deviation 2: Animals 11-15 in group 2 received one dose of Compound 1 (15 mg/kg) at study day 8 due to human error. The results of these animals were compared to the rest of group 2, and since they did not differ, these animals were not excluded from the group.

Results

Body Weight

Figure 1B:
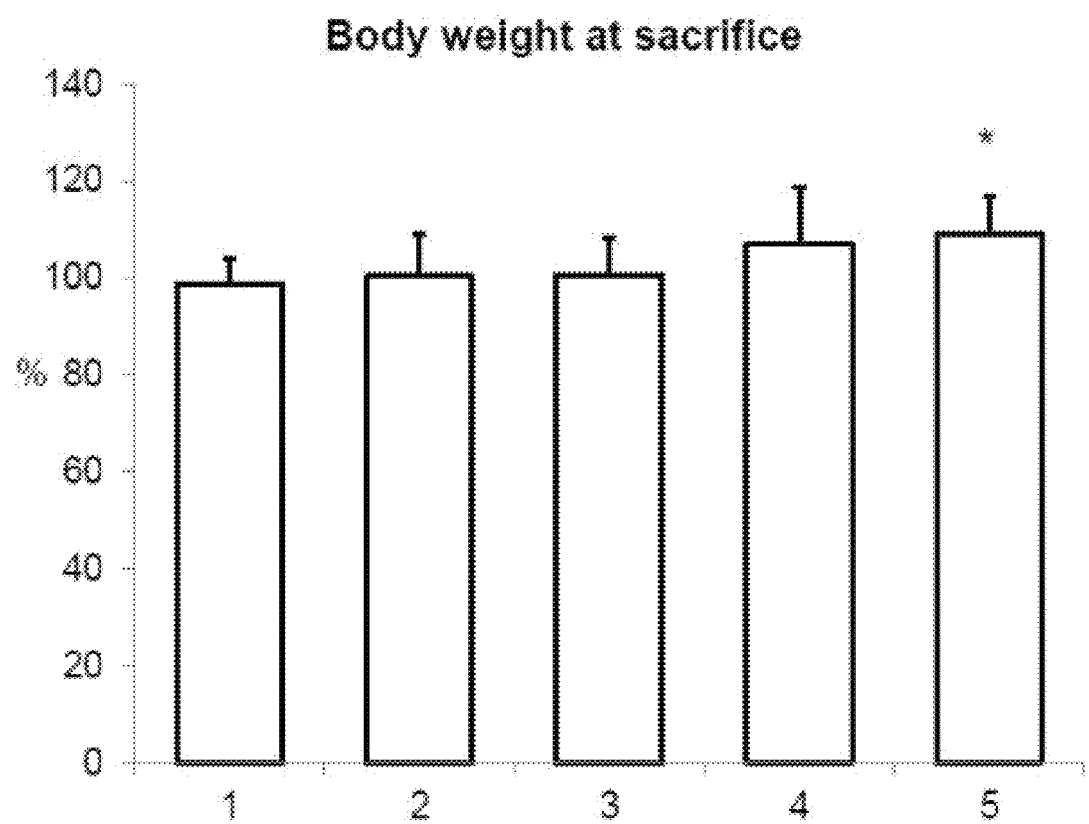
Figure 2:
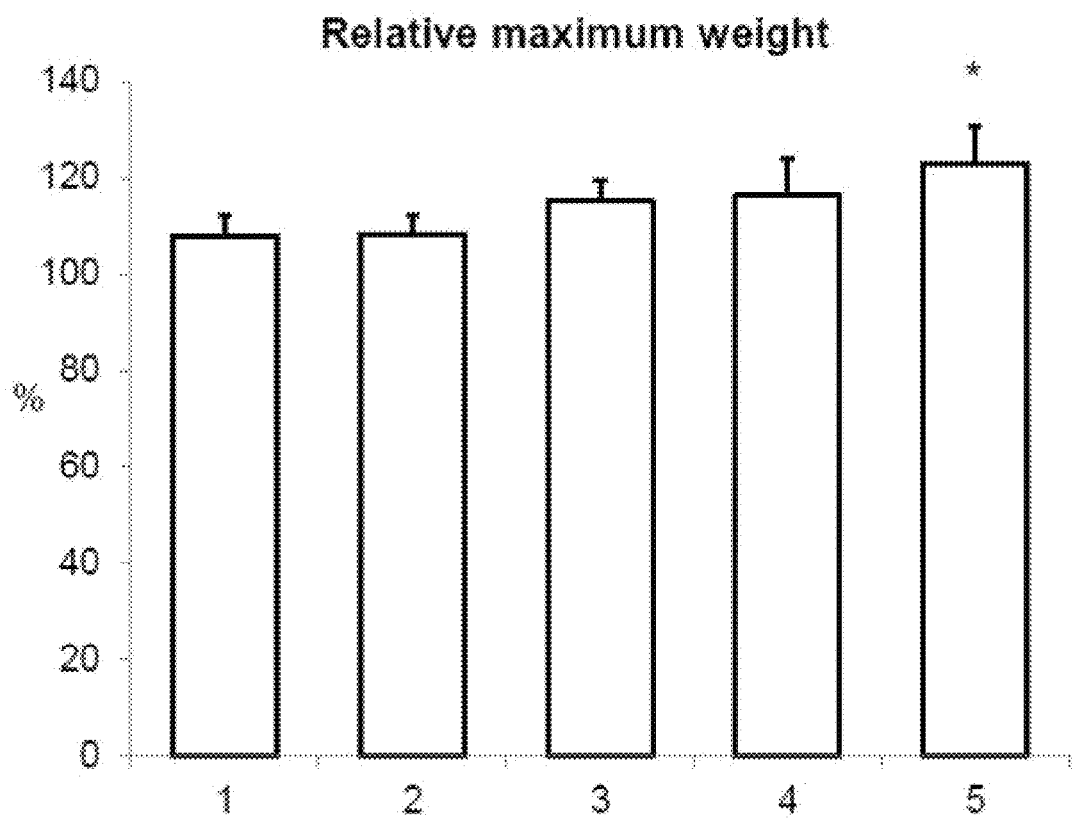
FIG. 2 shows maximum body weight obtained during the study (relative change from day 0, mean±SD). Statistical analysis was performed using One way ANOVA with logarithmic transformation followed by Dunnett's-test for comparison against the control group. One asterisk (*) indicates a statistically significant difference with a p-value<0.05 and letter "a" indicates a trend with p-value<0.1. Group 5 obtained more weight during the study.

FIG. 1a shows relative change (%) in body weight during the study (mean±SD) of Groups 1-5. In addition, body weight at sacrifice, maximum bodyweight and weight loss from maximum body weight were statistically analyzed and the results are shown in FIGS. 1b, 2 and 2b (not shown), respectively. The rise in mean body weight of control group at day 25 is due to euthanasia of moribund animals at day 24. Group 1 received vehicle (corn oil) 20 ml/kg/d po; group 2 received vehicle 20 ml/kg/d po and zoledronic acid 0.1 mg/kg sc at days 1 and 14; groups 3, 4 and received Compound 1 doses 30, 60 and 90 mg/kg/d po, respectively. In FIG. 2, Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Paraplegia and Cachexia

Animals with loss of function in any limb were considered paraplegic. Animals were considered cachectic when 2 out of 3 conditions were met: curved spine, dehydration and/or a 20% or more reduction from the maximum weight. Statistical analysis was performed using Fischer Exact test. Statistically significant differences were not observed.

Groups: Group 1 received vehicle (corn oil) 20 ml/kg/d po; group 2 received vehicle ml/kg/d po and zoledronic acid 0.1 mg/kg sc at days 1 and 14; groups 3, 4 and 5 received Compound 1 doses 30, 60 and 90 mg/kg/d po, respectively.

TABLE 2

Proportion of paraplegic and cachectic animals.

|  | Control | Zoledronic acid | Compound 1 30 mg/kg/d | Compound 1 60 mg/kg/d | Compound 1 90 mg/kg/d |
|---|---|---|---|---|---|
| Cachectic % | 21.4 | 11.1 | 21.4 | 16.7 | 20 |
| p-value |  | 1.000 | 1.000 | 1.000 | 1.000 |
| Significance |  | NS | NS | NS | NS |
| Paraplegic % | 28.6 | 22.2 | 57.1 | 8.3 | 20.0 |
| p-value |  | 1.000 | 0.252 | 0.330 | 1.000 |
| Significance |  | NS | NS | NS | NS |

Radiographic Analysis

Figure 3A:
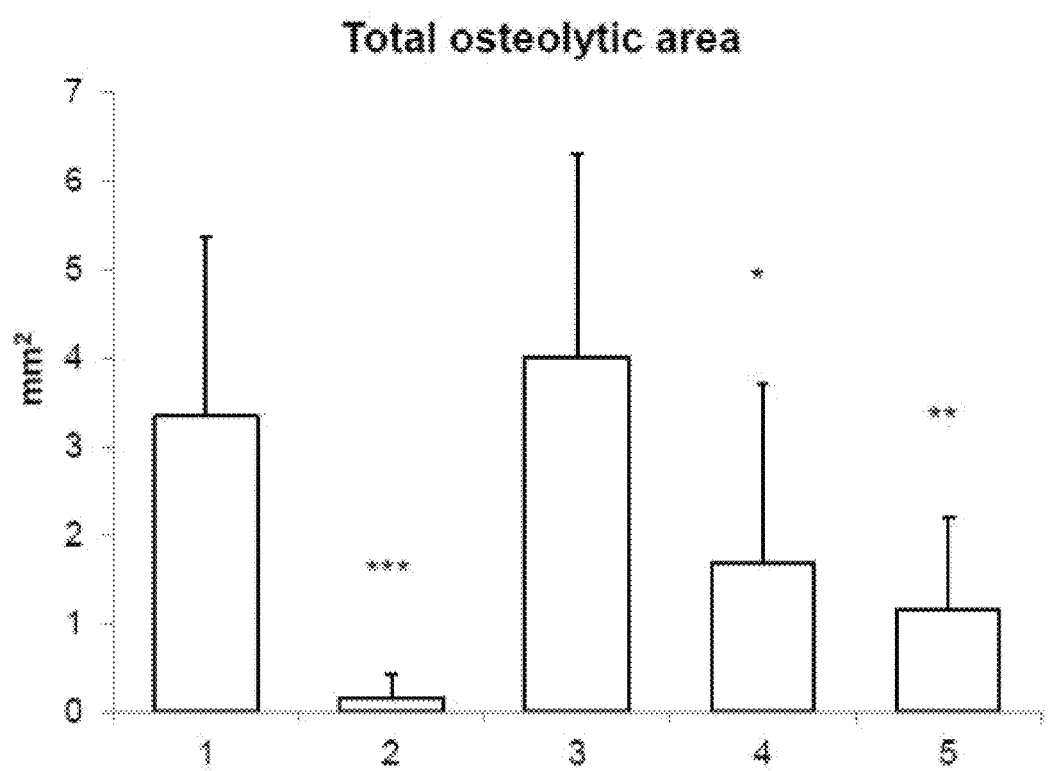
FIGS. 3a, 3b and 3c show illustrative results of total osteolytic lesion area ($mm^2$) at sacrifice (mean±SD) of Groups 1-5; mean osteolytic lesion area ($mm^2$) at sacrifice (mean±SD); and number of osteolytic lesions at sacrifice (mean±SD), respectively.
Figure 3B:
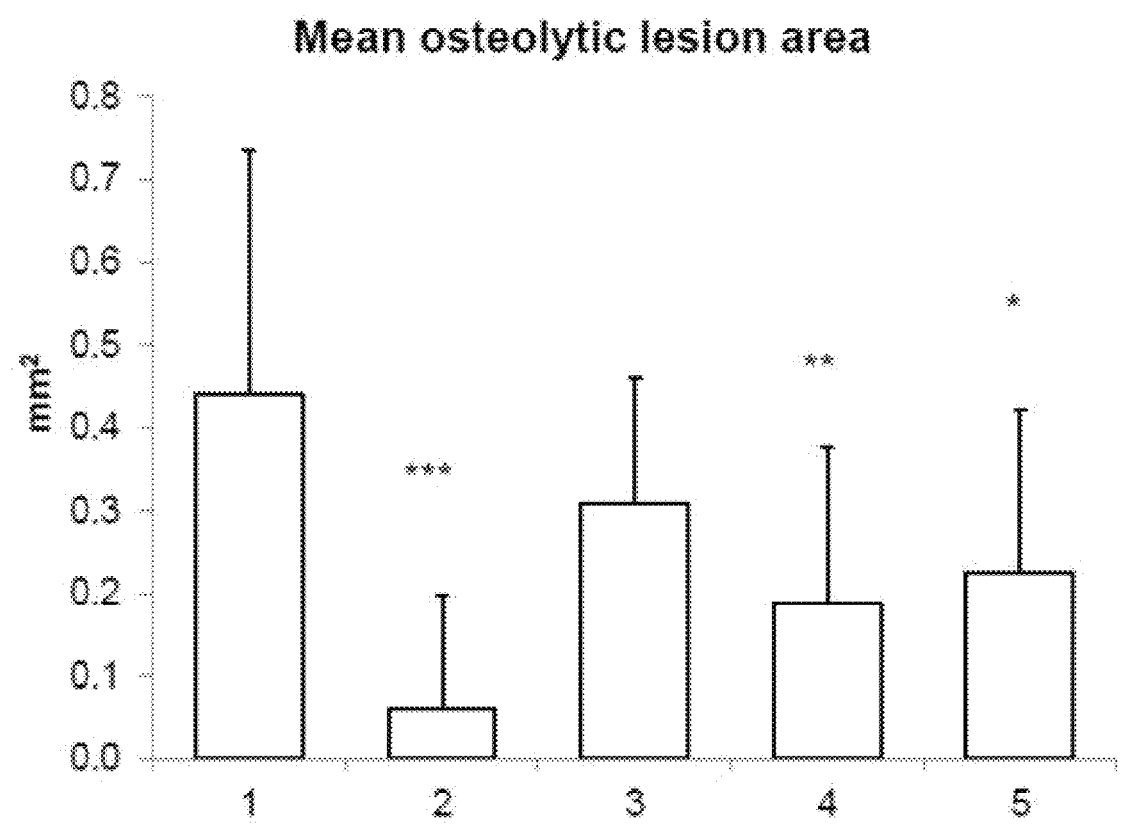
Figure 3C:
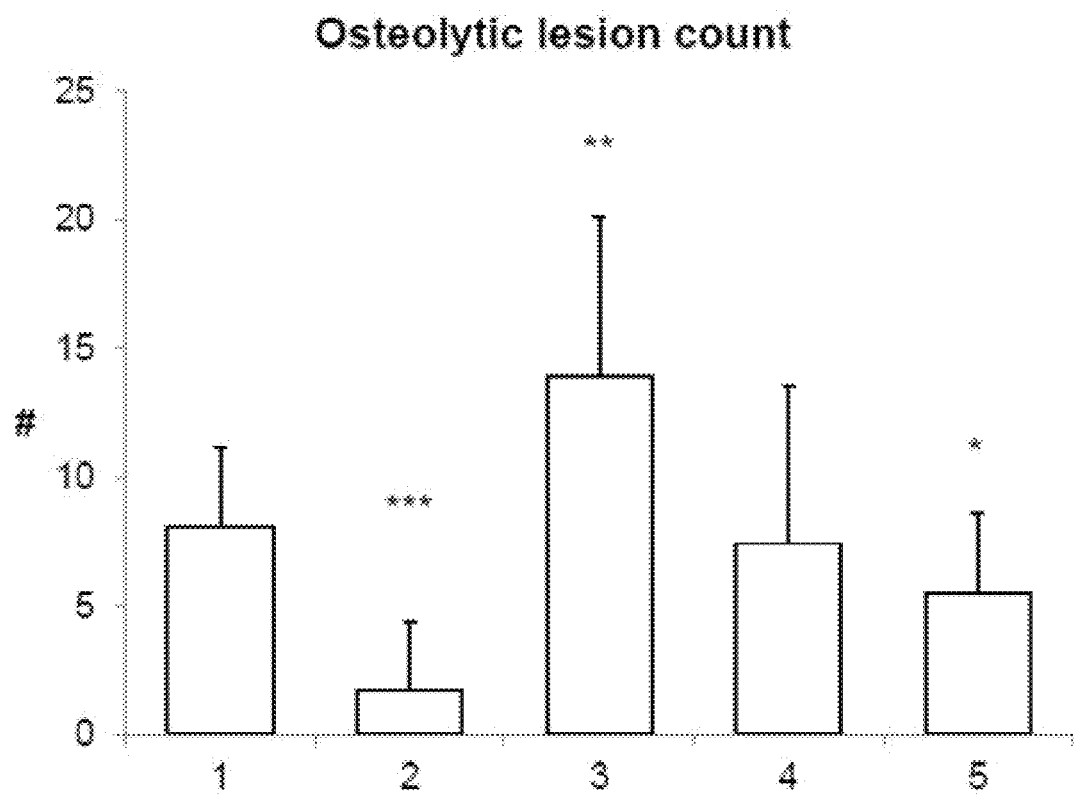

FIG. 3a shows total osteolytic lesion area (mm$^2$) at sacrifice (mean±SD) of Groups 1-5. Osteolysis was inhibited in groups 2, 4 and 5. FIG. 3b shows mean osteolytic lesion area (mm$^2$) at sacrifice (mean±SD). Osteolytic lesions were also smaller in groups 2, 4 and 5. FIG. 3c shows number of osteolytic lesions at sacrifice (mean±SD). There were less osteolytic lesions in groups 2 and 5, but more in group 3. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Fluorescence Analysis

Figure 4:
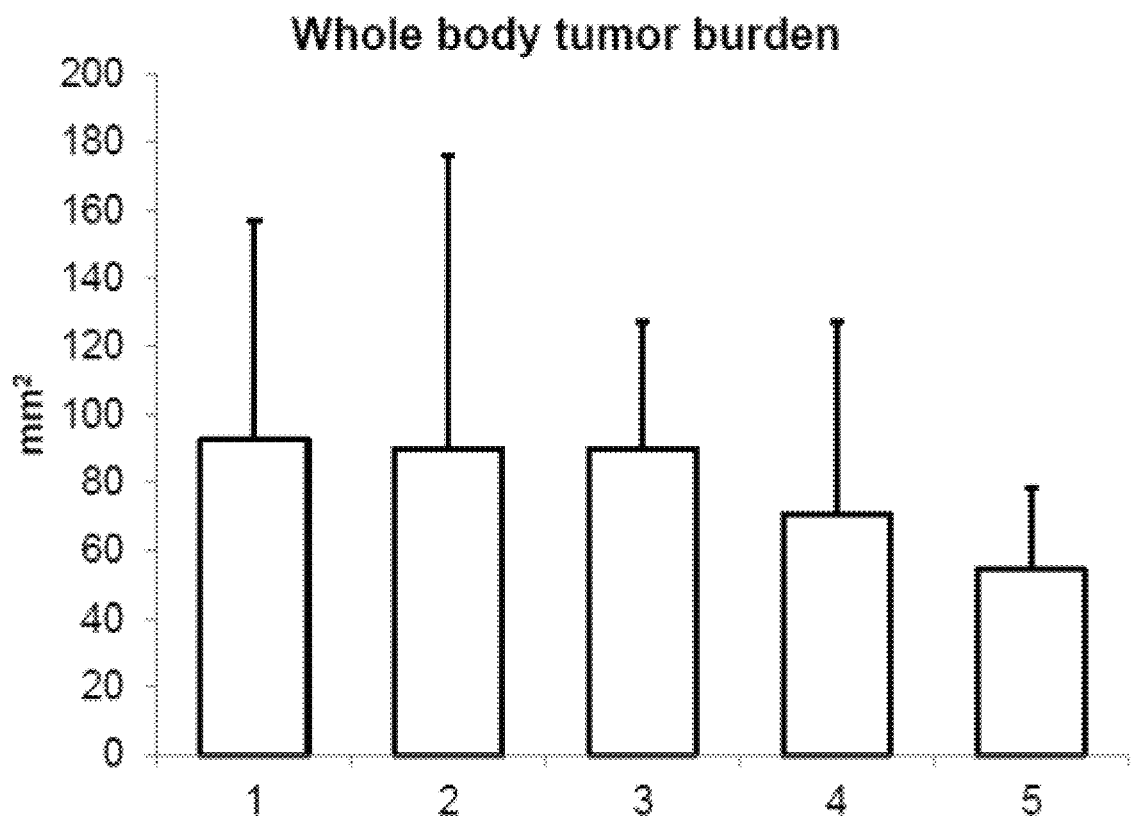
FIG. 4 shows illustrative results of whole body tumor burden ($mm^2$) at sacrifice (mean±SD). The results are shown as the average of fluorescent area in two pictures (prone and supine positions) of each animal. Statistical analysis was performed using Kruskal Wallis test. Statistically significant differences were not observed (p=0.251).

FIG. 4 shows whole body tumor burden (mm$^2$) at sacrifice (mean±SD) of Groups 1-5. The results are shown as the average of fluorescent area in two pictures (prone and supine positions) of each animal. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Serum TRACP 5b

Tartrate-resistant acid phosphatase (TRACP) is an enzyme that is expressed in high amounts by bone resorbing osteoclasts, inflammatory macrophages and dendritic cells. Two forms of TRACP circulate in human blood, TRACP 5a derived from macrophages and dendritic cells, and TRACP 5b derived from osteoclasts. Recent data have demonstrated the utility of TRACP 5b as a marker of osteoclast number and bone resorption, and serum TRACP 5a as a marker of inflammatory conditions.

Figure 5:
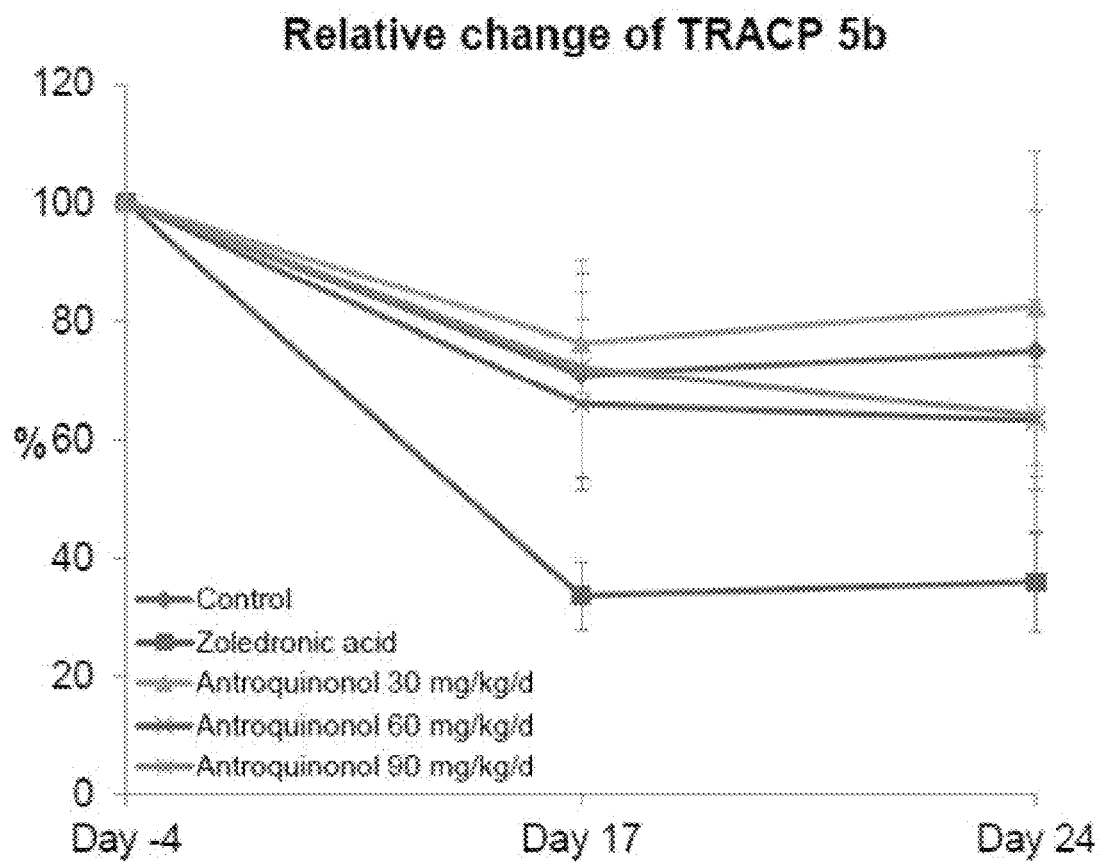
FIG. 5 shows illustrative results of relative change (%) in serum TRACP 5b activity during the study (mean±SD).

FIG. 5 shows relative change (%) in serum Tartrate-resistant acid phosphatase 5b (TRACP 5b) activity during the study (mean±SD) of Groups 1-5. Results of statistical analyzes are presented in FIGS. 6a and 6b. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Figure 6A:
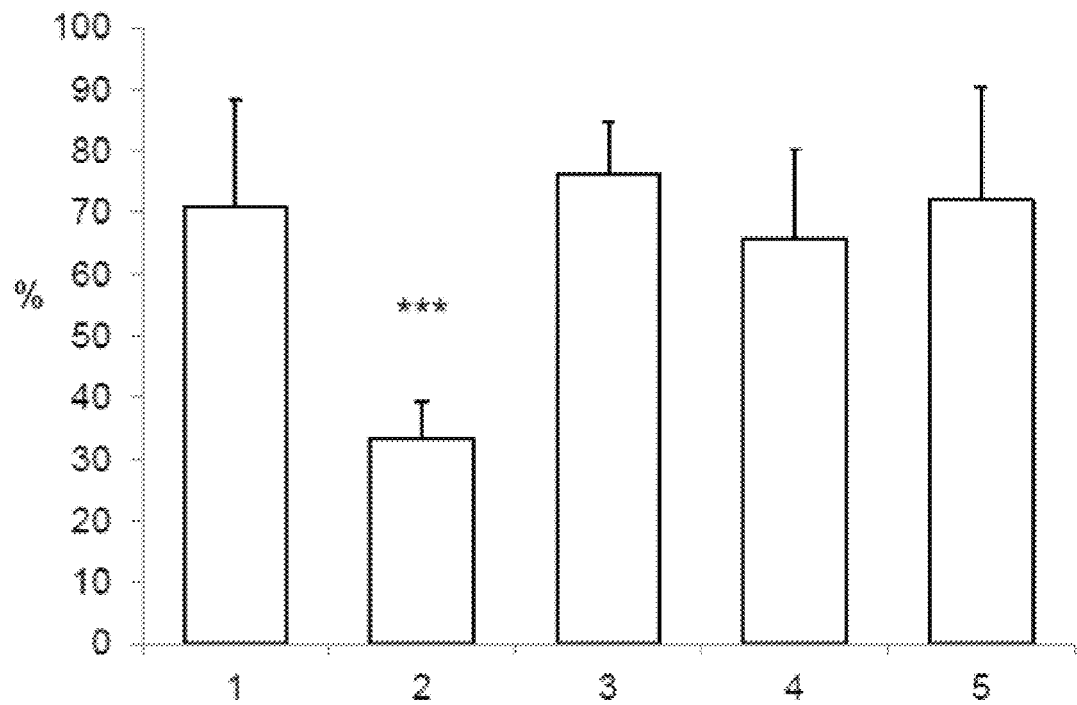
FIGS. 6a and 6b show illustrative results of relative change from day −4 to day 17 in serum TRACP 5b activity (mean±SD) and relative change from day −4 to day 24 in serum TRACP 5b activity (mean±SD), respectively.
Figure 6B:
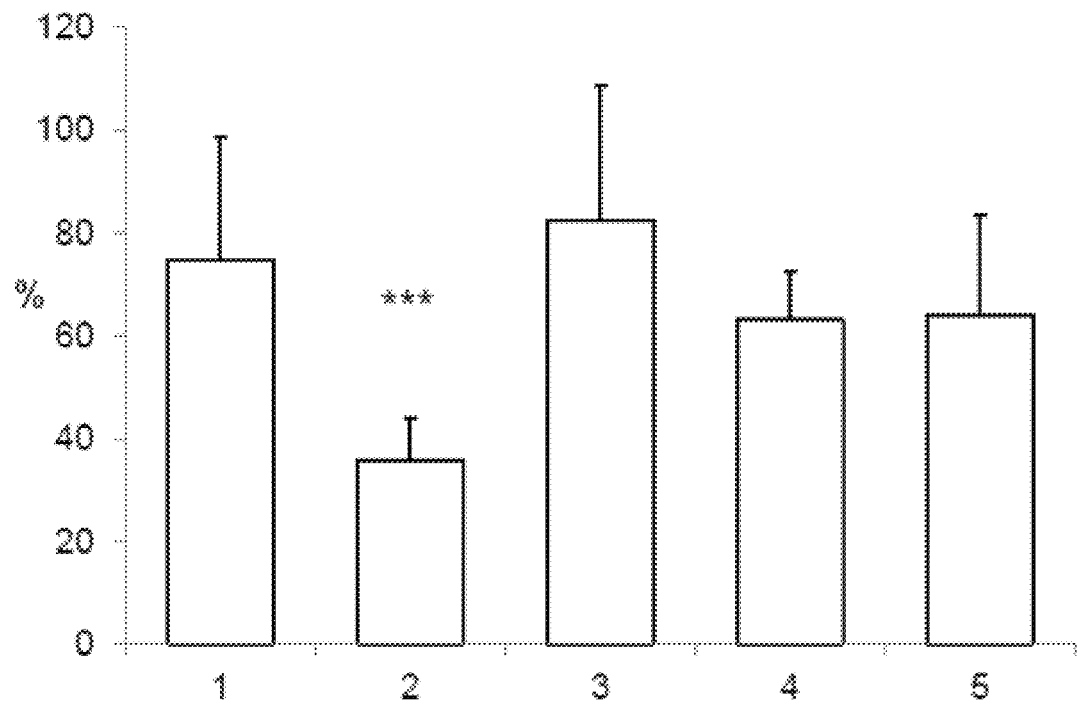

FIG. 6a shows relative change from day −4 to day 17 in serum TRACP 5b activity (mean±SD). TRACP 5b activity was decreased in group 2. FIG. 6b shows relative change from day −4 to day 24 in serum TRACP 5b activity (mean±SD). TRACP 5b activity was decreased in group 2. Compared to Group 1 (Control), Groups 4 and 5 showed decreased TRACP 5b activity at day 24, although not as significant as Group 2. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Serum PINP

Serum procollagen 1 N-terminal propeptide (PINP) is a sensitive bone formation marker in humans. Serum PINP has emerged as a reliable marker of bone turnover in humans and is routinely used to monitor bone formation.

Figure 7:
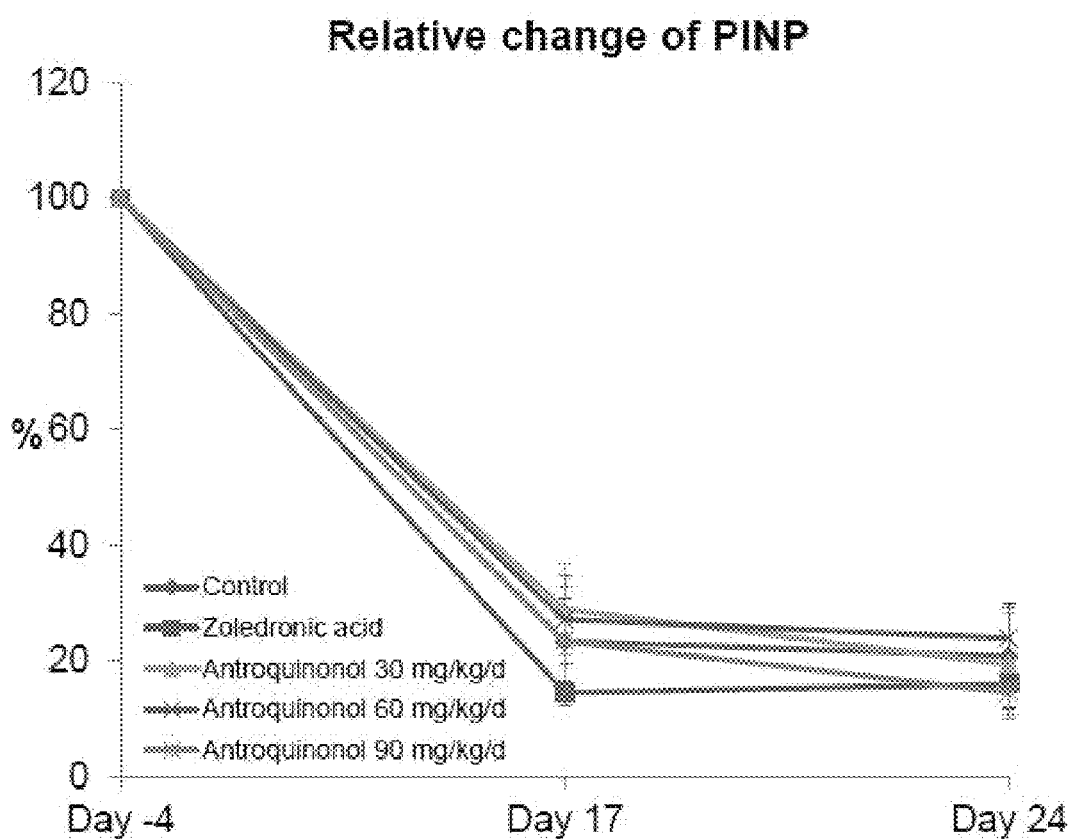
FIG. 7 shows illustrative results of relative change (%) in serum procollagen 1 N-terminal propeptide (PINP) values during the study (mean±SD).
Figure 8A:
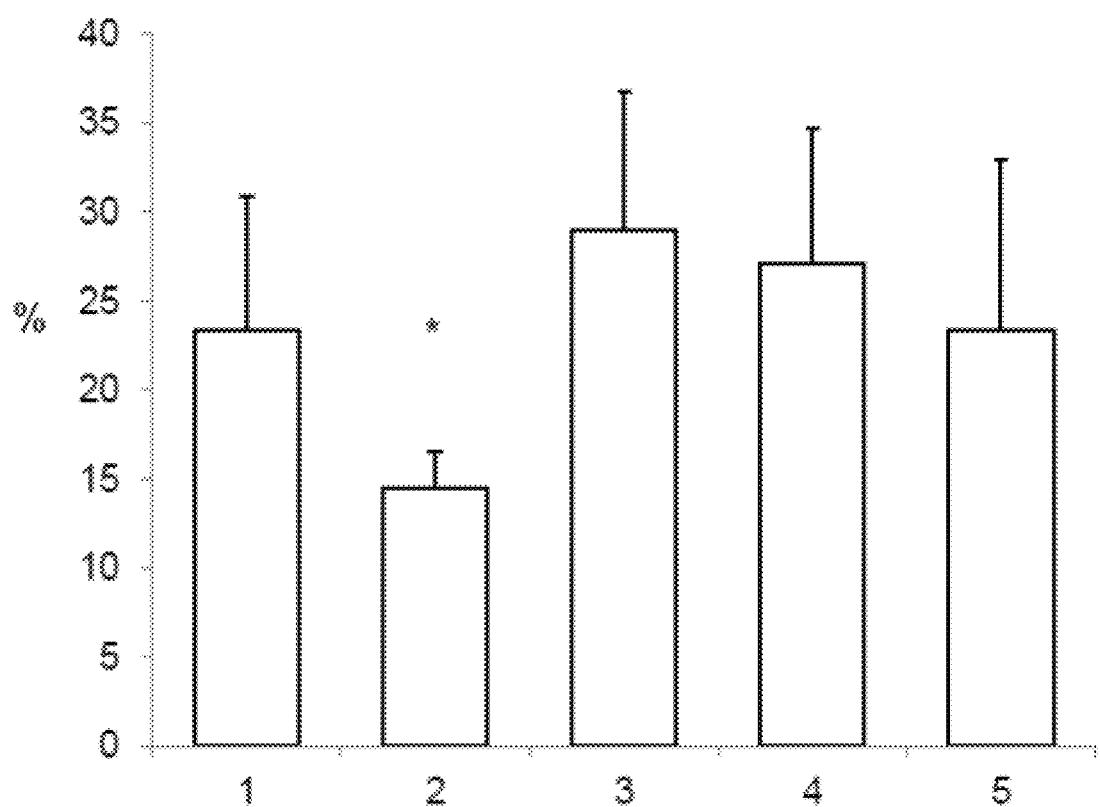
FIGS. 8a and 8b show illustrative relative change from day −4 to day 17 in serum PINP values (mean±SD) and relative change from day −4 to day 24 in serum PINP values (mean±SD), respectively.
Figure 8B:
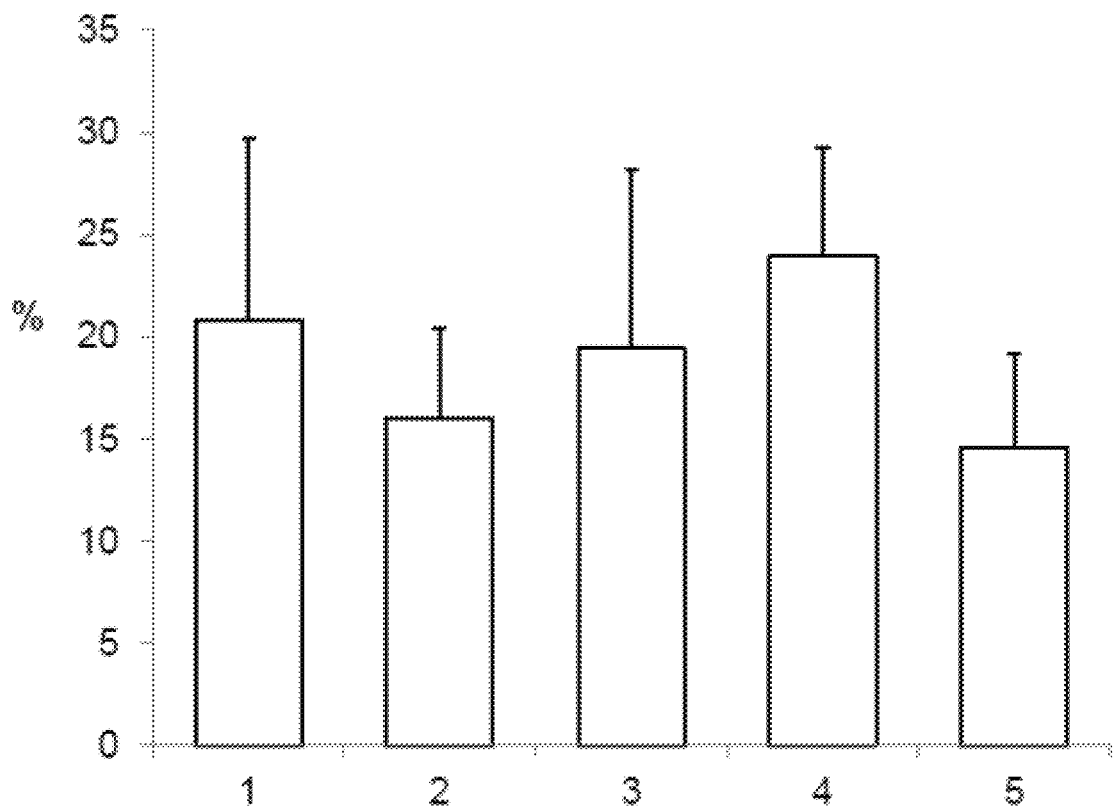

FIG. 7 shows relative change (%) in serum PINP values during the study (mean±SD) of Groups 1-5. Results of statistical analyzes are presented in FIGS. 8a and 8b. FIG. 8a illustrates relative change from day −4 to day 17 in serum PINP values (mean±SD). PINP activity was decreased in group 2 (recorded at day 17). FIG. 8b illustrates relative change from day −4 to day 24 in serum PINP values (mean±SD). Compared to Group 1 (control), Groups 2 and 5 showed a lower PINP activity at day 24. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Histomorphometry

Figure 9:
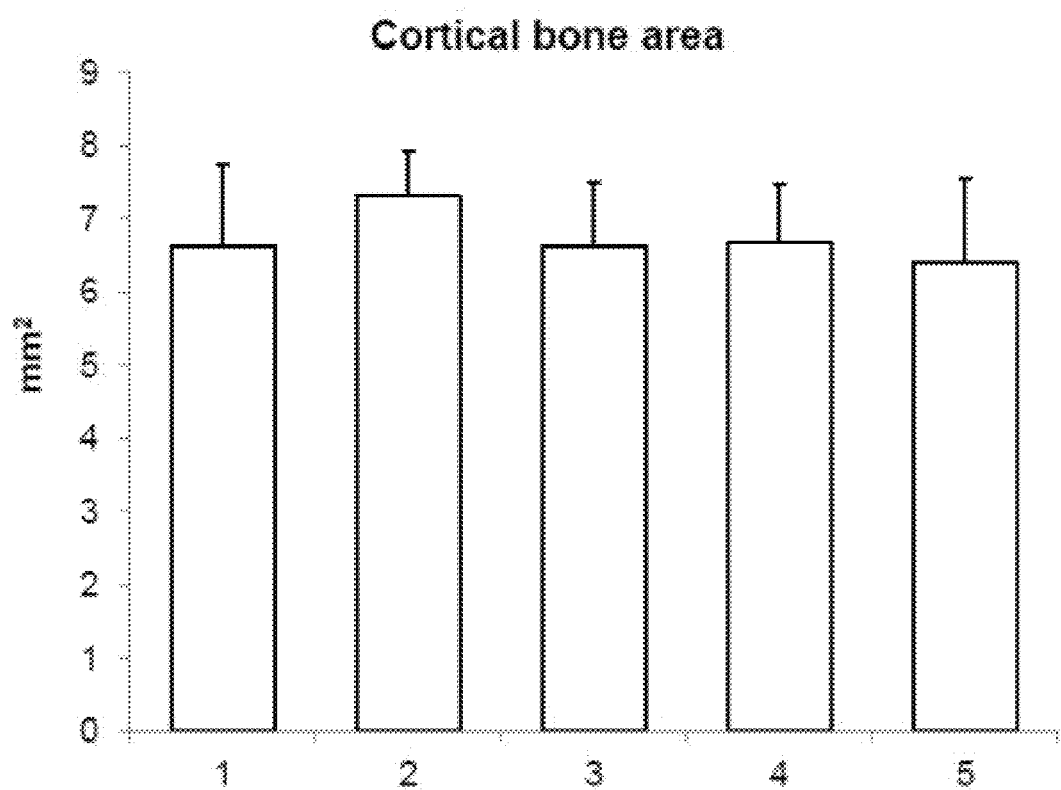
FIG. 9 shows illustrative results of cortical bone area ($mm^2$, mean±SD). Statistical analysis was performed using Oneway ANOVA followed by Dunnett's test for pairwise comparison against the control group. Statistically significant differences were not observed.
Figure 10:
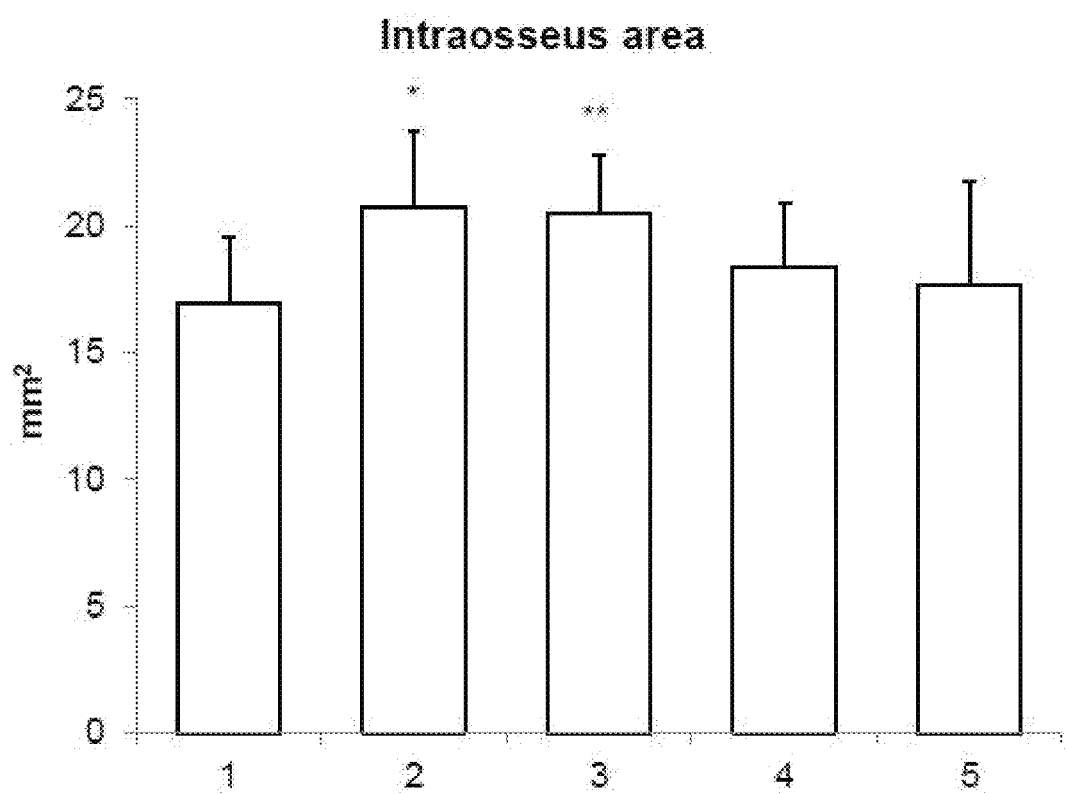
FIG. 10 shows illustrative results of intraosseus area (bone marrow space with trabecular bone included). Statistical analysis was performed using Oneway ANOVA followed by Dunnett's test for pairwise comparison against the control group. One asterisk (*) indicates a statistically significant difference with a p-value<0.05 and two asterisks (**) with a p-value<0.01. Intraosseous area was increased in groups 2 and 3.
Figure 11:
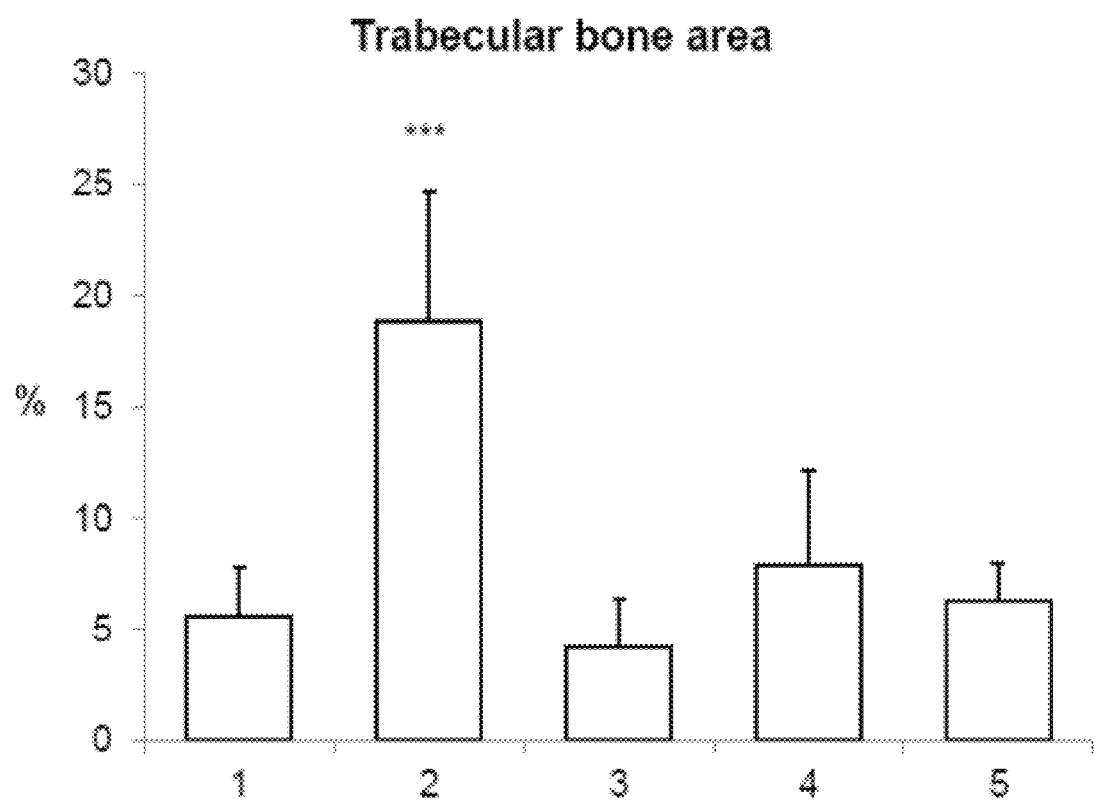
FIG. 11 shows illustrative results of trabecular bone area (relative to the intraosseous area). Statistical analysis was performed using Oneway ANOVA with logarithmic transformation followed by Dunnett's test for pairwise comparison against the control group. Three asterisks (***) indicate a statistically significant difference with a p-value<0.001. Trabecular bone area was increased in group 2.
Figure 12:
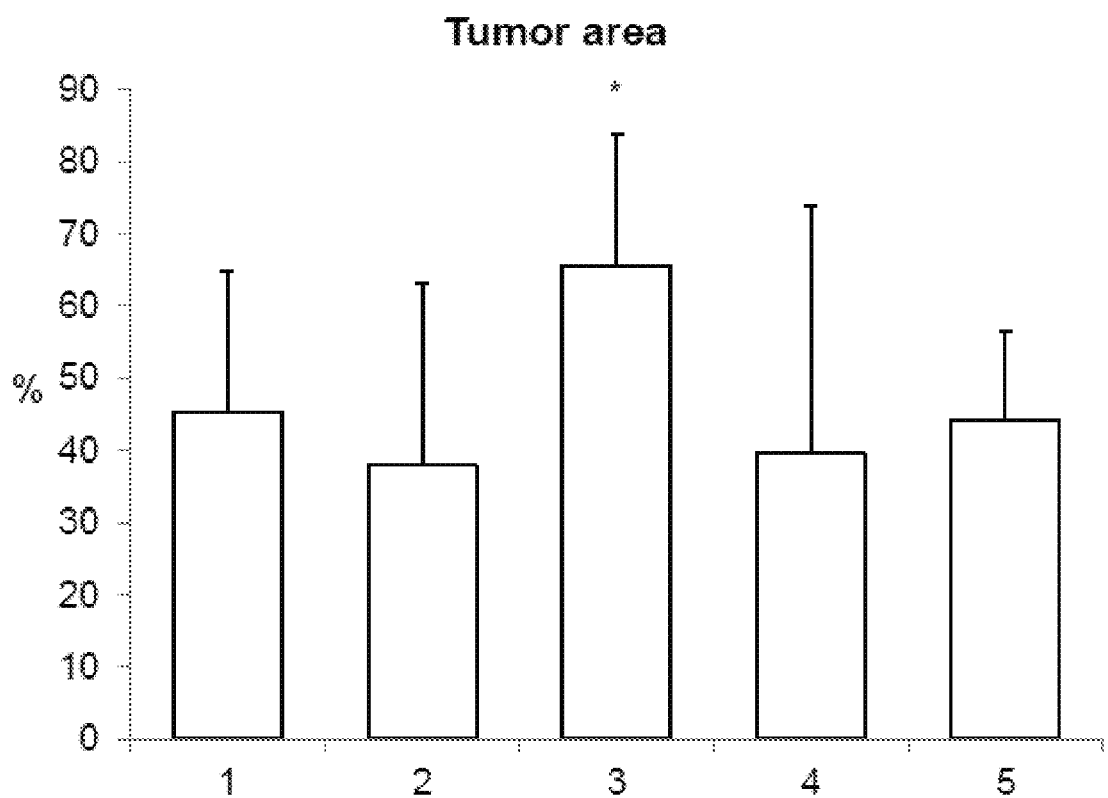
FIG. 12 shows illustrative results of tumor area (relative to the intraosseous area). Statistical analysis was performed using Kruskall Wallis test followed by Mann-Whitney U-test for pairwise comparison. Tumor area was increased in group 3.
Figure 13:
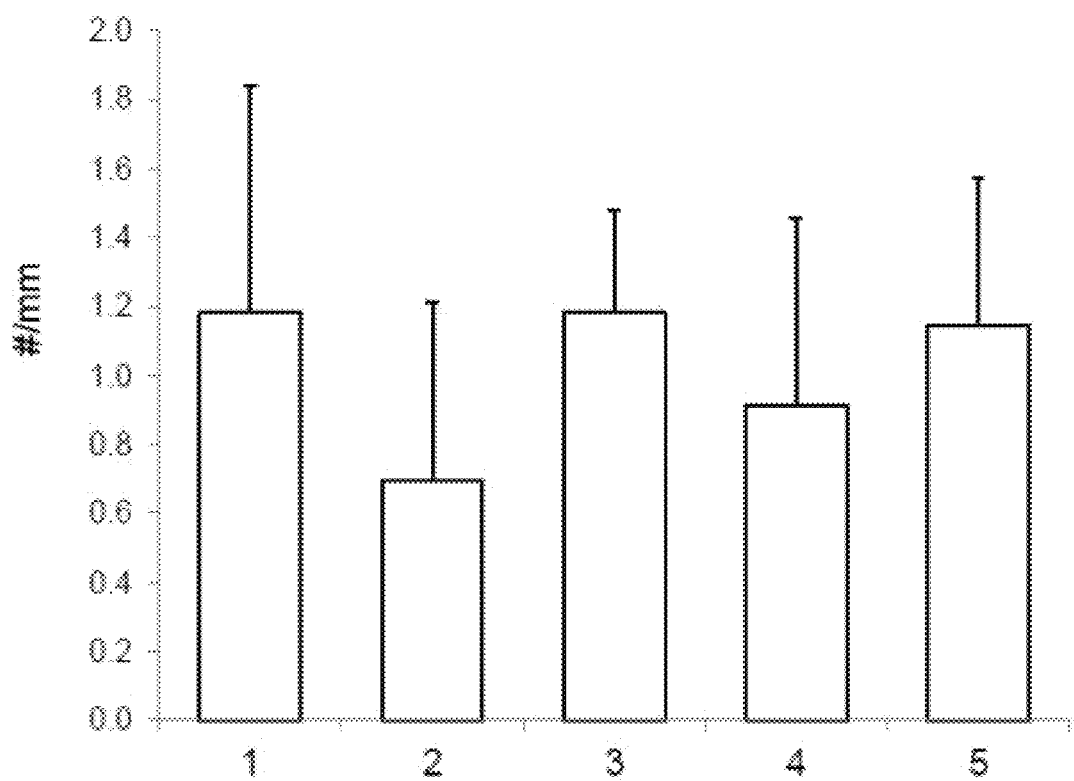
FIG. 13 shows illustrative results of number of osteoclasts at tumor-bone interface (relative to the tumor-bone interface length, #/mm). Statistical analysis was performed using Kruskal-Wallis test. Statistically significant differences were not observed.

FIG. 9 shows cortical bone area (mm$^2$, mean±SD) of Groups 1-5. FIG. 10 shows illustrative results of intraosseus area (bone marrow space with trabecular bone included). Intraosseous area was increased in groups 2 and 3. In addition, FIG. 11 illustrates trabecular bone area (relative to the intraosseous area) and FIG. 12 illustrates tumor area (relative to the intraosseous area). Trabecular bone area was increased in group 2 and Tumor area was increased in group 3. FIG. 13 shows number of osteoclasts at tumor-bone interface (relative to the tumor-bone interface length, #/mm). Statistically significant differences were not observed. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Summary of the Results

Table 3 provides summary of the results shown before. An upwards arrow (↑) indicates increase and a downwards arrow (↓) a decrease. One asterisk (*) indicates a statistically significant difference with a p-value<0.05, two asterisks () with a p-value<0.01, and three asterisks (*) with a p-value<0.001. NS=Non-significant.

TABLE 3

| METHOD/PARAMETER | Zoledronic acid | Compound 1 30 mg/kg/d | Compound 1 60 mg/kg/d | Compound 1 90 mg/kg/d |
|---|---|---|---|---|
| BODY WEIGHT | | | | |
| Relative change of body weight at sacrifice | NS | NS | NS | ↑* |
| Relative maximum weight | NS | NS | NS | ↑* |
| Study day of maximum weight | NS | NS | NS | NS |
| Relative loss of body weight from maximum weight | NS | NS | NS | NS |
| PARAPLEGIA AND CACHEXIA | | | | |
| Paraplegia | NS | NS | NS | NS |
| Cachexia | NS | NS | NS | NS |
| RADIOGRAPHIC ANALYSIS | | | | |
| Total osteolytic lesion area | ↓*** | NS | ↓* | ↓** |
| Mean osteolytic lesion area | ↓*** | NS | ↓** | ↓* |
| Total osteolytic lesion count | ↓*** | ↑* | NS | ↓* |
| FLUORESCENCE ANALYSIS | | | | |
| Whole body tumor buden | NS | NS | NS | NS |
| BONE MARKERS | | | | |
| TRACP 5b change at day 17 | ↓*** | NS | NS | NS |
| TRACP 5b change at day 24 | ↓* | NS | NS | NS |
| PINP change at day 17 | ↓* | NS | NS | NS |
| PINP change at day 24 | NS | NS | NS | NS |
| HISTOMORPHOMETRY | | | | |
| Intraosseous area | ↑* | ↑** | NS | NS |
| Cortical bone area | NS | NS | NS | NS |
| Trabecular bone area | ↑* | NS | NS | NS |
| Tumor area | NS | ↑* | NS | NS |
| Osteoclast number at tumor-bone interface | NS | NS | NS | NS |

In conclusion, zoledronic acid prevented the formation of osteolytic lesions and decreased TRACP 5b. PINP was decreased at day 17. Trabecular bone area was increased. Zoledronic acid exhibited no effect on body weight, whole body tumor burden or intraosseous tumor area, as expected. Compound 1 dose 90 mg/kg/d increased the maximum weight obtained during the study and the body weight at sacrifice. Compound 1 decreased the total osteolytic area and mean osteolytic lesion size at doses 60 and 90 mg/kg/d. The number of osteolytic lesions was decreased at Compound 1 dose 90 mg/kg/d. Statistically significant effects on the whole body tumor burden were not found. Compound 1 dose 30 mg/kg/d increased and higher doses had no effect on intraosseous tumor area. Compound 1 did not have any effect on cortical or trabecular bone area as analysed by histomorphometry.

Example 3

The Effects of Compound 1 in a Prostate Cancer Bone Metastasis Model

Patients with prostate cancer typically develop metastases to bone. Almost all prostate cancer patients with end-stage disease have bone metastases. Bone metastases caused by prostate cancer are mainly osteoblastic, causing severe bone pain and also increasing the risk of fractures. Although the primary tumor could be successfully removed, the disease may have already spread to bone. In this case, the disease can develop further visceral and bone metastases. Currently, there is no efficient cure for prevention or treatment of bone metastases.

The objective of this study was to test the efficacy of three different doses of the test compound 1 on prostate cancer bone metastases in male athymic nude mice in a 5-week study in preventive setting. The following 5 experimental groups were included in the study:
1. Control group receiving vehicle (po twice a day)
2. Reference group receiving zoledronic acid (sc at days 1 and 14)+vehicle (po twice a day)
3. Test group receiving 15 mg/kg of test compound (po twice a day)
4. Test group receiving 30 mg/kg of test compound (po twice a day)
5. Test group receiving 45 mg/kg of test compound (po twice a day)

The vehicle was corn oil. All groups included 15 mice that were 7 weeks of age at the beginning of the study. Based on the body weights the animals were randomized to five groups. On day 0, the animals were given an intratibial inoculation of human prostate cancer cells. Body weights were determined twice a week. The development of osteoblastic and osteolytic lesions were followed by x-ray. The test compound and vehicle were administered by oral gavage twice a day. The animals were sacrificed at day 35. Tissue samples were collected for histology and embedded in paraffin from left and right tibia and femur for possible future histomorphometric analyses. Gross necropsy was performed to all animals at the end of the study, and all macroscopic signs were recorded.

Materials and Equipment

Test Compound

Test compound 1 (99.85%, specific density: 1.005) was obtained in liquid form. Three 50× stock solutions were prepared in corn oil (75 mg/ml, 150 mg/ml and 225 mg/ml) and stored them in dark at +4° C. The dosing solutions of 1.5, 3.0 and 4.5 mg/ml were prepared from the stock solutions by diluting the stock solutions in corn oil 1:50. The dosing solutions were prepared once a week and stored in dark at +4° C. The dosing volume was 10 ml/kg. The test compound was administered by oral gavage twice a day with dosing intervals of 10+14 hours. The dosings were started at day 1 and performed at the same time every day.

Reference Compound

Zoledronic acid was used as a reference compound. 100l of Zometa® (Novartis Pharma GmbH, Nürnberg, Germany) 4 mg/5 ml infusion concentrate was diluted in 3.9 ml of sterile saline (0.9% NaCl) to obtain the administration concentration of 0.02 mg/ml. This solution was prepared once during the study and stored at +4° C. The dosing volume was 5 ml/kg, resulting in the dose of 0.1 mg/kg. The reference compound was administered SC twice in the study: at days 1 and 14.

Vehicle

The vehicle was corn oil (Sigma-Aldrich).

Primary Materials, Animals and Primary Equipment

Male athymic nude mice (Hsd:Athymic nude-nu, obtained from Harlan, The Netherlands) and PC-3 human prostate cancer cells (ATCC) were used for this study.

In this model, human prostate cancer cells are inoculated into the left proximal tibia of 5-7 week old male athymic nude mice. This mouse strain is immunodeficient, allowing rapid spreading of the human cancer cells. The bone lesions are mixed, being mainly osteolytic but also containing an osteoblastic component. Within four weeks after the inoculation part of the animals have already developed some bone lesions, that can be visualized by X-ray radiography. At 7 weeks, the bone metastases are clearly visible. The animals are sacrificed at 7-8 weeks after inoculation, and their bones are collected for further histomorphometric analysis.

The bone metastasis model provided herein can be conveniently used to test drug candidates that have been shown in preliminary studies to affect one or more of the following: 1) growth of cancer cells; 2) angiogenesis; 3) function or differentiation of osteoclasts. The model can also be used for finding new indications to existing drugs, allowing the pharmaceutical companies a way of finding new indications to patented drugs that have already proved efficient in some other indications.

Procedures

Animal Handling and Cell Culture

Male athymic nude mice (Hsd:Athymic nude-nu, obtained from Harlan, The Netherlands) were used for this study. The age of the animals was 7 weeks, and their body weights were approximately 18-25 g at the beginning of the study. The mice were specific pathogen free (SPF) and isolator-reared animals. Correct age and good clinical health were qualifications for the study. The minimum quarantine and acclimatization period for the mice was 7 days. Allocation to groups was performed by randomization procedure based on body weight. The animals were marked with tail and ear marks. The mice were housed in Scantainer®, 5 mice per cage. In case of fighting, some of the animals had to be isolated. For intratibial inoculations the mice were anesthetized with i.p. injections of Xylazin (5-6 mg/kg) and Ketamine (92-109 mg/kg). For x-ray imaging the mice were anesthetized with inhalation of isoflurane. Analgesia (buprenorphine: either 0.1 mg/kg, s.c. twice a day or 3 mg/kg po in drinking water) was used for 2 days after the intratibial inoculation (first dose s.c., then in drinking water) and for the last 5 days of the study (in drinking water).

PC-3 human prostate cancer cells ($10^6$ cells in 20 µl of PBS) were inoculated into the left proximal tibia of the mice at day 0, leading to development of bone metastases. The right placement of the needle will be verified by X-ray before inoculating the cells. In case of misplacement, the cells were inoculated to the right proximal tibia instead.

Animal Monitoring

The animals were weighed twice a week and doses were adjusted accordingly. For the last 5 days of the study, the animals were weighed and observed daily to monitor the progression of disease. Appearance of any clinical signs was recorded on follow-up forms. Analgesic was given to all animals for the last 5 days of the experiment.

6 animals were found dead or had to be euthanized due to breathing difficulties (see Table 4). At necropsy, punctured esophagus and oil in thoracic cavity was found. One animal was euthanized due to hemorrhage in the tumor at day 30 (see Table 4). It was weighed and bone samples were prepared.

TABLE 4

The results of animal monitoring - Final N (final number of sample) with prostate cancer cells.

| Group | Animal numbers | Treatment | Final N | Dead animals removed from study (id) | Time of death (study day) | Notes |
|---|---|---|---|---|---|---|
| 1 | 1-15 | Control | 15 | — | | |
| 2 | 1-15 | Zoledronic acid | 15 | — | | |
| 3 | 1-15 | Compound 1 30 mg/kg/d | 14 | 15 | 23 | Esophageal puncture. |
| 4 | 1-15 | Compound 1 60 mg/kg/d | 14 | 10 | 30 | Hemorrhage in the tumor |
| | | | | 15 | 23 | Esophageal puncture. |
| 5 | 1-15 | Compound 1 90 mg/kg/d | 11 | 7 | 25 | Esophageal puncture. |
| | | | | 9 | 12 | Found dead. |
| | | | | 12 | 23 | Esophageal puncture. |
| | | | | 15 | 23 | Esophageal puncture. Esophageal puncture. |

X-Ray Radiography

The development of osteoblastic and osteolytic lesions was monitored by x-ray radiography at 4 weeks and prior to the sacrifice of the animals. The animals were anesthetized and x-rayed in an anteroposterior position with the Faxitron Specimen Radiographic System MX-20 D12 (Faxitron Corp. Illinois, USA) using Faxitron Dicom 3.0-software. At least one radiograph of both hind limbs per animal was taken on each x-ray occasion (31 kV, 10 seconds, magnification 2×). The lesion number and area in hind limbs was determined from the images with MetaMorph image analysis software.

Sacrifice, Autopsy and Sample Collection

At the end of the study (at day 35), the animals were weighed and sacrificed with cervical dislocation under anesthesia. Terminal blood sample was drawn for possible future analyses. Necropsy was carried out in all animals. Macroscopic findings were recorded on the follow-up forms. Ex vivo tissue samples from hind limbs (left and right tibiae and femur) were collected for possible histomorphometric analysis in future. The bone samples were fixed in 10% neutral-buffered formalin for 2-3 days, then decalcified in 10% EDTA for two weeks, and finally processed with conventional paraffin technique for possible histological analyses.

Statistical Analysis

Statistical analysis was performed with SPSS (version 19.0). The mean and standard deviation of each parameter were determined. All statistical analyses were performed as two-sided tests. Normal distribution of residuals and homogeneity of variance were checked before further analyses. In case of violating these assumptions, either log transformation or other appropriate transformation (e.g. square root, reciprocal) was applied. If the assumptions were fulfilled as such or after transformation, one-way ANOVA was used to study if the values obtained between groups are statistically different (with p<0.05). If differences were found, Dunnett's test was used for comparison against the control group. If the assumptions were not fulfilled even after the transformations described above, rank-transformation was applied and the non-parametric Kruskal-Wallis followed by Mann-Whitney U-test was used. Fischer Exact test was used for frequency data.

Deviations from the Original Study Protocol

The following deviations from the original protocol were performed during the study:

Deviation 1: The study was terminated at day 35 instead of day 56 for ethical reasons (large tumors and massive osteolysis with severe fractures). This change does not affect the results of the study because the desired end point was reached.

Results

Body Weight

Figure 14A:
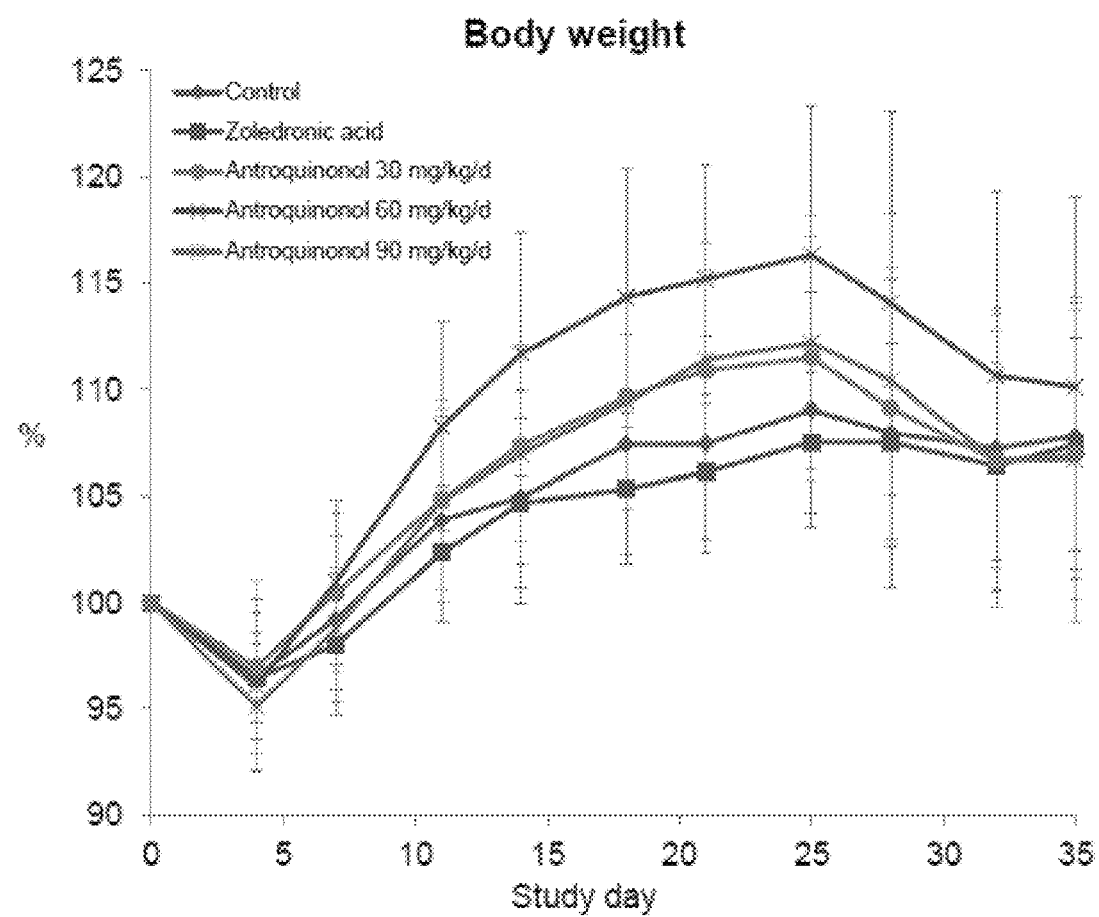
FIGS. 14a and 14b show illustrative results of relative change (%) in body weight of Groups 1-5 during the study (mean±SD), and body weight at sacrifice, respectively.
Figure 14B:
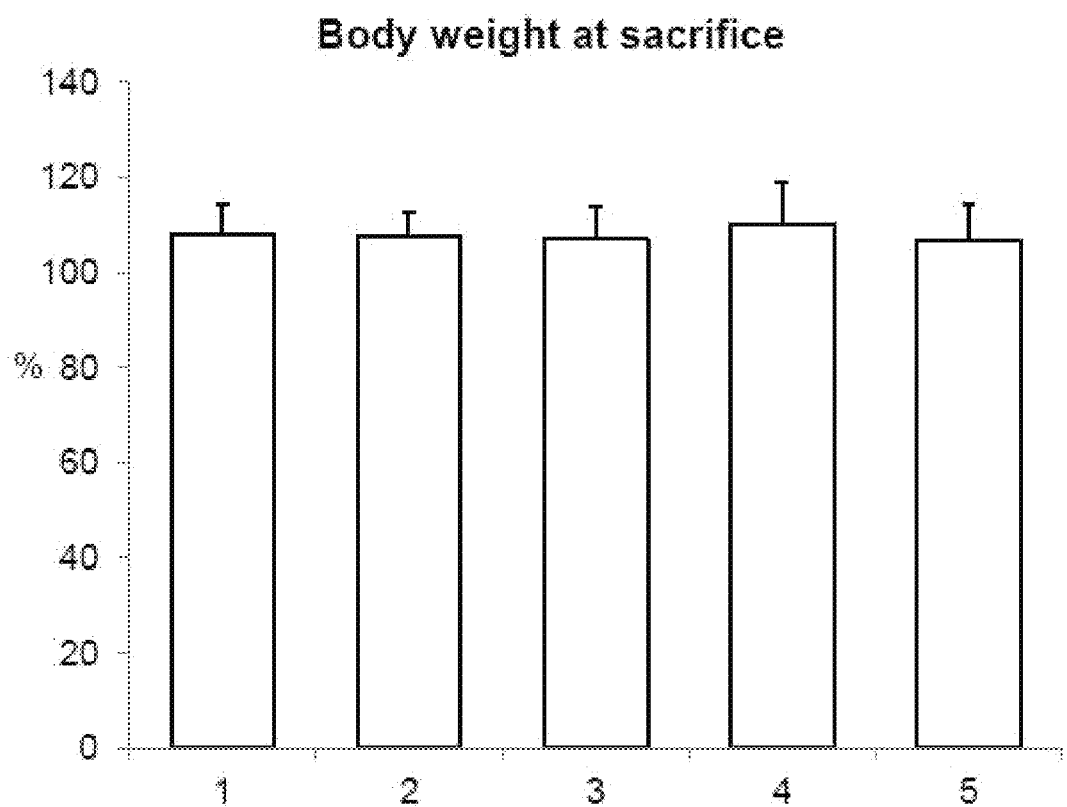
Figure 15A:
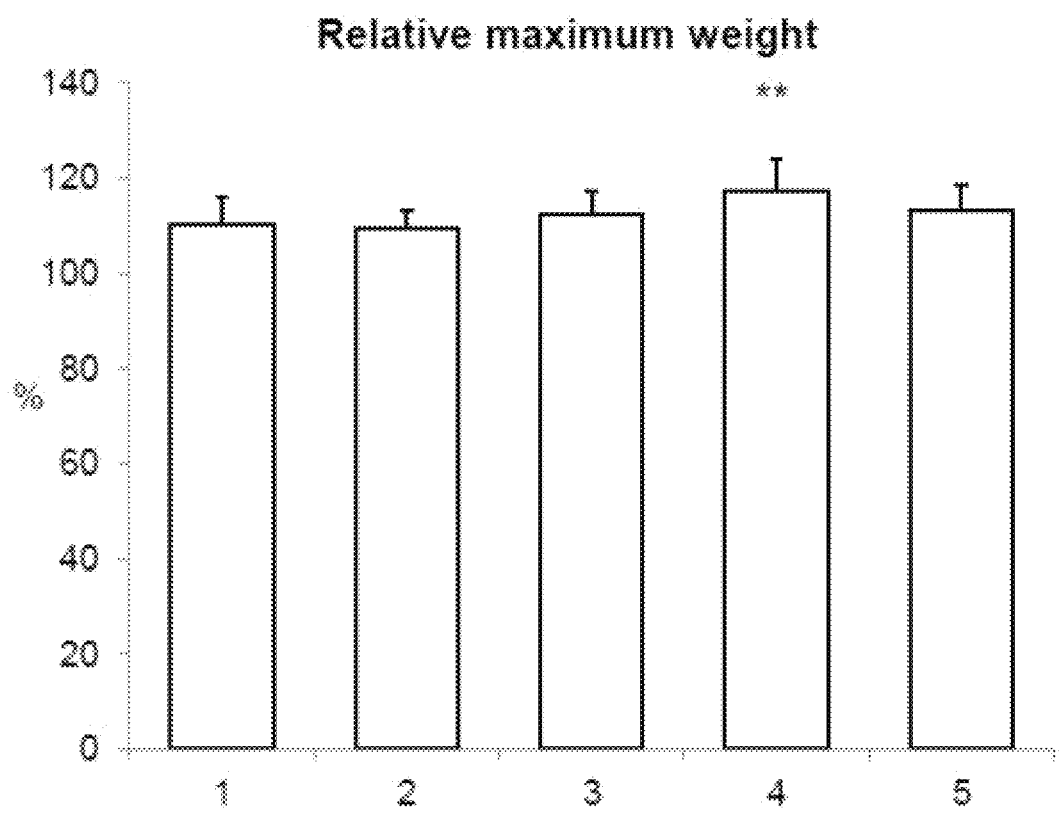
FIGS. 15a and 15b show illustrative results of maximum bodyweight of Groups 1-5 and weight loss from maximum body weight, respectively.
Figure 15B:
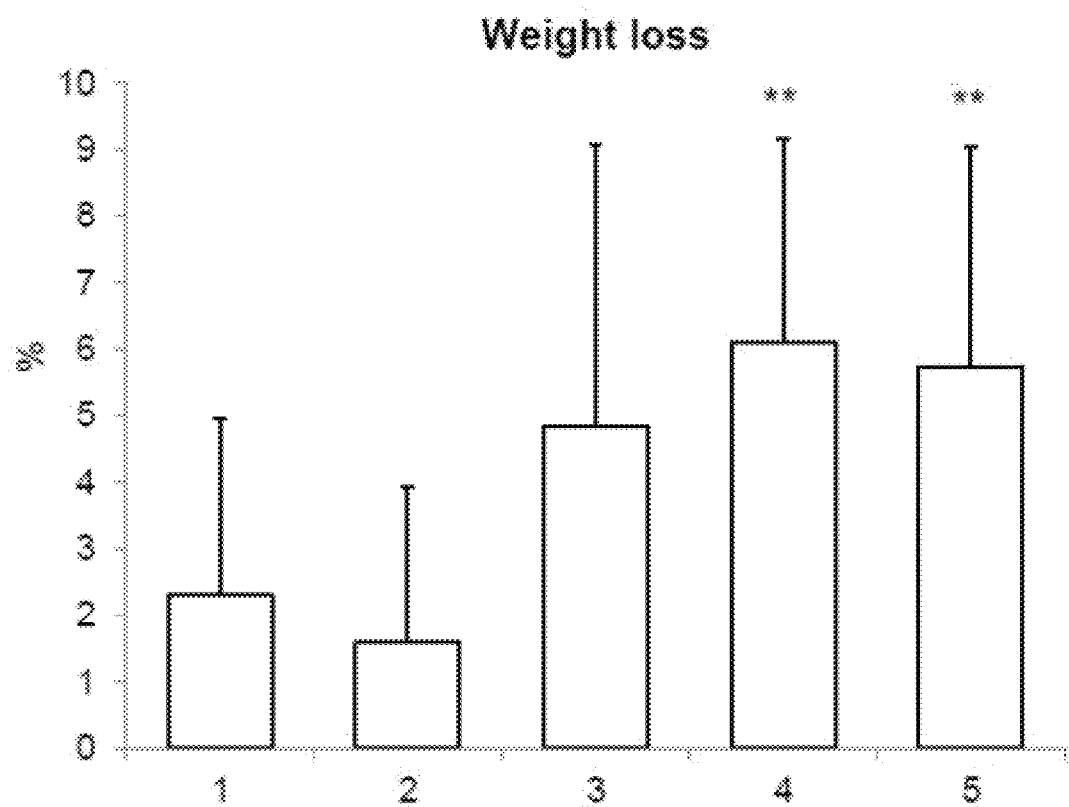

FIG. 14a shows relative change (%) in body weight of Groups 1-5 during the study (mean±SD). Body weight at sacrifice, maximum bodyweight and weight loss from maximum body weight were statistically analyzed and the results are shown in FIGS. 14b, 15a and 15b, respectively. Group 4 obtained more weight during the study and Groups 4 and 5 lost more weight. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Radiographic Analysis

Table 5a provides data of fractures and osteoblastic lesions at day 28. The x-ray images were evaluated qualitatively (yes or no) for osteoblastic lesions (OB) and fractures (FR). Most of the osteoblastic reactions are most likely callus formation in response to fractures. Statistical analysis was performed using Fischer Exact test. One asterisk (*) indicates a statistical significance with p-value<0.05 and three asterisks (***) a statistical significance with p-value<0.001. NS=non-significant. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively. Six animals died before the end of the study (empty cells).

TABLE 5a

Fractures and osteoblastic lesions at day 28.

| Day 28 | Control | Zoledronic acid | Compound 1 30 mg/kg/d | Compound 1 60 mg/kg/d | Compound 1 90 mg/kg/d |
|---|---|---|---|---|---|
| Osteoblastic lesions | 0.0 | 0.0 | 0.0 | 0.0 | 9.1 |
| p-value | | 1.000 | 1.000 | 1.000 | 0.423 |
| Significance | | NS | NS | NS | NS |
| Fractures | 33.3 | 0.0 | 0.0 | 0.0 | 36.4 |
| p-value | | 0.042 | 0.042 | 0.042 | 1.000 |
| Significance | | * | * | * | NS |

TABLE 5b

Fractures and osteoblastic lesions at sacrifice.

| Sacrifice | Control | Zoledronic acid | Compound 1 30 mg/kg/d | Compound 1 60 mg/kg/d | Compound 1 90 mg/kg/d |
|---|---|---|---|---|---|
| Osteoblastic lesions | 66.7 | 0.0 | 35.7 | 21.4 | 45.5 |
| p-value | | 0.000 | 0.143 | 0.025 | 0.423 |
| Significance | | *** | NS | * | NS |
| Fractures | 66.7 | 0.0 | 21.4 | 21.4 | 36.4 |
| p-value | | 0.000 | 0.025 | 0.025 | 0.233 |
| Significance | | *** | * | * | NS |

Figure 16A:
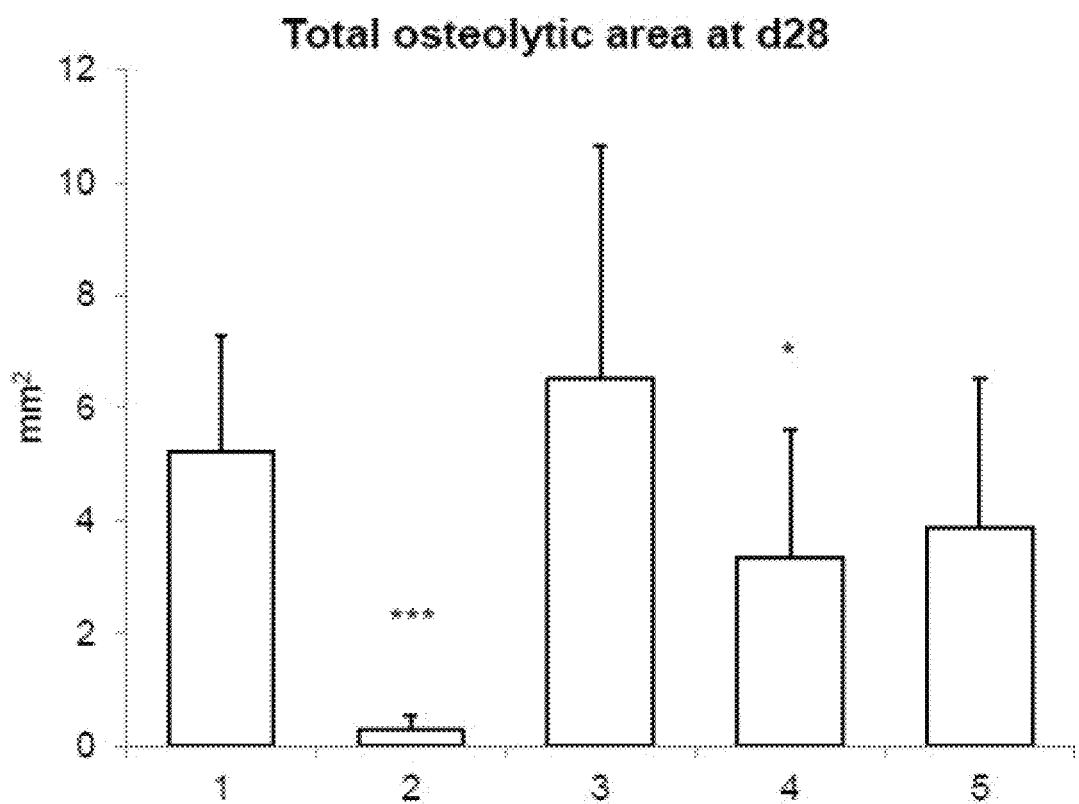
FIGS. 16a and 16b show illustrative results of total osteolytic lesion area ($mm^2$) at day 28 (mean±SD) and total osteolytic lesion area ($mm^2$) at sacrifice (mean±SD), respectively.
Figure 16B:
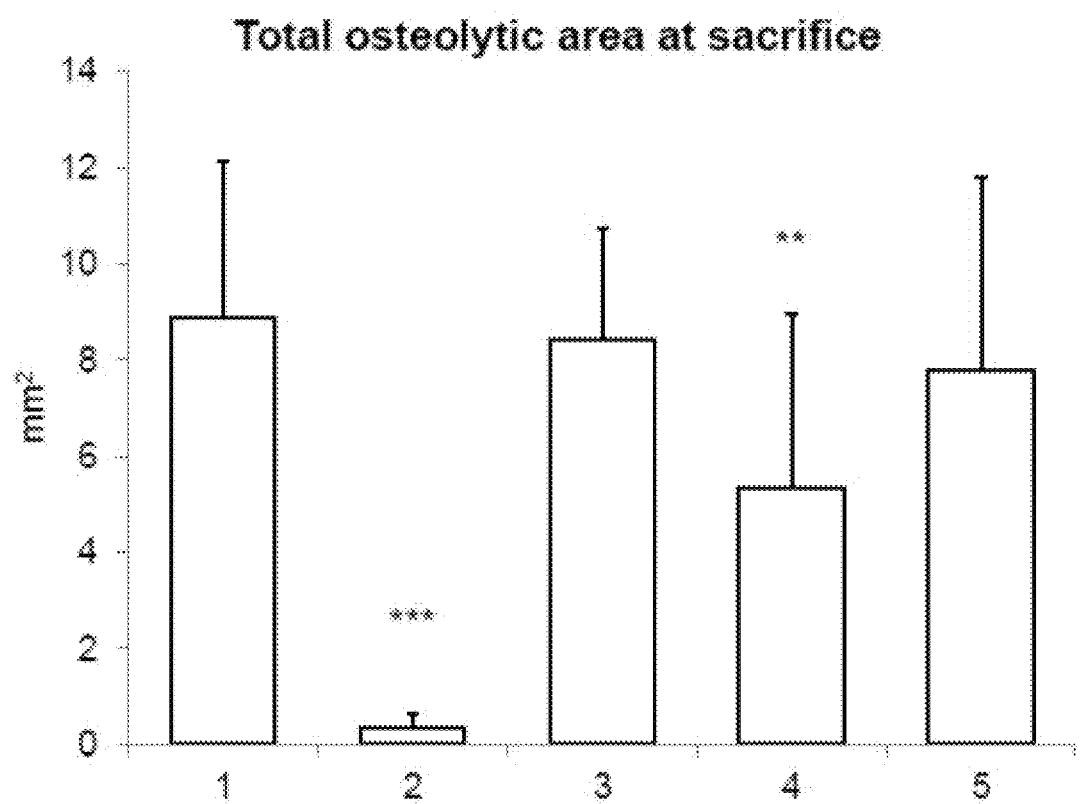

FIG. 16a shows illustrative results of total osteolytic lesion area ($mm^2$) at day 28 (mean±SD). The results are shown as the sum of areas of bone lesions in right and left tibia and femur/animal. Total osteolytic lesion area at day 28 was decreased in groups 2 and 4. Group 5 also showed a similar trend. FIG. 16b shows illustrative results of total osteolytic lesion area ($mm^2$) at sacrifice (mean±SD). The results are shown as the sum of areas of bone lesions in right and left tibia and femur/animal. Total osteolytic lesion area at sacrifice was decreased in groups 2 and 4. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Figure 17A:
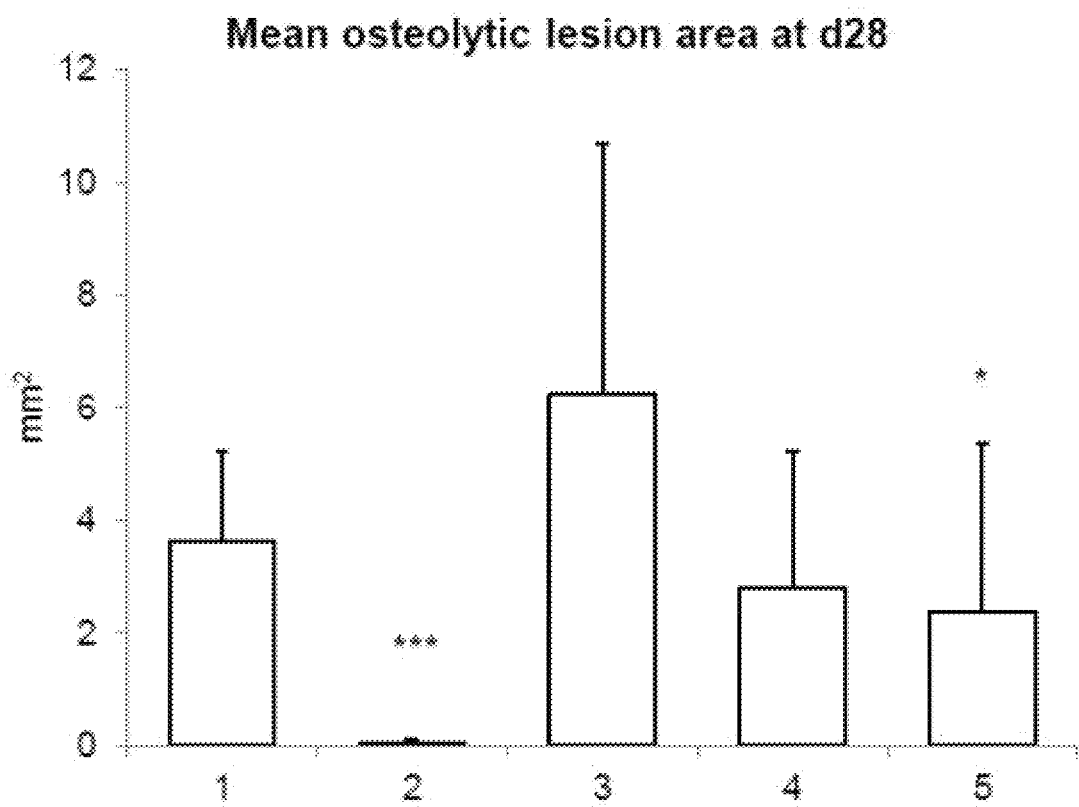
FIGS. 17a and 17b show illustrative results of mean osteolytic lesion area ($mm^2$) at day 28 (mean±SD) and mean osteolytic lesion area ($mm^2$) at sacrifice (mean±SD), respectively.
Figure 17B:
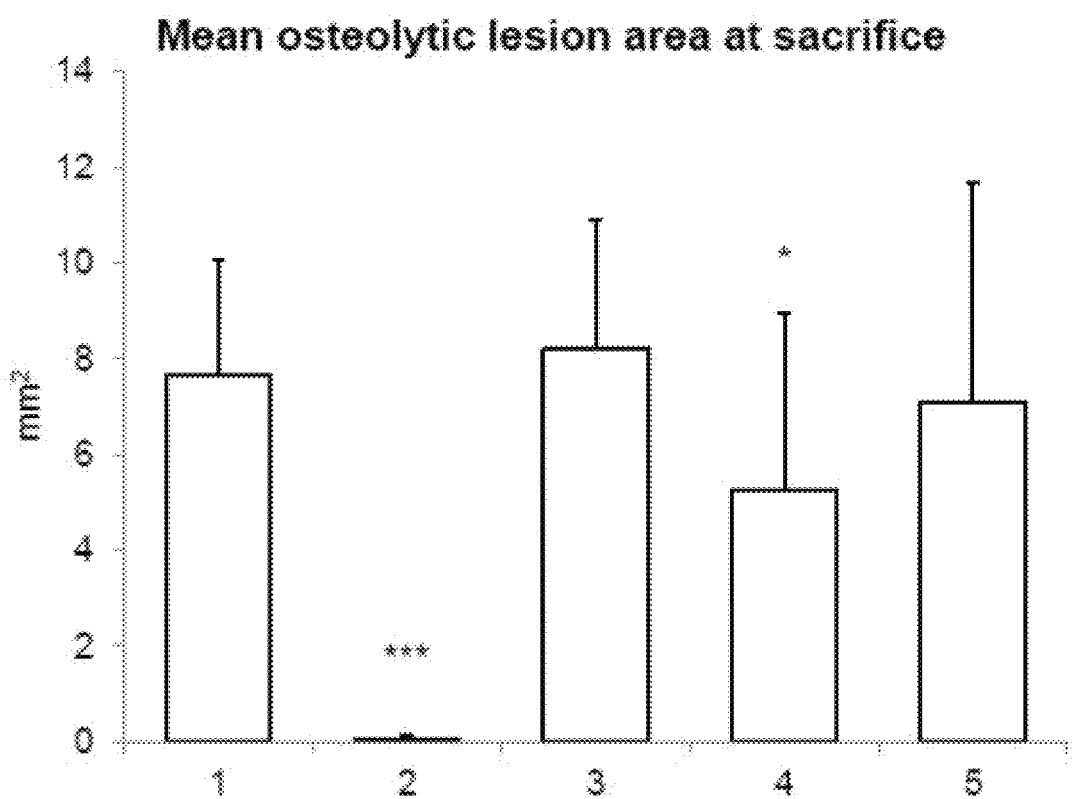

FIG. 17a provides illustrative results of mean osteolytic lesion area ($mm^2$) at day 28 (mean±SD). The results are shown as the mean areas of individual bone lesions in right and left tibia and femur/animal. Osteolytic lesions were smaller in groups 2 and 5 at day 28. Group 4 also showed a similar trend. FIG. 17b provides illustrative results of mean osteolytic lesion area ($mm^2$) at sacrifice (mean±SD). The results are shown as the mean areas of individual bone lesions in right and left tibia and femur/animal. Osteolytic lesions were smaller in groups 2 and 4 at sacrifice. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Figure 18A:
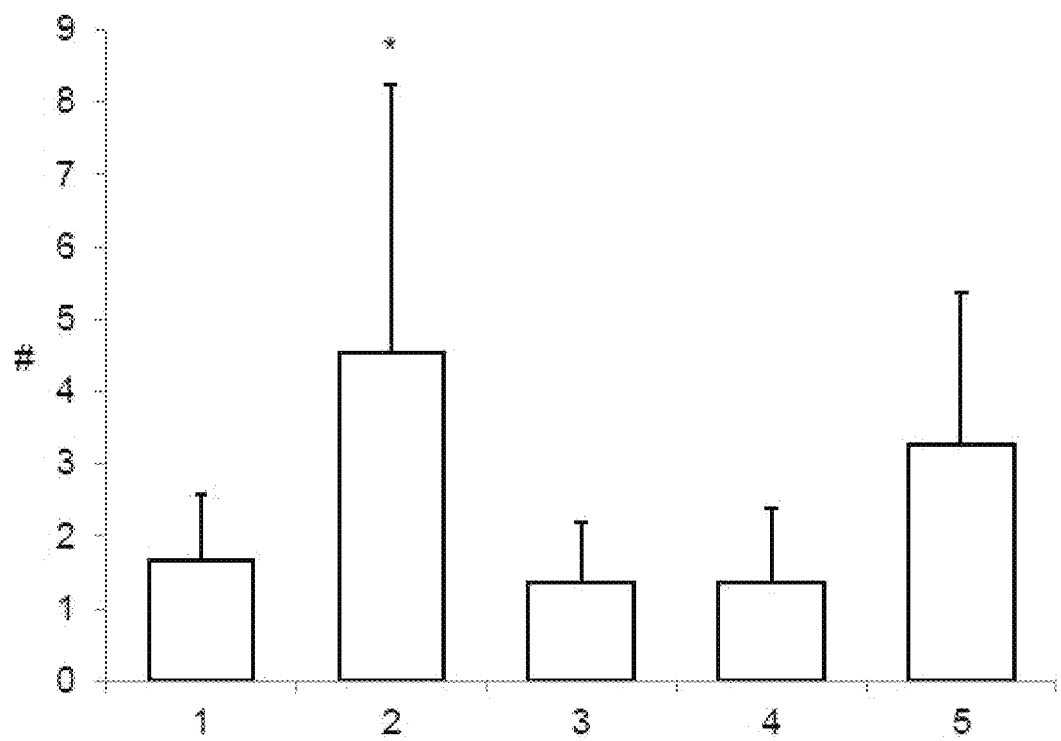
FIGS. 18a and 18b show illustrative results of number of osteolytic lesions at day 28 (mean±SD) and number of osteolytic lesions at sacrifice (mean±SD), respectively.
Figure 18B:
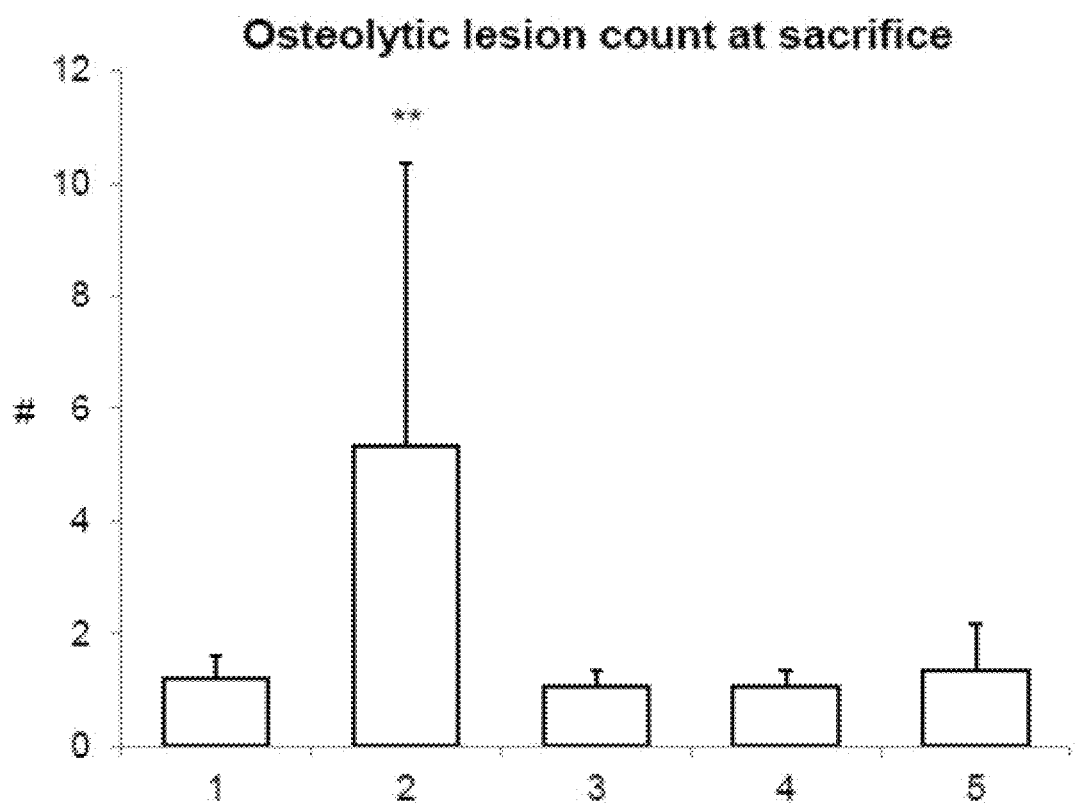

FIG. 18a shows number of osteolytic lesions at day 28 (mean±SD). The results are shown as the count of individual bone lesions in right and left tibia and femur/animal. There were more osteolytic lesions in group 2 because individual lesions were prevented from fusing with each other. FIG. 18b shows number of osteolytic lesions at sacrifice (mean±SD). The results are shown as the count of individual bone lesions in right and left tibia and femur/animal. There were more osteolytic lesions in group 2 because individual lesions were prevented from fusing with each other. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Histomorphometry

Figure 19:
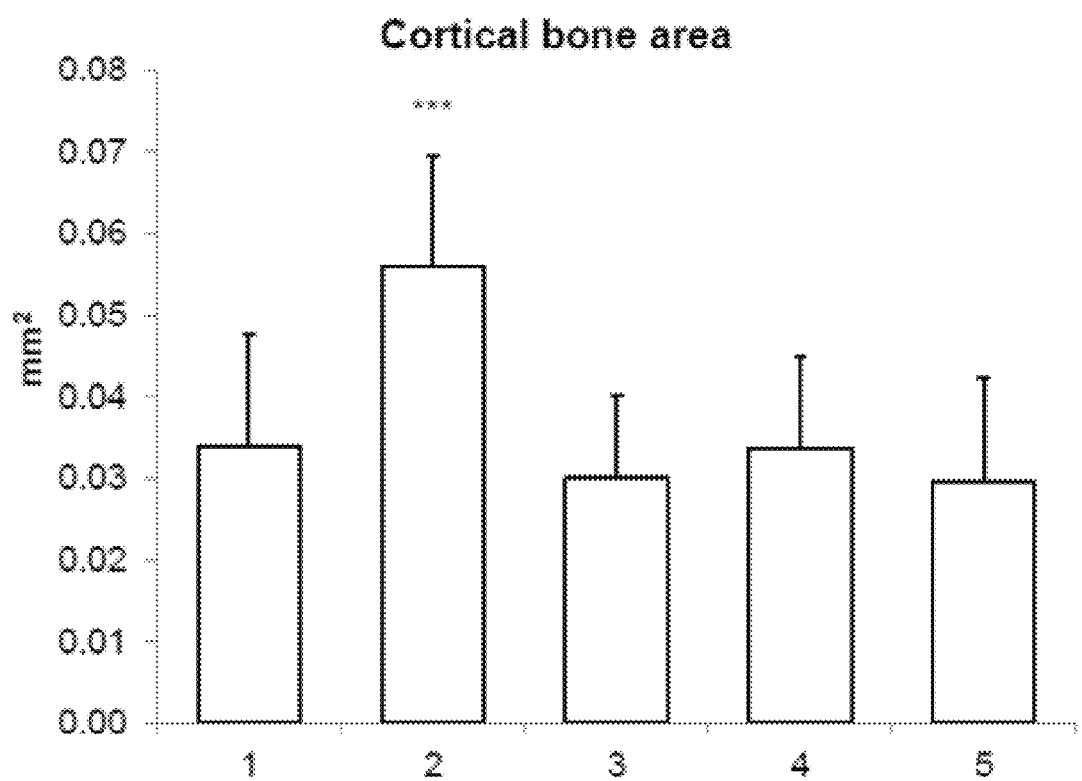
FIG. 19 shows illustrative results of cortical bone area ($mm^2$, mean±SD). Statistical analysis was performed using Oneway ANOVA with square root transformation followed by Dunnett's test for pairwise comparison against the control group. Cortical bone area was increased in group 2.

FIG. 19 shows illustrative results of cortical bone area ($mm^2$, mean±SD) of Groups 1-5. Cortical bone area was increased in group 2. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Figure 20:
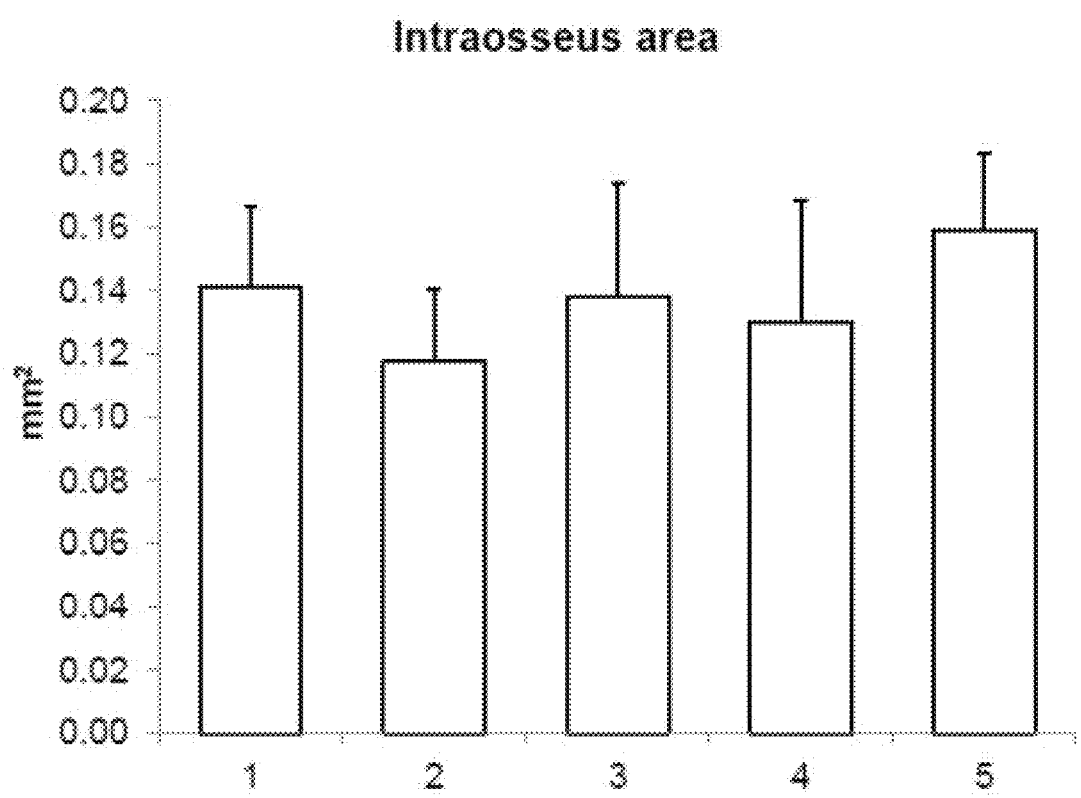
FIG. 20 shows illustrative results of intraosseus area (bone marrow space with trabecular bone included). Statistical analysis was performed using Oneway ANOVA followed by Dunnett's test for pairwise comparison against the control group. Statistically significant differences were not observed.

FIG. 20 shows data of intraosseus area (bone marrow space with trabecular bone included) of Groups 1-5. Statistically significant differences were not observed. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Figure 21:
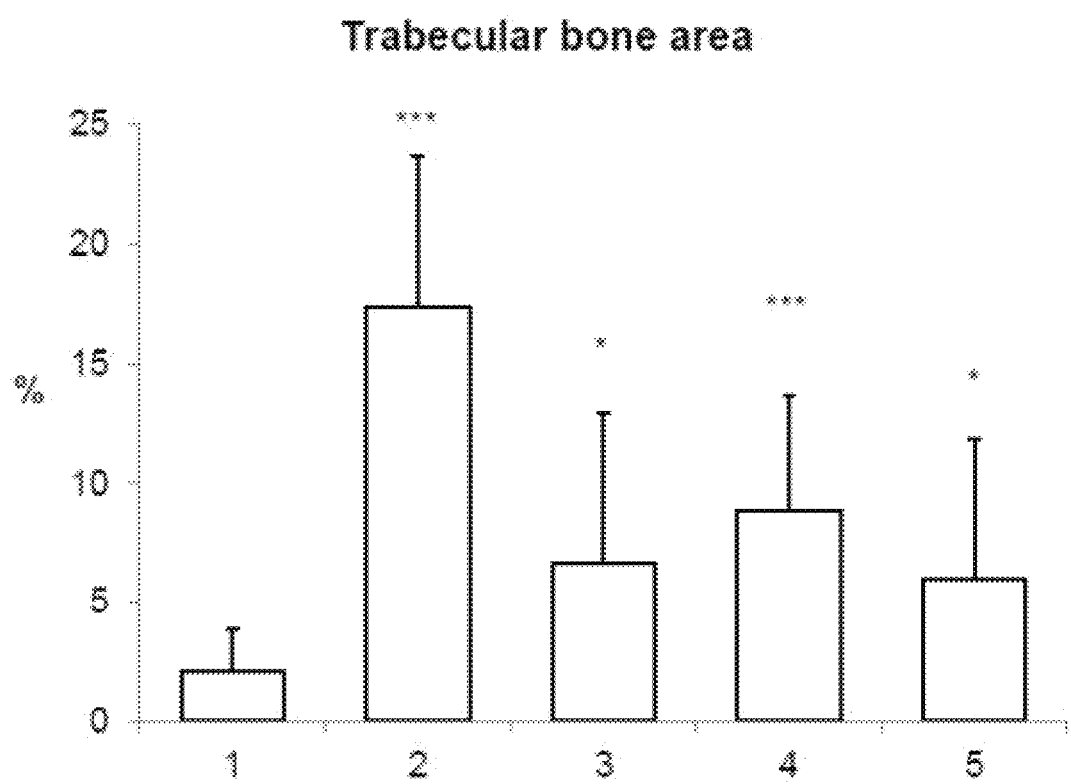
FIG. 21 shows illustrative results of trabecular bone area (relative to the intraosseous area). Statistical analysis was performed using Kruskal Wallis test followed by Mann-Whitney test for comparison against the control group. Three asterisks (***) indicate a statistically significant difference with a p-value<0.001 and one asterisk (*) with a p-value<0.05. Trabecular bone area was increased in all treatment groups.

FIG. 21 shows illustrative results of trabecular bone area (relative to the intraosseous area) of Groups 1-5. Trabecular bone area was increased in all treatment groups. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Figure 22A:
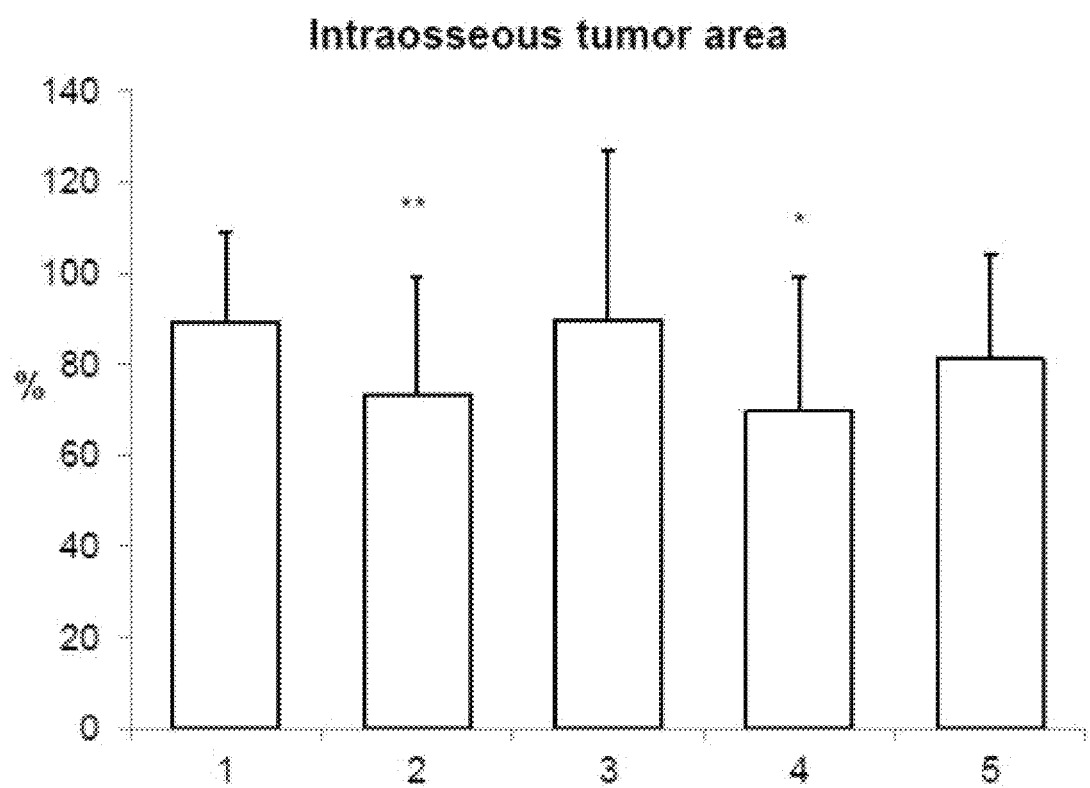
FIGS. 22a and 22b show illustrative results of intraosseous tumor area (relative to the intraosseous area) and total tumor area, respectively.
Figure 22B:
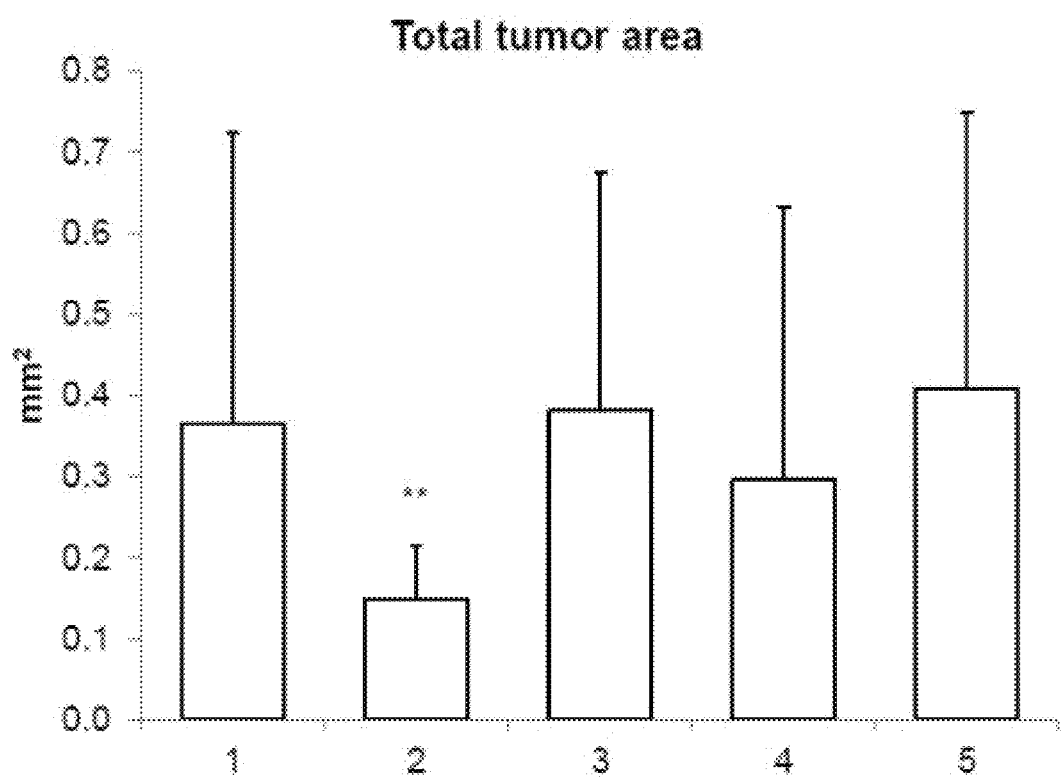

FIG. 22a shows intraosseous tumor area (relative to the intraosseous area) and FIG. 22b provides data of total tumor area. Intraosseous tumor area was decreased in groups 2 and 4 and total tumor area was decreased in group 2. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Figure 23:
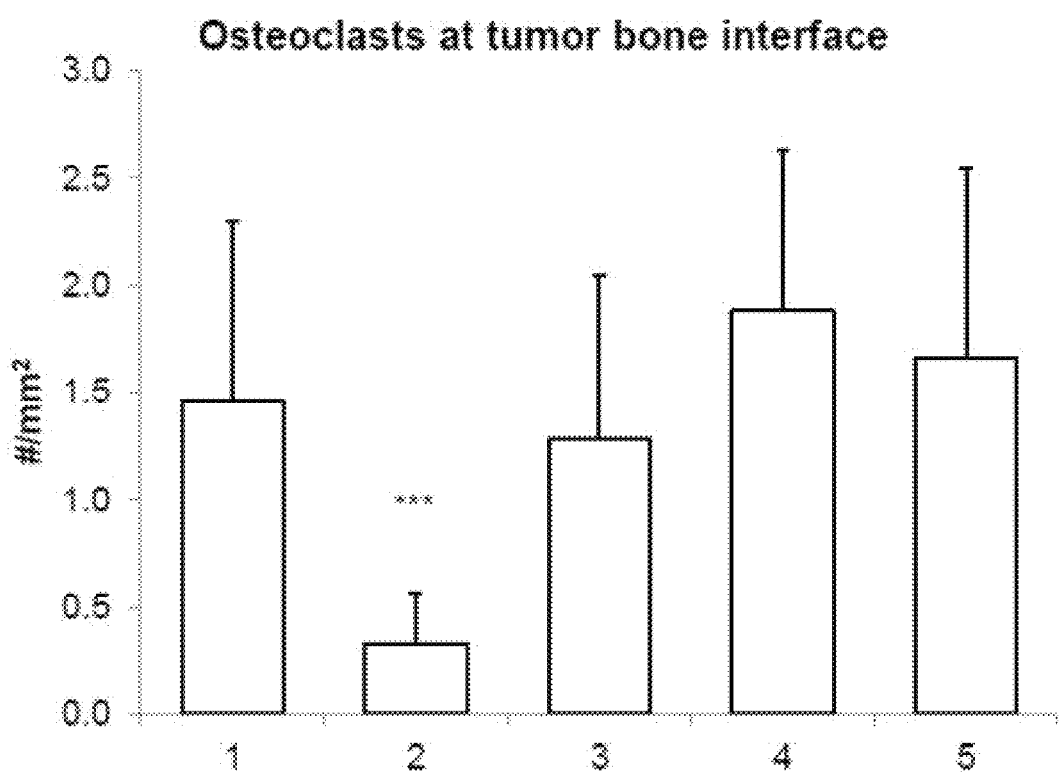
FIG. 23 shows illustrative results of number of osteoclasts at tumor-bone interface (relative to the tumor-bone interface length, #/mm). Statistical analysis was performed using Oneway ANOVA with logarithmic transformation followed by Dunnett's test for pairwise comparison against the control group. Three asterisks (***) indicate a statistically significant difference with a p-value<0.001. The number of osteoclasts at tumor-bone interface was decreased in group 2.

FIG. 23 shows illustrative data of Groups 1-5 re number of osteoclasts at tumor-bone interface (relative to the tumor-bone interface length, #/mm). The number of osteoclasts at tumor-bone interface was decreased in group 2. Group 1 received vehicle (corn oil) 20 ml/kg/d po; group 2 received vehicle 20 ml/kg/d po and zoledronic acid 0.1 mg/kg sc at days 1 and 14; groups 3, 4 and 5 received Compound 1 doses 30, 60 and 90 mg/kg/d po, respectively.

Summary of the Results

Table 6 shows summary of the results. An upwards arrow (↓) indicates increase and a downwards arrow (↓) a decrease. One asterisk (*) indicates a statistically significant difference with a p-value<0.05, two asterisks () with a p-value<0.01, and three asterisks (*) with a p-value<0.001. NS=Non-significant.

TABLE 6

Summary of the results

| METHOD/PARAMETER | Zoledronic acid | Compound 1 30 mg/kg/d | Compound 1 60 mg/kg/d | Compound 1 90 mg/kg/d |
|---|---|---|---|---|
| BODY WEIGHT | | | | |
| Relative change of body weight at sacrifice | NS | NS | NS | NS |
| Relative maximum weight | NS | NS | ↑* | NS |
| Study day of maximum weight | NS | NS | NS | NS |
| Relative loss of body weight from maximum weight | NS | NS | ↑** | ↑** |
| RADIOGRAPHIC ANALYSIS | | | | |
| Osteoblastic lesions, d28 | NS | NS | NS | NS |
| Osteoblastic lesions, sacr. | ↓*** | NS | ↓* | NS |
| Fractures, d28 | ↓* | ↓* | ↓* | NS |
| Fractures, sacr. | ↓*** | ↓* | ↓* | NS |
| Total osteolytic lesion area, d28 | ↓*** | NS | ↓* | NS |
| Total osteolytic lesion area, sacr. | ↓*** | NS | ↓** | NS |
| Mean osteolytic lesion area, d28 | ↓*** | NS | NS | ↓* |
| Mean osteolytic lesion area, sacr. | ↓*** | NS | ↓* | NS |
| Total osteolytic lesion count, d28 | ↑* | NS | NS | NS |
| Total osteolytic lesion count, sacr. | ↑** | NS | NS | NS |
| HISTOMORPHOMETRY | | | | |
| Intraosseous area | NS | NS | NS | NS |
| Cortical bone area | ↑*** | NS | NS | NS |
| Trabecular bone area | ↑*** | ↑* | ↑*** | ↑* |
| Intraosseous tumor area | ↓** | NS | ↓* | NS |
| Total tumor area | ↓** | NS | NS | NS |
| Osteoclast number at tumor-bone interface | ↓*** | NS | NS | NS |

CONCLUSIONS

Zoledronic acid inhibited the formation of osteolytic and osteoblastic lesions and fractures. The increase in osteolytic lesion count is a result of individual lesions prevented from fusing together. Zoledronic acid increased both cortical and trabecular bone area as quantified by histomorphometry and decreased the number of osteoclasts at the tumor-bone interface. Zoledronic acid had no effect on body weight. Zoledronic acid decreased both intraosseous and total tumor area. Compound 1 increased maximum body weight obtained at the dose 60 mg/kg/d. The loss of body weight was also increased compared to the control group in groups receiving 60 and 90 mg/kg/d of Compound 1. However, the weight loss was only around 6% which is not pathological. Compound 1 dose 60 mg/kg/d decreased the osteolytic lesion area. Compound 1 doses 30 and 60 mg/kg/d inhibited fractures at day 28 and at sacrifice. The dose 60 mg/kg/d inhibited also osteoblastic reactions at sacrifice. All Compound 1 doses increased the trabecular bone area and the dose 60 mg/kg/d was the most effective. Compound 1 had no effect on osteoclast number at tumor-bone interface. Compound 1 dose 60 mg/kg/d decreased the intraosseous tumor area, but had no effect on the total tumor area. In conclusion, Compound 1 had positive, bone protective effects in this aggressive model for prostate cancer bone metastasis and it also decreased the intraosseous tumor area at the dose level on 60 mg/kg/d.

Example 4

Safety and Efficacy of Compound 1 in Patients with Breast Cancer with Metastatic Bone Lesions The objective of this study is to assess the clinical benefit of two different dosing schedules of Compound 1 in patients with metastatic bone lesions from breast cancer.

Primary Outcome Measures:

Annual Overall Skeletal Morbidity Rate (SMR) [Time Frame: 12 months] [Designated as safety issue: No]

The SMR is computed by summing all Skeletal Related Event(s) (SREs) which occurred during the observation period and dividing it by the ratio "days of observation period/365.25", for each participant. SRE is defined as: pathologic bone fracture, spinal cord compression, surgery to bone both curative and prophylactic, radiation therapy to bone, or hypercalcemia of malignancy.

Secondary Outcome Measures:

Percentage of Participants Experiencing Skeletal Related Event(s) (SREs) [Time Frame: 12 month] [Designated as safety issue: No]

Skeletal Related Events (SREs) are defined as a:
pathologic bone fracture such as non-vertebral and vertebral compression fractures
spinal cord compression identified by positive diagnosis documented by X-ray evidence
surgery to bone both curative and prophylactic
radiation therapy to bone including palliative, therapeutic or prophylactic
hypercalcemia of malignancy, defined as a corrected serum calcium>12 mg/dl (3.00 mmol/l) or a lower level of hypercalcemia which is symptomatic and which requires active treatment other than rehydration.

Annual Incidence of Any Skeletal Related Events (SREs) [Time Frame: 12 months] [Designated as safety issue: No]

Skeletal Related Events (SREs) are defined as a:
pathologic bone fracture such as non-vertebral and vertebral
spinal cord compression identified by X-rays evidence
surgery to bone both curative and prophylactic
radiation therapy to bone including palliative, therapeutic or prophylactic
hypercalcemia of malignancy, defined as a corrected serum calcium>12 mg/dl (3.00 mmol/l) or a lower level of hypercalcemia which is symptomatic and which requires active treatment other than rehydration. Annual incidence for each SRE was computed in the same way as annual overall SMR.

Median Time to First Skeletal Related Event(s) (SRE) [Time Frame: 12 month] [Designated as safety issue: No]

Median Time to first skeletal related event (SRE) is defined as the time from randomization to the date of first occurrence of any SRE which includes at least one of the following: radiation therapy to bone, pathologic bone fracture, spinal cord compression, surgery to bone, and hypercalcemia of malignancy (HCM). Due to the few numbers of SRE, Kaplan-Meier estimate never reaches a failure probability>=25%; so median time, 25th and 75th percentiles are not determined. For this reason only the estimated percentage of patient SRE free are reported at each time point.

Percentage of Participants Skeletal Related Event (SRE) Free [Time Frame: 12 months] [Designated as safety issue: No]

Percentage of participants SRE free is defined as the Kaplan-Meier estimate of participants free of any Skeletal Related Events (SRE) at each time point.

Skeletal Related Events (SREs) are:
pathologic bone fracture; non-vertebral and vertebral
spinal cord compression identified by X-rays
surgery to bone both curative and prophylactic
radiation therapy to bone (palliative, therapeutic or prophylactic)
hypercalcemia of malignancy, defined as a corrected serum calcium>12 mg/dl (3.00 mmol/l) or a lower level which is symptomatic and requires treatment other than rehydration.

Composite Bone Pain Score According to the Brief Pain Inventory (BPI) Questionnaire [Time Frame: At Baseline, Month 3, Month 6, Month 9 and Month 12] [Designated as safety issue: No]

Bone pain is assessed by means of a pain score obtained using the Brief Pain Inventory (BPI) questionnaire. The BPI can produce three pain scores: worst pain, a composite pain score, and a pain interference score. The composite pain score, which is the average of questions 3, 4, 5 and 6 of the questionnaire is used in this study. Pain is rated on a scale of 0 (no pain) to 10 (pain as bad as you can imagine). The outcome is given as the median score for participants at baseline, and 3, 6, 9 and 12 months of treatment.

Evaluation of Pain According to Verbal Rating Scale (VRS) Based on Median Score Value [Time Frame: At Baseline, Month 3, Month 6, Month 9 and Month 12] [Designated as safety issue: No]

Pain intensity at rest and on movement is rated by the patient by means of a validated 6-point Verbal Rating Scale (VRS) and refers to the pain occurred during the last week before the assessment. Median score value is the median of all the observed scores (none=0, very mild=1, mild=2, moderate=3, severe=5 and very severe=6) at each time point.

Use Of Analgesic Medications According to the Analgesic Score Scale [Time Frame: At Baseline, Month 3, Month 6, Month 9 and Month 12] [Designated as safety issue: No]

The analgesic score used for this study is modified from the Radiation Therapy Oncology Group (RTOG) analgesic score scale. The scale represents type of medication administered from 0 to 4 where:

0=None; 1=Minor analgesics (aspirin, NSAID, acetaminophen, propoxyphene, etc.); 2=Tranquilisers, antidepressants, muscle relaxants, and steroids; 3=Mild narcotics (oxycodone, meperidine, codeine, etc.); 4=Strong narcotics (morphine, hydromorphone, etc.) The outcome is given a median score for the participants at Baseline and 3, 6, 9 and 12 months of treatment.

Assessment of the Eastern Cooperative Oncology Group (ECOG) Performance Score [Time Frame: At Baseline, Month 3, Month 6, Month 9 and Month 12] [Designated as safety issue: No]

ECOG Performance Score has 4 grades. 0=Fully active, able to carry out all pre-disease activities; 1=Restricted in strenuous activity but ambulatory and able to carry out work of light or sedentary nature; 2=Ambulatory and capable of all self-care but unable to carry out work activities. Active about 50% of waking hours; 3=Capable of limited self-care, confined to bed/chair more than 50% of waking hours; 4=Completely disabled; cannot carry on self-care. Totally confined to bed/chair. Outcome is given as median score for participants at Baseline and 3, 6, 9 and 12 months of treatment.

| Arms | Assigned Interventions |
| --- | --- |
| Experimental: Every 3 months Compound 1 as a 15-minute (at least) intravenous (i.v.) infusion every three months. The dose of study drug will be the same administered before the study entry, that is 50 mg or a reduced dose. Randomized patients will receive a maximum of 4 infusions in this group. | Drug: Compound 1 Compound 1 as a 15-minute (at least) intravenous (i.v.) infusion. The dose of study drug will be the same administered before the study entry, that is 50 mg or a reduced dose. |

-continued

| Arms | Assigned Interventions |
|---|---|
| Experimental: Every 4 weeks Compound 1 as a 15-minute (at least) intravenous (i.v.) infusion every 4 weeks. The dose of study drug will be the same administered before the study entry, that is 50 mg or a reduced dose. Patients randomized to this group will receive up to 12 infusions. | Drug: Compound 1 Compound 1 as a 15-minute (at least) intravenous (i.v.) infusion. The dose of study drug will be the same administered before the study entry, that is 50 mg or a reduced dose. |

Eligibility

Ages Eligible for Study: 18 Years and older

Genders Eligible for Study: Female

Accepts Healthy Volunteers: No

Criteria

Inclusion Criteria:

Female patients≥18 years of age; Written informed consent given; Histologically confirmed Stage 1V breast cancer with at least one bone metastasis radiologically confirms.

Eastern Cooperative Oncology Group (ECOG) performance status<2.

Life expectancy≥1 year.

Exclusion Criteria:

Treatments with other cyclohexenone compounds than Compound 1 at any time prior to study entry.

Serum creatinine>3 mg/dL (265 mmol/L) or calculated (Cockcroft-Gault formula) creatinine clearance (CLCr)<30 mL/min CrCl=({[140–age (years)]×weight (kg)}/[72× serum creatinine (mg/dL)])×0.85

Corrected (adjusted for serum albumin) serum calcium<8 mg/dl (2 mmol/L) or >12 mg/dL (3.0 mmol/L).

Current active dental problem including infection of the teeth or jawbone (maxilla or mandibular); dental or fixture trauma, or a recurrent or prior diagnosis of osteonecrosis of the jaw (ONJ), of exposed bone in the mouth, or of slow healing after dental procedures.

Recent (within 6 weeks) or planned dental or jaw surgery (e.g. extraction, implants).

Pregnant patients (with a positive pregnancy test prior to study entry) or lactating patients. Women of childbearing potential not using effective methods of birth control (e.g. abstinence, oral contraceptives or implants, IUD, vaginal diaphragm or sponge, or condom with spermicide).

History of non-compliance to medical regimens or potential unreliable behavior.

Known sensitivity to study drug(s) or class of study drug(s).

Patients with severe medical condition(s) that in the view of the investigator prohibits participation in the study Use of any other investigational agent in the last 30 days.

Example 5

Parenteral Formulation

To prepare a parenteral pharmaceutical composition suitable for administration by injection, 90 mg of a compound or its salt described herein is dissolved in DMSO and then mixed with 10 mL of 0.9% sterile saline. The mixture is incorporated into a dosage unit form suitable for administration by injection.

Example 6

Oral Formulation

To prepare a pharmaceutical composition for oral delivery, 90 mg of an exemplary Compound 1 was mixed with 90 mg of corn oil. The mixture was incorporated into an oral dosage unit in a capsule, which is suitable for oral administration.

In some instances, 90 mg of a compound described herein is mixed with 750 mg of starch. The mixture is incorporated into an oral dosage unit for, such as a hard gelatin capsule, which is suitable for oral administration.

Example 7

Sublingual (Hard Lozenge) Formulation

To prepare a pharmaceutical composition for buccal delivery, such as a hard lozenge, mix 90 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 8

Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

Example 9

Rectal Gel Formulation

To prepare a pharmaceutical composition for rectal delivery, 90 mg of a compound described herein is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 10

Topical Gel Composition

To prepare a pharmaceutical topical gel composition, 90 mg of a compound described herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method for treating a disease associated with bone metastasis in a subject comprising administering to said subject in need thereof a therapeutically effective amount of a compound having the structure:

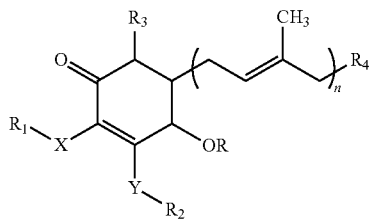

wherein each of X and Y independently is oxygen, $NR_5$ or sulfur;

R is a hydrogen or $C(=O)C_1\text{-}C_8$alkyl;

each of $R_1$, $R_2$ and $R_3$ independently is a hydrogen, methyl or $(CH_2)_m\text{—}CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_2\text{-}C_8$alkenyl, $C_2\text{-}C_8$alkynyl, aryl, glucosyl, wherein the 5 or 6-membered lactone, $C_1\text{-}C_8$alkyl, $C_2\text{-}C_8$alkenyl, $C_2\text{-}C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl;

each of $R_5$ and $R_6$ is independently a hydrogen or $C_1\text{-}C_8$alkyl;

$R_7$ is a $C_1\text{-}C_8$alkyl, $OR_5$ or $NR_5R_6$;

m=1-12; and n=1-12; or a pharmaceutically acceptable salt, metabolite, solvate or prodrug thereof.

2. A method for inhibiting hypercalcemia of malignancy, or inhibiting bone resorption, or treating osteolytic lesions in a subject comprising administering to said subject in need thereof a therapeutically effective amount of a compound having the structure:

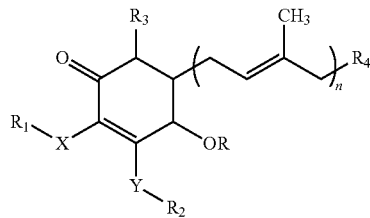

wherein each of X and Y independently is oxygen, $NR_5$ or sulfur;

R is a hydrogen or $C(=O)C_1\text{-}C_8$alkyl;

each of $R_1$, $R_2$ and $R_3$ independently is a hydrogen, methyl or $(CH_2)_m\text{—}CH_3$, $R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1\text{-}C_8$alkyl, $C_2\text{-}C_8$alkenyl, $C_2\text{-}C_8$alkynyl, aryl, glucosyl, wherein the 5 or 6-membered lactone, $C_1\text{-}C_8$alkyl, $C_2\text{-}C_8$alkenyl, $C_2\text{-}C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl;

each of $R_5$ and $R_6$ is independently a hydrogen or $C_1\text{-}C_8$alkyl;

$R_7$ is a $C_1\text{-}C_8$alkyl, $OR_5$ or $NR_5R_6$;

m=1-12; and n=1-12; or a pharmaceutically acceptable salt, metabolite, solvate or prodrug thereof.

3. The method of claim 1, wherein the subject has breast cancer or prostate cancer.

4. The method of claim 2, wherein the subject has breast cancer or prostate cancer.

5. The method of claim 1, wherein R is a hydrogen, $C(=O)C_3H_8$, $C(=O)C_2H_5$, or $C(=O)CH_3$.

6. The method of claim 2, wherein R is a hydrogen, $C(=O)C_3H_8$, $C(=O)C_2H_5$, or $C(=O)CH_3$.

7. The method of claim 1, wherein each of $R_1$, $R_2$ and $R_3$ independently is a hydrogen, methyl, ethyl, propyl, butyl, pentyl, hexyl, heptyl, or octyl.

8. The method of claim 2, wherein each of $R_1$, $R_2$ and $R_3$ independently is a hydrogen, methyl, ethyl, propyl, butyl, pentyl, hexyl, heptyl, or octyl.

9. The method of claim 1, wherein $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$.

10. The method of claim 1, wherein $R_4$ is $C_2H_5C(CH_3)_2OH$, $C_2H_5C(CH_3)_2OCH_3$, $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, aryl, $C_1\text{-}C_8$alkyl, $C_2\text{-}C_8$alkenyl, $C_2\text{-}C_8$alkynyl, or glucosyl, wherein the 5 or 6-membered lactone, aryl, $C_1\text{-}C_8$alkyl, $C_2\text{-}C_8$alkenyl, $C_2\text{-}C_8$alkynyl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl.

11. The method of claim 10, wherein $R_4$ is $C_1\text{-}C_8$alkyl optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_1\text{-}C_8$ cycloalkyl, and $C_1\text{-}C_8$ haloalkyl.

12. The method of claim 11, wherein $R_4$ is $CH_2CH=C(CH_3)_2$.

13. The method of claim 1, wherein said compound is

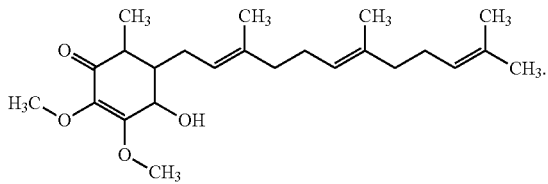 [SMILES: COC1=C(OC)C(O)C(C/C=C(\C)CC/C=C(\C)CCC=C(C)C)C(C)C1=O]

14. The method of claim 1, wherein said subject is human.

15. The method of claim 2, wherein $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$.

16. The method of claim 2, wherein $R_4$ is $C_2H_5C(CH_3)_2OH$, $C_2H_5C(CH_3)_2OCH_3$, $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, aryl, $C_1$-$C_8$alkyl, $C_2$-$C_8$alkenyl, $C_2$-$C_8$alkynyl, or glucosyl, wherein the 5 or 6-membered lactone, aryl, $C_1$-$C_8$alkyl, $C_2$-$C_8$alkenyl, $C_2$-$C_8$alkynyl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

17. The method of claim 16, wherein $R_4$ is $C_1$-$C_8$alkyl optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

18. The method of claim 17, wherein $R_4$ is $CH_2CH=C(CH_3)_2$.

19. The method of claim 2, wherein said compound is

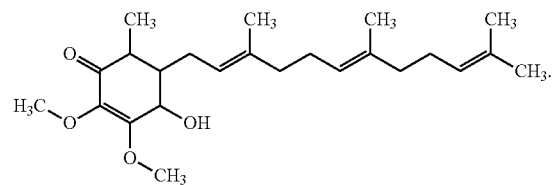 [SMILES: COC1=C(OC)C(O)C(C/C=C(\C)CC/C=C(\C)CCC=C(C)C)C(C)C1=O]

20. The method of claim 2, wherein said subject is human.

* * * * *